United States Patent
Sawyer

(10) Patent No.: US 12,077,548 B2
(45) Date of Patent: Sep. 3, 2024

(54) SUBSTITUTED IMIDAZOLES FOR THE INHIBITION OF TGF-β AND METHODS OF TREATMENT

(71) Applicant: CLAVIUS PHARMACEUTICALS, LLC, Ashland, VA (US)

(72) Inventor: J. Scott Sawyer, Placitas, NM (US)

(73) Assignee: Clavius Pharmaceuticals, LLC., Wilmington, DE (US)

( * ) Notice: Subject to any disclaimer, the term of this patent is extended or adjusted under 35 U.S.C. 154(b) by 767 days.

(21) Appl. No.: 17/269,959

(22) PCT Filed: Aug. 22, 2019

(86) PCT No.: PCT/US2019/047650
§ 371 (c)(1),
(2) Date: Feb. 19, 2021

(87) PCT Pub. No.: WO2020/041562
PCT Pub. Date: Feb. 27, 2020

(65) Prior Publication Data
US 2022/0064187 A1 Mar. 3, 2022

Related U.S. Application Data

(60) Provisional application No. 62/721,335, filed on Aug. 22, 2018.

(51) Int. Cl.
C07D 519/00 (2006.01)
C07D 498/04 (2006.01)
C07D 513/04 (2006.01)

(52) U.S. Cl.
CPC ......... *C07D 519/00* (2013.01); *C07D 498/04* (2013.01); *C07D 513/04* (2013.01)

(58) Field of Classification Search
None
See application file for complete search history.

(56) References Cited

U.S. PATENT DOCUMENTS

| | | | |
|---|---|---|---|
| 8,080,568 B1 | 12/2011 | Kim et al. | |
| 2012/0252721 A1 | 10/2012 | Dousson et al. | |
| 2016/0096823 A1 | 4/2016 | McMillen et al. | |
| 2016/0257690 A1 | 9/2016 | Kinsella et al. | |
| 2020/0239462 A1 | 7/2020 | Sawyer | |

FOREIGN PATENT DOCUMENTS

| | | | |
|---|---|---|---|
| JP | 2010-503702 | 2/2010 | |
| JP | 2011-515371 | 5/2011 | |
| JP | 2011-526295 | 10/2011 | |
| JP | 2011-529021 | 12/2011 | |
| JP | 2012-514044 | 12/2011 | |
| JP | 2014-514296 | 6/2014 | |
| JP | 2014-520846 | 8/2014 | |
| JP | 2016-535745 | 11/2016 | |
| JP | 2018-501209 | 1/2018 | |
| JP | 2018-510857 | 4/2018 | |
| JP | 2020-512400 | 4/2020 | |
| WO | WO 2008/094556 | 8/2008 | |
| WO | WO 2009/115572 | 9/2009 | |
| WO | WO 2009/158473 | 12/2009 | |
| WO | WO 2013/009140 | 1/2013 | |
| WO | WO 2016/081364 | 5/2016 | |
| WO | WO-2016081364 A1 * | 5/2016 | ........... A61K 31/416 |
| WO | WO 2016/140884 | 9/2016 | |
| WO | WO 2018/068759 | 4/2018 | |

OTHER PUBLICATIONS

Scheltens et al., "Alzheimer's disease", 2016, Seminar, 338, pp. 505-517 (Year: 2016).*
Zverova, "Clinical aspects of Alzheimer's disease", 2019, Clinical Biochemistry, 72, pp. 3-6 (Year: 2019).*
De Strooper et al., "The Cellular Phase of Alzheimer's Disease", 2016, Cell, 164, pp. 603-615 (Year: 2016).*
Callahan et al., "Identification of Novel Inhibitors of the Transforming Growth Factor β1 (TGF-β1) Type 1 Receptor (ALK5)," Journal of Medicinal Chemistry, vol. 45, No. 5, Jan. 30, 2002, pp. 999-1001. Abstract only.
Ren et al., "Pharmacophore modeling and virtual screening for the discovery of new transforming growth factor-β type I receptor (ALK5) inhibitors," European Journal of Medicinal Chemistry, vol. 44, No. 11, Nov. 2009, pp. 4259-4265. Abstract only.
Article 94(3) Communication for Europe Patent Application No. 18823320.9, dated Mar. 23, 2022, 4 pages.
Official Action (with English translation) for Japan Patent Application No. 2020-501434, dated Aug. 23, 2022, 10 pages.
Official Action (with English translation) for Japan Patent Application No. 2021-509918, dated Feb. 8, 2022, 7 pages.
Notice of Allowance (with English translation of allowed claims) for Japan Patent Application No. 2021-509918, dated Aug. 23, 2022, 45 pages.
"RN 1269148-53-9 Registry," Supplied by ChemBridge Corporation, Chemical Abstracts Service, Mar. 21, 2011, 1 page.
Gaikwad et al., "The Use of Bioisoterism in Drug Design and Molecular Modification," American Journal of PharmTech Research, vol. 2, No. 4, 2012, 23 pages.

(Continued)

*Primary Examiner* — Jeffrey H Murray
*Assistant Examiner* — Madeline E Braun
(74) *Attorney, Agent, or Firm* — Sheridan Ross P.C.

(57) ABSTRACT

This disclosure relates to low molecular weight substituted imidazoles that inhibit the TGF-b signaling pathway. More specifically, this disclosure relates to methods of using said imidazoles for the treatment of diseases related to the TGF-b signaling pathways including, but not limited to, atherosclerosis, Marfan syndrome, Loeys-Dietz syndrome, obesity, diabetes, multiple sclerosis, keratoconus, idiopathic pulmonary fibrosis, Alzheimer's Disease, chronic kidney disease, and scleroderma.

19 Claims, No Drawings

(56) References Cited

OTHER PUBLICATIONS

Guo et al., "Synthesis and biological evaluation of 1,2,4-trisubstituted imidazoles as inhibitors of transforming growth factor-β type I receptor (ALK5)," Bioorganic & Medicinal Chemistry Letters, vol. 23, No. 21, Nov. 1, 2013, pp. 5850-5854. Abstract only.

Jin et al., "Discovery of N-((4-([1,2,4]Triazolo[1,5-a]pyridin-6-yl)-5-(6-methylpyridin-2-yl)-1H-imidazol-2-yl)methyl)-2-fluoroaniline (EW-7197): a Highly Potent, Selective, and Orally Bioavailable Inhibitor of TGF-β Type I Receptor Kinase as Cancer Immunotherapeutic/Antifibrotic Agent," Journal of Medical Chemistry, vol. 57, No. 10, May 2, 2014, pp. 4213-4238.

International Search Report and Written Opinion for International (PCT) Patent Application No. PCT/US2018/024133, dated Jun. 15, 2018, 8 pages.

International Search Report and Written Opinion for International (PCT) Patent Application No. PCT/US2019/047650, dated Dec. 27, 2019, 10 pages.

Extended European Search Report for European Patent Application No. 18823320.9, dated Jul. 29, 2020, 10 pages.

Official Action for U.S. Appl. No. 16/496,703, dated Sep. 22, 2020, 9 pages.

Official Action for U.S. Appl. No. 16/496,703, dated Feb. 5, 2021 6 pages.

Official Action (with English translation) for Japan Patent Application No. 2020-501434, dated Nov. 30, 2021, 15 pages.

Notice of Allowance for U.S. Appl. No. 16/496,703, dated May 14, 2021, 5 pages.

Extended European Search Report for European Patent Application No. 19852789.7, dated Jun. 1, 2022, 5 pages.

Article 94(3) Communication for Europe Patent Application No. 19852789.7, dated Feb. 9, 2023, 4 pages.

Official Action for U.S. Appl. No. 17/476,943, dated Apr. 18, 2023, 7 pages.

\* cited by examiner

SUBSTITUTED IMIDAZOLES FOR THE INHIBITION OF TGF-β AND METHODS OF TREATMENT

CROSS REFERENCE TO RELATED APPLICATIONS

This application is a national stage application under 35 U.S.C. 371 and claims the benefit of PCT Application No. PCT/US2019/047650 having an international filing date of 22 Aug. 2019, which designated the United States, which PCT application claimed the benefit of U.S. Provisional Application No. 62/721,335 filed 22 Aug. 2018, the disclosures of which are incorporated herein by reference in their entirety.

FIELD OF THE DISCLOSURE

This disclosure relates to low molecular weight substituted imidazoles that inhibit the TGF-β signaling pathway. More specifically, this disclosure relates to methods of using said imidazoles for the treatment of diseases related to the TGF-β signaling pathways including, but not limited to, atherosclerosis, Marfan syndrome, Loeys-Dietz syndrome, obesity, diabetes, multiple sclerosis, keratoconus, idiopathic pulmonary fibrosis, Alzheimer's Disease, chronic kidney disease, and scleroderma.

The compounds disclosed herein may be especially applicable to the treatment of various oncology indications, including, but not limited to, lung cancer, gastric cancer, myelodysplastic syndrome (MDS), melanoma, colon cancer, renal cancer, and preferably glioblastoma (GBM), pancreatic cancer, and hepatocellular carcinoma (HCC). These diseases may be treated in mammals, including domesticated quadrupeds and preferably humans. The compounds of the present disclosure may be active in inhibiting the kinase domains of the Type I receptors (ACVR1B, also known as ALK4, TGFβR1, also known as ALK5, BMPR1A, also known as ALK3, BMPR1B, also known as ALK6, and ACVR1C, also known as ALK7) and/or the Type II receptors (ACVR2A, ACVR2B, BMPR2, and TGFβRII).

BACKGROUND

The TGF-β signaling pathway is known to regulate a number of cellular processes involving growth, differentiation, development, mgration, and apoptosis. TGF-β superfamily ligands, including TGF-β 1, TGF-β2, and TGF-β3, bind to various combinations of Type I and Type II receptors in overall hexameric complexes consisting of two identical ligands bound to a heterotetrameric receptor complex, ultimately resulting in the phosphorylation of the Type I receptor and subsequent phosphorylation and activation of SMAD2/SMAD3 intracellular signaling proteins. The cascade thus initiated results in further activation of downstream signaling elements ultimately activating a number of nuclear transduction proteins controlling transcription. The signaling pathway comprised of TGF-β/ALK5 combinations is especially important in oncology indications and may be disrupted by blocking the key kinase domain of the ALK5 receptor.

Despite the existence of known ALK5 inhibitors, additional classes of compounds are needed to probe potential efficacy in the diverse diseases mentioned above, particularly in the area of oncology. Improvements over existing inhibitors could include, but not be limited to, greater therapeutic indices, more favorable formulation or biopharmaceutical properties, or more optimized tissue distribution. The compounds of the present disclosure have been discovered to have utility in treating the diseases described above.

SUMMARY

The present disclosure provides substituted imidazoles for the inhibition of the TGF-β signaling pathway and methods for treating disease employing said compounds.

DETAILED DESCRIPTION

As described above, this disclosure includes low molecular weight substituted imidazoles that may inhibit the TGF-β signaling pathways. More specifically, this disclosure relates to methods of using said substituted imidazoles for the treatment of diseases related to the TGF-β signaling pathways including, but not limited to, atherosclerosis, Marfan syndrome, Loeys-Dietz syndrome, obesity, diabetes, multiple sclerosis, keratoconus, idiopathic pulmonary fibrosis, Alzheimer's Disease, chronic kidney disease, and scleroderma.

The compounds disclosed herein therefore, may be especially applicable to the treatment of various oncology indications, including, but not limited to, lung cancer, gastric cancer, myelodysplastic syndrome (MDS), melanoma, colon cancer, renal cancer, and preferably glioblastoma (GBM), pancreatic cancer, and hepatocellular carcinoma (HCC). These diseases may be treated in mammals, including domesticated quadrupeds and preferably humans. The compounds within the present disclosure may be active in inhibiting the kinase domains of the Type I receptors (ACVR1B, also known as ALK4, TGFβR1, also known as ALK5, BMPR1A, also known as ALK3, BMPR1B, also known as ALK6, and ACVR1C, also known as ALK7) and/or the Type II receptors (ACVR2A, ACVR2B, BMPR2, and TGFβRII).

In an embodiment of the present disclosure, a compound of Formula (I) and pharmaceutically acceptable salts, hydrates, or solvates thereof are provided:

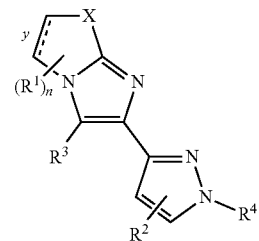

Formula (I)

In embodiments of this disclosure, $R^1$ is:
a hydrogen atom;
a halogen atom;
an alkyl group containing 1 to 6 carbon atoms;
an alkyl group containing 1 to 6 carbon atoms, substituted with a cycloalkyl group containing 3 to 7 carbon atoms;
an alkyl group containing 1 to 6 carbon atoms, substituted with 2 to 7 halogens;
an alkenyl group containing 1 to 6 carbon atoms;
an alkynyl group containing 1 to 6 carbon atoms;
a cycloalkyl group containing 3 to 7 carbon atoms;
a phenyl group;
a phenyl group substituted with an alkyl group containing 1 to 6 carbons;

a phenyl group with an alkyl group containing 1 to 6 carbons, optionally further substituted with a hydroxyl group, an alkoxy group containing 1 to 6 carbon atoms, an alkoxy group containing 1 to 6 carbon atoms substituted with an alkoxy group containing 1 to 6 carbon atoms, or an alkoxy group having 1 to 6 carbon atoms substituted with an alkylamino group containing 1 to 6 carbon atoms;

a carboxylic acid group;

a carboxylic ester group;

a carboxamide group; or $C(O)R^5$;

$R^2$ is:

a hydrogen atom;

a halogen atom;

an alkyl group containing 1 to 6 carbon atoms;

an alkyl group containing 1 to 6 carbon atoms, substituted with a cycloalkyl group containing 3 to 7 carbon atoms, or a cycloalkyl group containing 1 to 3 heteroatoms selected from the group consisting of O, N, and S;

an alkyl group containing 1 to 6 carbon atoms, substituted with 2 to 7 halogens;

an alkyl group containing 1 to 6 carbon atoms, substituted with 1 to 2 heteroatoms selected from the group consisting of O, N, and S;

an alkenyl group containing 1 to 6 carbon atoms;

an alkynyl group containing 1 to 6 carbon atoms;

a cycloalkyl group containing 3 to 7 carbon atoms;

a phenyl group; or a phenyl group substituted with an alkyl group containing 1 to 6 carbons;

$R^3$ is:

a phenyl group;

a phenyl group substituted with 1 to 5 members selected from a group consisting of a halogen, an alkyl group containing 1 to 6 carbon atoms, an alkenyl group containing 1 to 6 carbon atoms, an alkynyl group containing 1 to 6 carbon atoms, an alkoxy group containing 1 to 6 carbon atoms, a phenyl group, a pyridyl group, a hydroxyl group, an amido group, a carbamoyl group, or a cyano group;

an unsubstituted heteromonocyclic group;

an unsubstituted heterobicyclic group;

a heteromonocyclic or a heterobicyclic group substituted with 1 to 5 members selected from a group consisting of a halogen and an alkyl group containing 1 to 6 carbon atoms, optionally substituted with a cycloalkyl group containing 3 to 7 carbon atoms or a cycloalkyl group containing 1 to 3 heteroatoms selected from the group consisting of O, N, and S; a phenyl group, a pyridyl group, an alkoxy group containing 1 to 6 carbon atoms, a hydroxyl group, a hydroxyalkyl group, an alkylsulfonyl group, an alkylsulfinyl group, an arylsulfonyl group, an arylsulfinyl group, a cycloalkylsulfonyl group, a cycloalkylsulfinyl group, a heterocyclosulfonyl group, a heterocyclosulfinyl group, an amino group, an amido group, a carbamoyl group, a cyano group, an aryl group substituted with a carbamoyl group, a sulfonyl group, a hydroxyalkyl group, a heteroaryl group substituted with a primary amide group, a secondary amide group, a tertiary amide group, a cyclic secondary amide group, a cyclic tertiary amide group, a sulfonyl group, or a hydroxyalkyl group, wherein the sulfonyl group or hydroxyalkyl group is optionally further substituted with at least one of the group consisting of $R^5$ and $R^6$; an alkenyl group containing 1 to six carbon atoms, wherein the alkenyl group is optionally further substituted with an amido group;

$R^4$ is:

a hydrogen atom;

an alkyl group containing 1 to 12 carbon atoms;

an alkyl group containing 1 to 12 carbon atoms substituted with an alkoxy group containing 1 to 6 carbon atoms, a hydroxyl group, an alkoxyphenylalkoxy group having 8 to 12 carbon atoms, a morpholino group, a piperidinyl group, a pyrrolidino group, or a cyclic ether group containing 3 to 6 carbon atoms;

an alkyl group having 1 to 6 carbon atoms substituted with 1 to 7 halogen atoms;

an alkenyl group containing 1 to 6 carbon atoms;

an alkynyl group containing 1 to 6 carbon atoms;

a cycloalkyl group containing 3 to 7 carbon atoms;

a cycloalkyl group containing 3 to 9 carbon atoms substituted with 1 to 7 halogens, or an oxo group;

a cyclic ether containing 3 to 6 carbon atoms; or a 4-piperidinyl group;

$R^5$ is:

an alkyl group having 1 to 6 carbon atoms; a cycloalkyl group containing 3 to 7 carbon atoms optionally substituted with 1 to 7 halogens, an aryl group, or a heteroaryl group;

$R^6$ is:

an alkyl group having 1 to 6 carbon atoms; a cycloalkyl group containing 3 to 7 carbon atoms, an aryl group, or a heteroaryl group;

X is:

$CH_2$, CH, C, O, S, or N;

n is:

0-2; and y is:

a single or double bond.

As used herein, the term "halogen" may be understood to include a fluorine, chlorine, bromine, or an iodine atom.

The term "alkyl" may be understood to include a saturated aliphatic hydrocarbon containing a specified number of carbon atoms in either a straight-chain or branched-chain configuration. Examples include, but are not limited to, methyl, ethyl, n-propyl, isopropyl, n-butyl, isobutyl, sec-butyl, tert-butyl, n-pentyl, neopentyl, n-hexyl, and n-heptyl. Alkyl groups may be optionally substituted with one or more substituents including groups such as alkoxy, cycloalkoxy, amino, nitro, cyano, carboxy, halogen, hydroxyl, sulfonyl, or mercapto.

The term "alkenyl" may be understood to refer to an unsaturated aliphatic hydrocarbon group containing a specified number of carbon atoms, in either a straight-chain or branched-chain configuration, and at least one double bond. Examples include, but are not limited to, ethylene, propylene, isopropylene, butylene, isobutylene, sec-butylene, tert-butylene, n-pentylene, n-hexylene, and n-heptylene. As used herein, alkenyl groups may be substituted with one or more substituents including groups such as alkoxy, cycloalkoxy, heterocycloalkoxy, aryloxy, heteroaryloxy, aralkyloxy, heteroarylalkoxy, amino, nitro, cyano, carboxy, halogen, hydroxyl, sulfonyl, mercapto, alkylsulfanyl, alkylsulfinyl, alkylsulfonyl, aminocarbonyl (amido), alkylcarbonylamino, cycloalkylcarbonylamino, cycloalkylalkylcarbonylamino, heteroarylcarbonylamino, heteroaralkylcarbonylamino, urea, thiourea, sulfamoyl, sulfamide, alkoxycarbonyl, or alkylcarbonyloxy.

As used herein, the term "alkynyl" may be understood to refer to an unsaturated aliphatic group containing a specified number of carbon atoms in either a straight-chain or branched-chain configuration and at least one triple bond. Examples include, but are not limited to, ethyne, propyne, butyne, pentyne, hexyne, and heptyne. Alkynyl groups may be substituted with one or more substituents including groups such as alkoxy, cycloalkoxy, heterocycloalkoxy, aryloxy, heteroaryloxy, aralkyloxy, heteroarylalkoxy, amino, nitro, cyano, carboxy, halogen, hydroxyl, sulfonyl, mercapto, alkylsulfanyl, alkylsulfimyl, alkylsulfonyl, aminocarbonyl (amido), alkylcarbonylamino, cycloalkylcarbonylamino, cycloalkylalkylcarbonylamino, heteroarylcarbonylamino, heteroaralkylcarbonylamino, urea, thiourea, sulfamoyl, sulfamide, alkoxycarbonyl, or alkylcarbonyloxy.

As used herein, the term "cycloalkyl" may be understood to refer to an aliphatic carbocyclic ring of 3 to 10 carbon atoms. Examples of cycloalkyl groups include, but are not limited to, cyclopropyl, cyclobutyl, cyclopentyl, cyclohexyl, cycloheptyl, cyclooctyl, adamantyl, norbornyl, octahydroindenyl, decahydronaphthyl, bicyclo[3.2.1]octyl, and bicyclo[2.2.2]octyl.

As used herein, the term "alkoxy" may be understood to refer to an oxygen-linked alkyl group.

As used herein, the term "heteromonocyclic" may be understood to refer to an aromatic or non-aromatic 3 to 8 atom heterocyclic ring system consisting of a single ring containing at least one heteroatom (e.g. nitrogen, oxygen, or sulfur) with the balance of the atoms in the ring consisting of carbon and/or other heteroatoms. Examples of heteromonocyclic groups include, but are not limited to, aziridine, azetidine, pyrrolidine, piperadine, piperazine, oxetane, furan, tetrahydrofuran, pyran, tetrahydropyran, pyrrole, imidazole, pyrazole, pyridine, pyridazine, pyrazine, pyrimidine, triazine, thiazole, isothiazole, oxazole, isoxazole, thiadiazole, oxadiazole, and triazole.

As used herein, the term "heterobicyclic" may be understood to refer to an aromatic or non-aromatic 7 to 12 atom heterocyclic ring system consisting of two fused rings containing at least one heteroatom (e.g. nitrogen, oxygen, or sulfur) with the balance of the atoms in the ring consisting of carbon and/or other heteroatoms. Examples of heterobicyclic groups include, but are not limited to, indole, benzimidazole, indazole, benzotriazole, benzoxazole, benzothiazole, pyrrolopyridine, pyrrolopyrimidine, pyrrolopyrazine, pyrrolopyridazine, pyrazolopyridine, pyrazolopyrimidine, pyrazolopyrazine, pyrazolopyridazine, imidazopyridine, imidazopyrimidine (purine), imidazopyrazine, imidazopyridazine, methylenedioxybenzene, triazolopyridine, triazolopyrimidine, quinoline, isoquinoline, cinnoline, phthalazine, quinazoline, quinoxaline, naphthyridine, azaquinazoline, azaquinoxaline, and azanaphthydridine.

For example, the following paragraphs describe some preferred embodiments of the present disclosure.

In some preferred embodiments, $R^1$ is hydrogen, methyl, hydroxymethyl, carboxyl, acetyl, amido, or fluoro.

In some preferred embodiments, $R^2$ is hydrogen, methyl, or fluoro.

In some preferred embodiments, $R^3$:

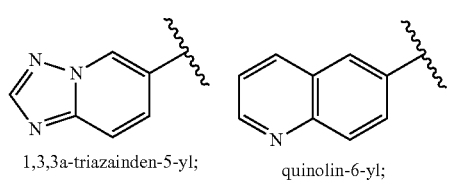

1,3,3a-triazainden-5-yl; quinolin-6-yl;

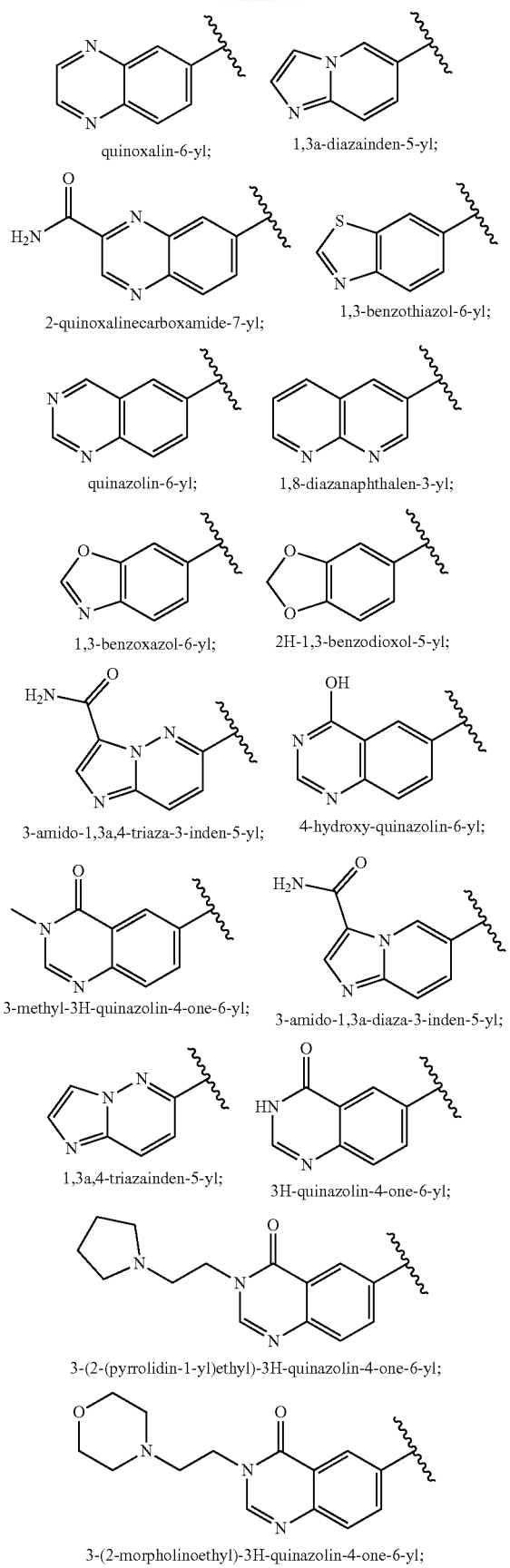

quinoxalin-6-yl; 1,3a-diazainden-5-yl;

2-quinoxalinecarboxamide-7-yl; 1,3-benzothiazol-6-yl;

quinazolin-6-yl; 1,8-diazanaphthalen-3-yl;

1,3-benzoxazol-6-yl; 2H-1,3-benzodioxol-5-yl;

3-amido-1,3a,4-triaza-3-inden-5-yl; 4-hydroxy-quinazolin-6-yl;

3-methyl-3H-quinazolin-4-one-6-yl; 3-amido-1,3a-diaza-3-inden-5-yl;

1,3a,4-triazainden-5-yl; 3H-quinazolin-4-one-6-yl;

3-(2-(pyrrolidin-1-yl)ethyl)-3H-quinazolin-4-one-6-yl;

3-(2-morpholinoethyl)-3H-quinazolin-4-one-6-yl;

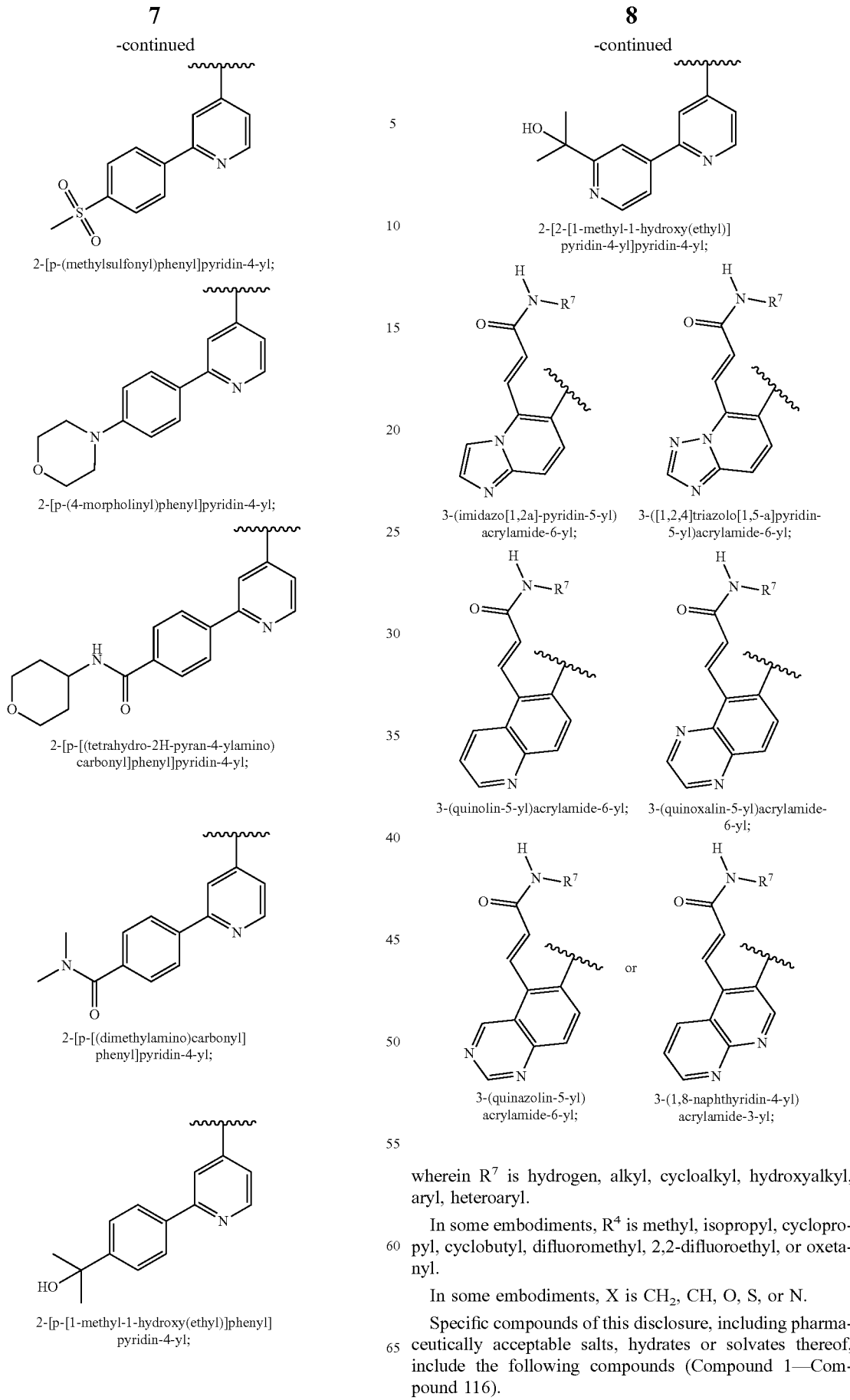

wherein R⁷ is hydrogen, alkyl, cycloalkyl, hydroxyalkyl, aryl, heteroaryl.

In some embodiments, $R^4$ is methyl, isopropyl, cyclopropyl, cyclobutyl, difluoromethyl, 2,2-difluoroethyl, or oxetanyl.

In some embodiments, X is $CH_2$, CH, O, S, or N.

Specific compounds of this disclosure, including pharmaceutically acceptable salts, hydrates or solvates thereof, include the following compounds (Compound 1—Compound 116).

TABLE 1
EXEMPLARY COMPOUNDS OF FORMULA (I)
| Compound No. | Structure and Name |
|---|---|
| 1 | 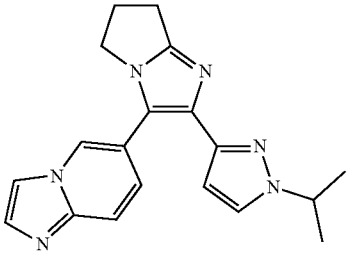 [SMILES: CC(C)n1ccc(-c2nc3n(c2-c2ccc4nccn4c2)CCC3)n1]
6-(2-(1-Isopropyl-1H-pyrazol-3-yl)-6,7-dihydro-5H-pyrrolo[1,2-a]imidazol-3-yl)imidazo[1,2-a]pyridine |
| 2 | 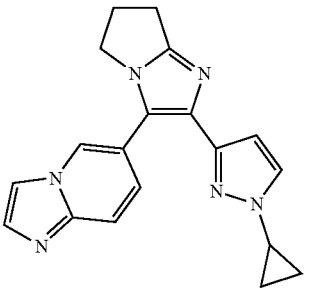 [SMILES: c1cn2cc(-c3c(-c4ccn(C5CC5)n4)nc4n3CCC4)ccc2n1]
3-{2-(1,3a-Diaza-5-indenyl)-1,4-diazabicyclo[3.3.0]octa-2,4-dien-3-yl}-1-cyclopropyl-1H-pyrazole |
| 3 | 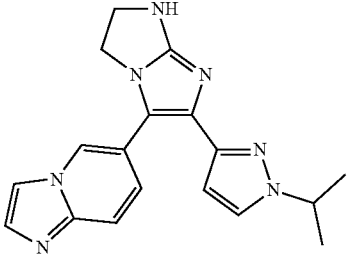 [SMILES: CC(C)n1ccc(-c2nc3n(c2-c2ccc4nccn4c2)CCN3)n1]
6-(6-(1-Isopropyl-1H-pyrazol-3-yl)-2,3-dihydro-1H-imidazo[1,2-a]imidazol-5-yl)imidazo[1,2-a]pyridine |
| 4 | 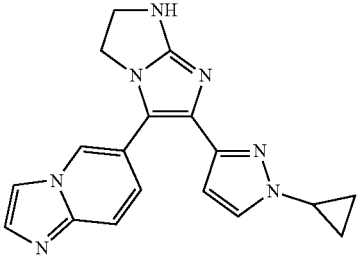 [SMILES: c1cn2cc(-c3c(-c4ccn(C5CC5)n4)nc4n3CCN4)ccc2n1]
6-(6-(1-Cyclopropyl-1H-pyrazol-3-yl)-2,3-dihydro-1H-imidazo[1,2-a]imidazol-5-yl)imidazo[1,2-a]pyridine |

TABLE 1-continued

EXEMPLARY COMPOUNDS OF FORMULA (I)

| Compound No. | Structure and Name |
|---|---|
| 5 | 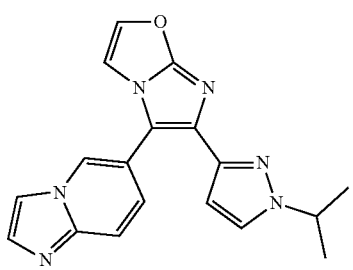 [SMILES: CC(C)n1ccc(-c2nc3occn3c2-c2ccc3nccn3c2)n1]<br>8-(1,3a-Diaza-5-indenyl)-7-(1-isopropyl-1H-pyrazol-3-yl)-4-oxa-1,6-diazabicyclo[3.3.0]octa-2,5,7-triene |
| 6 | 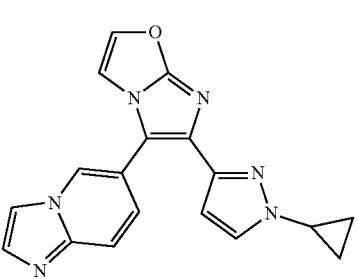 [SMILES: c1cn2cc(-c3c(-c4ccn(C5CC5)n4)nc4occn34)ccc2n1]<br>8-(1,3a-Diaza-5-indenyl)-7-(1-cyclopropyl-1H-pyrazol-3-yl)-4-oxa-1,6-diazabicyclo[3.3.0]octa-2,5,7-triene |
| 7 | 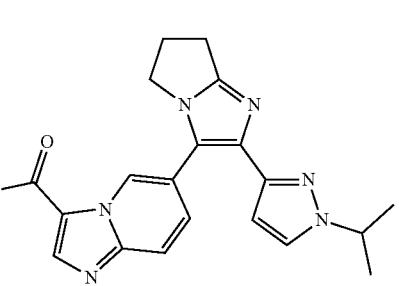<br>5-{3-(1-Isopropyl-1H-pyrazol-3-yl)-1,4-diazabicyclo[3.3.0]octa-2,4-dien-2-yl}-1,3a-diaza-3-indenecarboxamide |
| 8 | 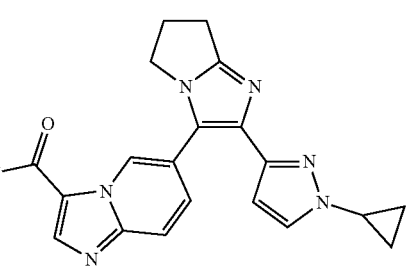<br>5-{3-(1-Cyclopropyl-1H-pyrazol-3-yl)-1,4-diazabicyclo[3.3.0]octa-2,4-dien-2-yl}-1,3a-diaza-3-indenecarboxamide |

TABLE 1-continued

EXEMPLARY COMPOUNDS OF FORMULA (I)

| Compound No. | Structure and Name |
|---|---|
| 9 | 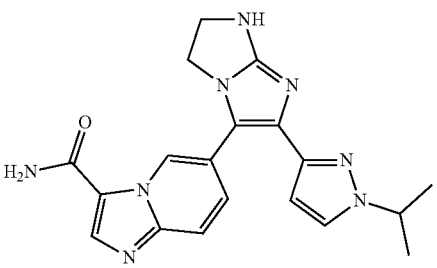<br>5-{3-(1-Isopropyl-1H-pyrazol-3-yl)-1,4,6-triazabicyclo[3.3.0]octa-2,4-dien-2-yl}-1,3a-diaza-3-indenecarboxamide |
| 10 | 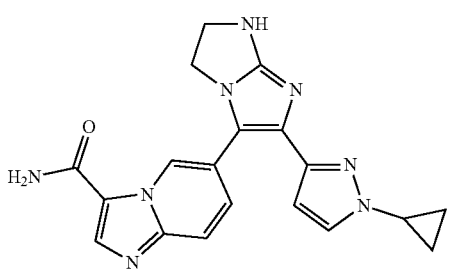 [SMILES: NC(=O)c1cnc2ccc(-c3c(-c4ccn(C5CC5)n4)nc4n3CCN4)cn12]<br>5-{3-(1-Cyclopropyl-1H-pyrazol-3-yl)-1,4,6-triazabicyclo[3.3.0]octa-2,4-dien-2-yl}-1,3a-diaza-3-indenecarboxamide |
| 11 | 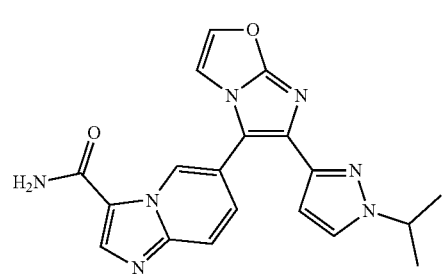 [SMILES: CC(C)n1ccc(-c2nc3occn3c2-c2ccc3ncc(C(N)=O)n3c2)n1]<br>5-{7-(1-Isopropyl-1H-pyrazol-3-yl)-4-oxa-1,6-diazabicyclo[3.3.0]octa-2,5,7-trien-8-yl}-1,3a-diaza-3-indenecarboxamide |
| 12 | 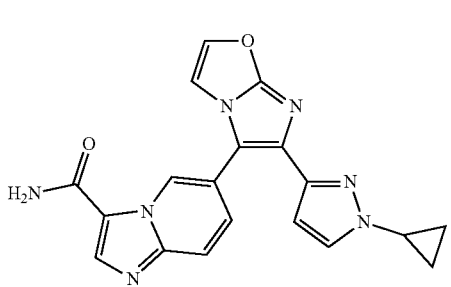<br>5-{7-(1-Cyclopropyl-1H-pyrazol-3-yl)-4-oxa-1,6-diazabicyclo[3.3.0]octa-2,5,7-trien-8-yl}-1,3a-diaza-3-indenecarboxamide |

TABLE 1-continued

EXEMPLARY COMPOUNDS OF FORMULA (I)

| Compound No. | Structure and Name |
|---|---|
| 13 | 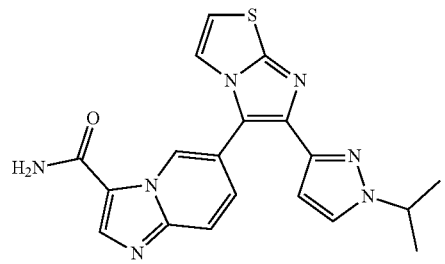<br>5-{7-(1-Isopropyl-1H-pyrazol-3-yl)-4-thia-1,6-diazabicyclo[3.3.0]octa-2,5,7-trien-8-yl}-1,3a-diaza-3-indenecarboxamide |
| 14 | 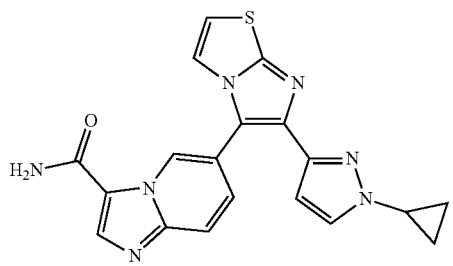 [SMILES: NC(=O)c1cnc2ccc(-c3c(-c4ccn(C5CC5)n4)nc4occn34)cn12]<br>5-{7-(1-Cyclopropyl-1H-pyrazol-3-yl)-4-thia-1,6-diazabicyclo[3.3.0]octa-2,5,7-trien-8-yl}-1,3a-diaza-3-indenecarboxamide |
| 15 | 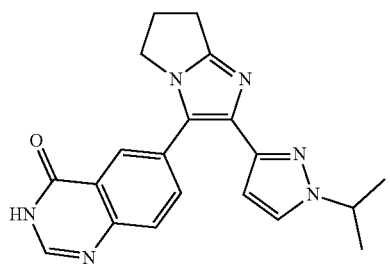 [SMILES: CC(C)n1ccc(-c2nc3n(c2-c2ccc4nc[nH]c(=O)c4c2)CCC3)n1]<br>6-{3-(1-Isopropyl-1H-pyrazol-3-yl)-1,4-diazabicyclo[3.3.0]octa-2,4-dien-2-yl}-3H-quinazolin-4-one |
| 16 | 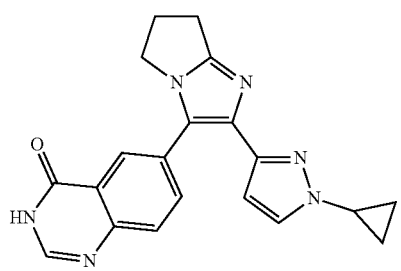 [SMILES: O=c1[nH]cnc2ccc(-c3c(-c4ccn(C5CC5)n4)nc4n3CCC4)cc12]<br>6-{3-(1-Cyclopropyl-1H-pyrazol-3-yl)-1,4-diazabicyclo[3.3.0]octa-2,4-dien-2-yl}-3H-quinazolin-4-one |

TABLE 1-continued

EXEMPLARY COMPOUNDS OF FORMULA (I)

| Compound No. | Structure and Name |
|---|---|
| 17 | 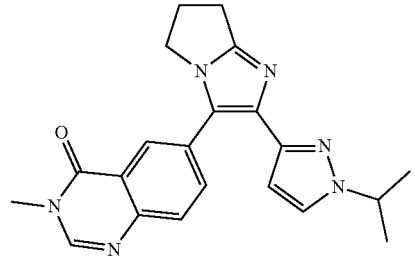 [SMILES: CC(C)n1ccc(-c2nc3n(c2-c2ccc4ncn(C)c(=O)c4c2)CCC3)n1]
6-{3-(1-Isopropyl-1H-pyrazol-3-yl)-1,4-diazabicyclo[3.3.0]octa-2,4-dien-2-yl}-3-methyl-3H-quinazolin-4-one |
| 18 | 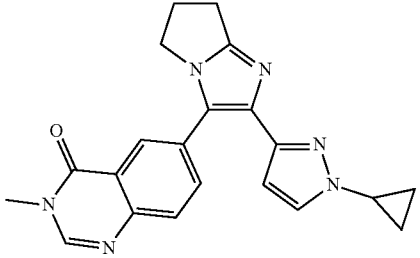 [SMILES: Cn1cnc2ccc(-c3c(-c4ccn(C5CC5)n4)nc4n3CCC4)cc2c1=O]
6-{3-(1-Cyclopropyl-1H-pyrazol-3-yl)-1,4-diazabicyclo[3.3.0]octa-2,4-dien-2-yl}-3-methyl-3H-quinazolin-4-one |
| 19 | 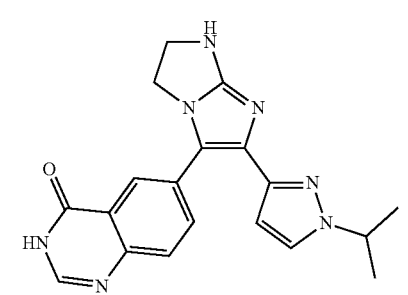
6-{3-(1-Isopropyl-1H-pyrazol-3-yl)-1,4,6-triazabicyclo[3.3.0]octa-2,4-dien-2-yl}-3H-quinazolin-4-one |
| 20 | 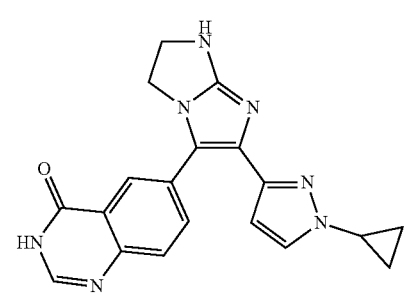 [SMILES: O=c1[nH]cnc2ccc(-c3c(-c4ccn(C5CC5)n4)nc4n3CCN4)cc12]
6-{3-(1-Cyclopropyl-1H-pyrazol-3-yl)-1,4,6-triazabicyclo[3.3.0]octa-2,4-dien-2-yl}-3H-quinazolin-4-one |

TABLE 1-continued

EXEMPLARY COMPOUNDS OF FORMULA (I)

| Compound No. | Structure and Name |
|---|---|
| 21 | 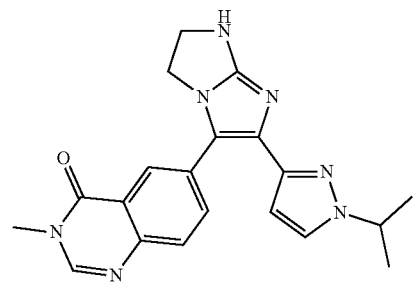 [SMILES: CC(C)n1ccc(-c2nc3n(c2-c2ccc4ncn(C)c(=O)c4c2)CCN3)n1]<br>6-{3-(1-Isopropyl-1H-pyrazol-3-yl)-1,4,6-triazabicyclo[3.3.0]octa-2,4-dien-2-yl}-3-methyl-3H-quinazolin-4-one |
| 22 | 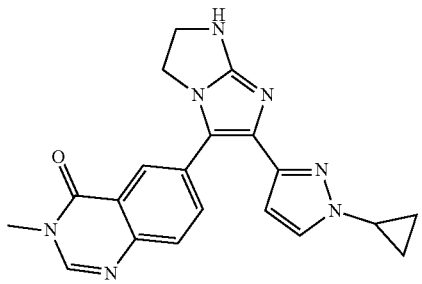 [SMILES: Cn1cnc2ccc(-c3c(-c4ccn(C5CC5)n4)nc4n3CCN4)cc2c1=O]<br>6-{3-(1-Cyclopropyl-1H-pyrazol-3-yl)-1,4,6-triazabicyclo[3.3.0]octa-2,4-dien-2-yl}-3-methyl-3H-quinazolin-4-one |
| 23 | 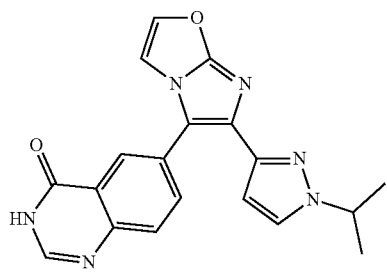 [SMILES: CC(C)n1ccc(-c2nc3occn3c2-c2ccc3nc[nH]c(=O)c3c2)n1]<br>6-{7-(1-Isopropyl-1H-pyrazol-3-yl)-4-oxa-1,6-diazabicyclo[3.3.0]octa-2,5,7-trien-8-yl}-3H-quinazolin-4-one |
| 24 | 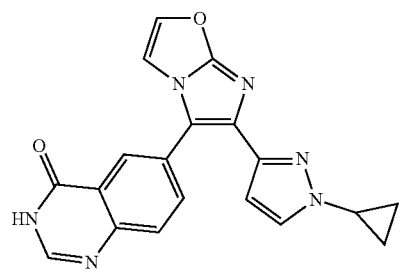 [SMILES: O=c1[nH]cnc2ccc(-c3c(-c4ccn(C5CC5)n4)nc4occn34)cc12]<br>6-{7-(1-Cyclopropyl-1H-pyrazol-3-yl)-4-oxa-1,6-diazabicyclo[3.3.0]octa-2,5,7-trien-8-yl}-3H-quinazolin-4-one |

TABLE 1-continued

EXEMPLARY COMPOUNDS OF FORMULA (I)

| Compound No. | Structure and Name |
|---|---|
| 25 | 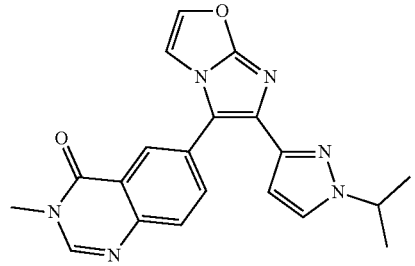 [SMILES: CC(C)n1ccc(-c2nc3occn3c2-c2ccc3ncn(C)c(=O)c3c2)n1]<br>6-{7-(1-Isopropyl-1H-pyrazol-3-yl)-4-oxa-1,6-diazabicyclo[3.3.0]octa-2,5,7-trien-8-yl}-3-methyl-3H-quinazolin-4-one |
| 26 | 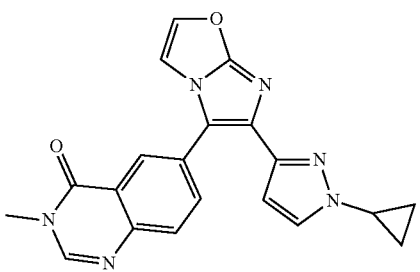 [SMILES: Cn1cnc2ccc(-c3c(-c4ccn(C5CC5)n4)nc4occn34)cc2c1=O]<br>6-{7-(1-Cyclopropyl-1H-pyrazol-3-yl)-4-oxa-1,6-diazabicyclo[3.3.0]octa-2,5,7-trien-8-yl}-3-methyl-3H-quinazolin-4-one |
| 27 | 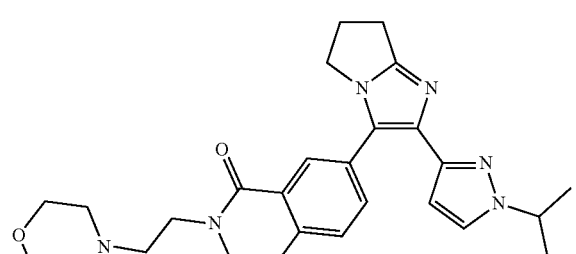<br>6-{3-(1-Isopropyl-1H-pyrazol-3-yl)-1,4-diazabicyclo[3.3.0]octa-2,4-dien-2-yl}-3-(2-morpholinoethyl)-3H-quinazolin-4-one |
| 28 | 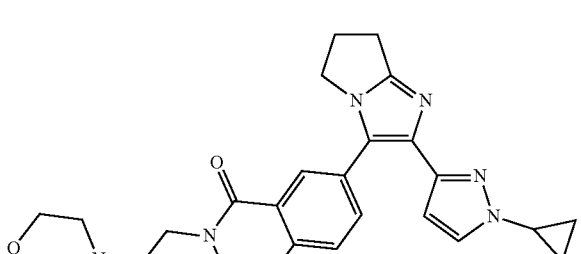<br>6-{3-(1-Cyclopropyl-1H-pyrazol-3-yl)-1,4-diazabicyclo[3.3.0]octa-2,4-dien-2-yl}-3-(2-morpholinoethyl)-3H-quinazolin-4-one |

TABLE 1-continued

EXEMPLARY COMPOUNDS OF FORMULA (I)

| Compound No. | Structure and Name |
|---|---|
| 29 | 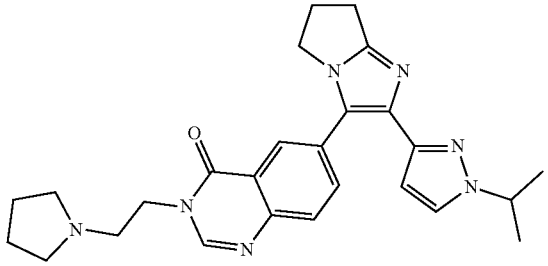 [SMILES: CC(C)n1ccc(-c2nc3n(c2-c2ccc4ncn(CCN5CCCC5)c(=O)c4c2)CCC3)n1]
6-{3-(1-Isopropyl-1H-pyrazol-3-yl)-1,4-diazabicyclo[3.3.0]octa-2,4-dien-2-yl}-3-[2-(1-pyrrolidinyl)ethyl]-3H-quinazolin-4-one |
| 30 | 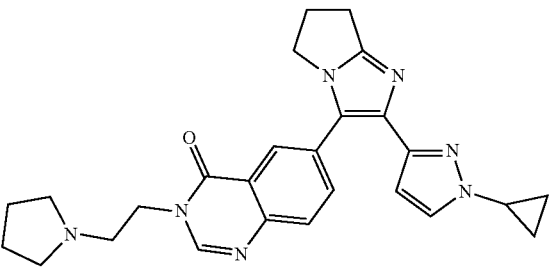 [SMILES: O=c1c2cc(-c3c(-c4ccn(C5CC5)n4)nc4n3CCC4)ccc2ncn1CCN1CCCC1]
6-{3-(1-Cyclopropyl-1H-pyrazol-3-yl)-1,4-diazabicyclo[3.3.0]octa-2,4-dien-2-yl}-3-[2-(1-pyrrolidinyl)ethyl]-3H-quinazolin-4-one |
| 31 | 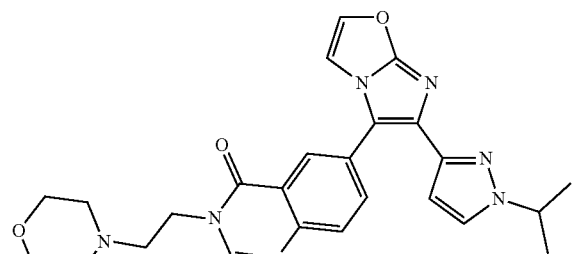
6-{7-(1-Isopropyl-1H-pyrazol-3-yl)-4-oxa-1,6-diazabicyclo[3.3.0]octa-2,5,7-trien-8-yl}-3-(2-morpholinoethyl)-3H-quinazolin-4-one |
| 32 | 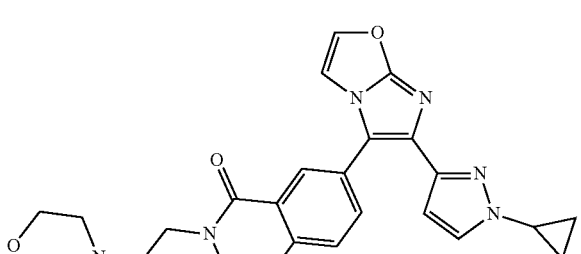
6-{7-(1-Cyclopropyl-1H-pyrazol-3-yl)-4-oxa-1,6-diazabicyclo[3.3.0]octa-2,5,7-trien-8-yl}-3-(2-morpholinoethyl)-3H-quinazolin-4-one |

TABLE 1-continued

EXEMPLARY COMPOUNDS OF FORMULA (I)

| Compound No. | Structure and Name |
|---|---|
| 33 | 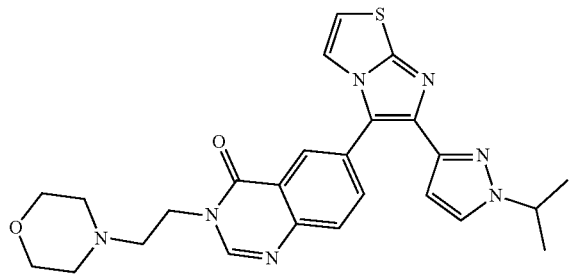<br>6-{7-(1-Isopropyl-1H-pyrazol-3-yl)-4-thia-1,6-diazabicyclo[3.3.0]octa-2,5,7-trien-8-yl}-3-(2-morpholinoethyl)-3H-quinazolin-4-one |
| 34 | 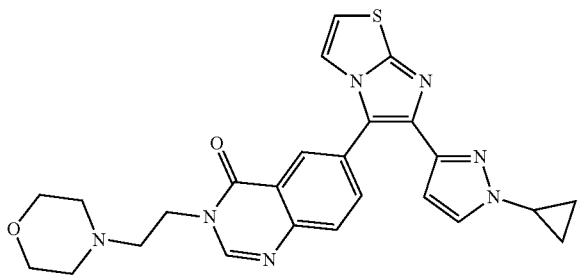 [SMILES: O=c1c2cc(-c3c(-c4ccn(C5CC5)n4)nc4occn34)ccc2ncn1CCN1CCOCC1]<br>6-{7-(1-Cyclopropyl-1H-pyrazol-3-yl)-4-thia-1,6-diazabicyclo[3.3.0]octa-2,5,7-trien-8-yl}-3-(2-morpholinoethyl)-3H-quinazolin-4-one |
| 35 | 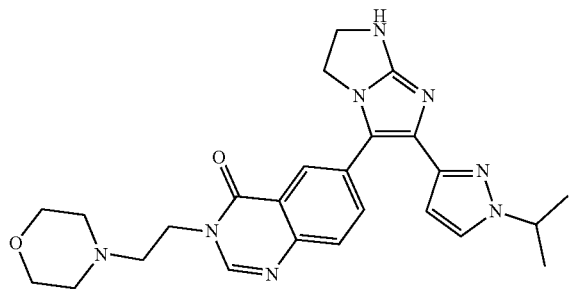 [SMILES: CC(C)n1ccc(-c2nc3n(c2-c2ccc4ncn(CCN5CCOCC5)c(=O)c4c2)CCN3)n1]<br>6-{3-(1-Isopropyl-1H-pyrazol-3-yl)-1,4,6-triazabicyclo[3.3.0]octa-2,4-dien-2-yl}-3-(2-morpholinoethyl)-3H-quinazolin-4-one |
| 36 | 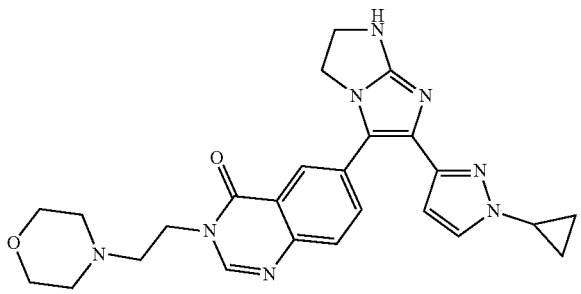 [SMILES: O=c1c2cc(-c3c(-c4ccn(C5CC5)n4)nc4n3CCN4)ccc2ncn1CCN1CCOCC1]<br>6-{3-(1-Cyclopropyl-1H-pyrazol-3-yl)-1,4,6-triazabicyclo[3.3.0]octa-2,4-dien-2-yl}-3-(2-morpholinoethyl)-3H-quinazolin-4-one |

TABLE 1-continued

EXEMPLARY COMPOUNDS OF FORMULA (I)

| Compound No. | Structure and Name |
|---|---|
| 37 | 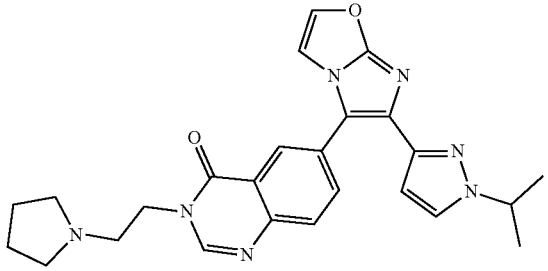 [SMILES: CC(C)n1ccc(-c2nc3occn3c2-c2ccc3ncn(CCN4CCCC4)c(=O)c3c2)n1]<br>6-{7-(1-Isopropyl-1H-pyrazol-3-yl)-4-oxa-1,6-diazabicyclo[3.3.0]octa-2,5,7-trien-8-yl}-3-[2-(1-pyrrolidinyl)ethyl]-3H-quinazolin-4-one |
| 38 | 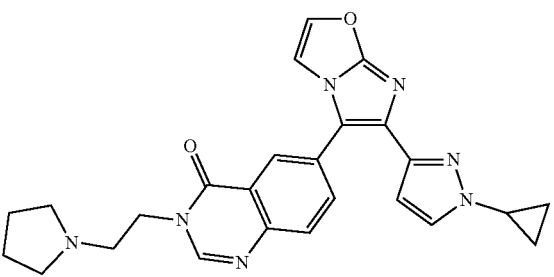 [SMILES: O=c1c2cc(-c3c(-c4ccn(C5CC5)n4)nc4occn34)ccc2ncn1CCN1CCCC1]<br>6-{7-(1-Cyclopropyl-1H-pyrazol-3-yl)-4-oxa-1,6-diazabicyclo[3.3.0]octa-2,5,7-trien-8-yl}-3-[2-(1-pyrrolidinyl)ethyl]-3H-quinazolin-4-one |
| 39 | 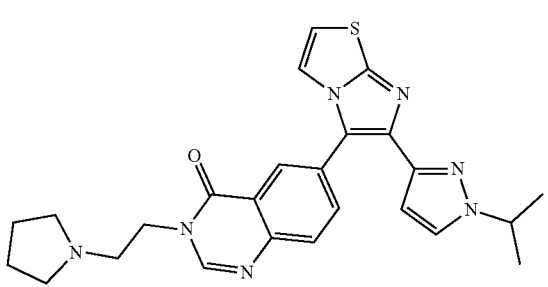<br>6-{7-(1-Isopropyl-1H-pyrazol-3-yl)-4-thia-1,6-diazabicyclo[3.3.0]octa-2,5,7-trien-8-yl}-3-[2-(1-pyrrolidinyl)ethyl]-3H-quinazolin-4-one |
| 40 | 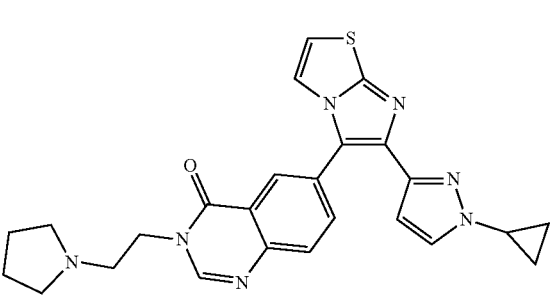 [SMILES: O=c1c2cc(-c3c(-c4ccn(C5CC5)n4)nc4sccn34)ccc2ncn1CCN1CCCC1]<br>6-{7-(1-Cyclopropyl-1H-pyrazol-3-yl)-4-thia-1,6-diazabicyclo[3.3.0]octa-2,5,7-trien-8-yl}-3-[2-(1-pyrrolidinyl)ethyl]-3H-quinazolin-4-one |

TABLE 1-continued

EXEMPLARY COMPOUNDS OF FORMULA (I)

| Compound No. | Structure and Name |
|---|---|
| 41 | 6-{3-(1-Isopropyl-1H-pyrazol-3-yl)-1,4,6-triazabicyclo[3.3.0]octa-2,4-dien-2-yl}-3-[2-(1-pyrrolidinyl)ethyl]-3H-quinazolin-4-one |
| 42 | 6-{3-(1-Cyclopropyl-1H-pyrazol-3-yl)-1,4,6-triazabicyclo[3.3.0]octa-2,4-dien-2-yl}-3-[2-(1-pyrrolidinyl)ethyl]-3H-quinazolin-4-one |
| 43 | 5-{3-(1-Cyclobutyl-1H-pyrazol-3-yl)-1,4-diazabicyclo[3.3.0]octa-2,4-dien-2-yl}-1,3a-diaza-3-indenecarboxamide |
| 44 | 5-{3-(1-Cyclobutyl-1H-pyrazol-3-yl)-1,4,6-triazabicyclo[3.3.0]octa-2,4-dien-2-yl}-1,3a-diaza-3-indenecarboxamide |

TABLE 1-continued

EXEMPLARY COMPOUNDS OF FORMULA (I)

| Compound No. | Structure and Name |
|---|---|
| 45 | 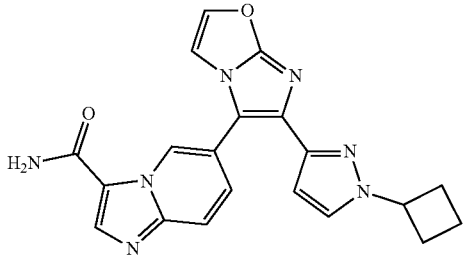<br>5-{7-(1-Cyclobutyl-1H-pyrazol-3-yl)-4-oxa-1,6-diazabicyclo[3.3.0]octa-2,5,7-trien-8-yl}-1,3a-diaza-3-indenecarboxamide |
| 46 | 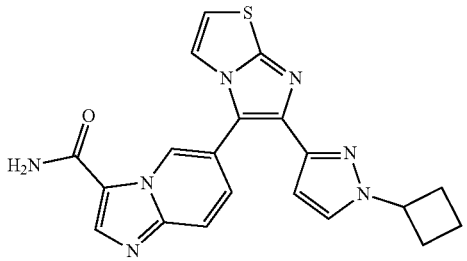 [SMILES: NC(=O)c1cnc2ccc(-c3c(-c4ccn(C5CCC5)n4)nc4occn34)cn12]<br>5-{7-(1-Cyclobutyl-1H-pyrazol-3-yl)-4-thia-1,6-diazabicyclo[3.3.0]octa-2,5,7-trien-8-yl}-1,3a-diaza-3-indenecarboxamide |
| 47 | 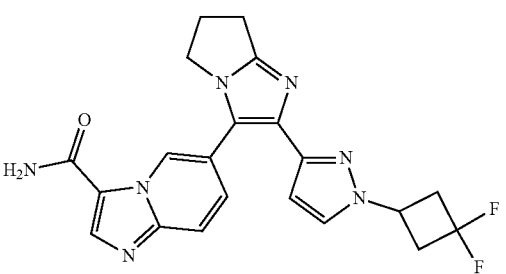 [SMILES: NC(=O)c1cnc2ccc(-c3c(-c4ccn(C5CC(F)(F)C5)n4)nc4n3CCC4)cn12]<br>5-{3-[1-(3,3-Difluorocyclobutyl)-1H-pyrazol-3-yl]-1,4-diazabicyclo[3.3.0]octa-2,4-dien-2-yl}-1,3a-diaza-3-indenecarboxamide |
| 48 | 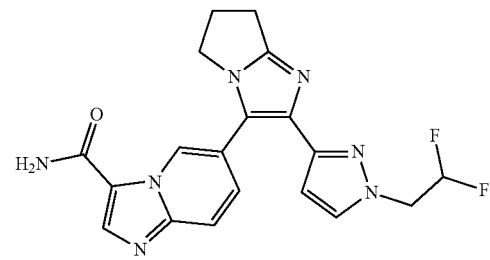 [SMILES: NC(=O)c1cnc2ccc(-c3c(-c4ccn(CC(F)F)n4)nc4n3CCC4)cn12]<br>5-{3-[1-(2,2-Difluoroethyl)-1H-pyrazol-3-yl]-1,4-diazabicyclo[3.3.0]octa-2,4-dien-2-yl}-1,3a-diaza-3-indenecarboxamide |

TABLE 1-continued

EXEMPLARY COMPOUNDS OF FORMULA (I)

| Compound No. | Structure and Name |
|---|---|
| 49 | 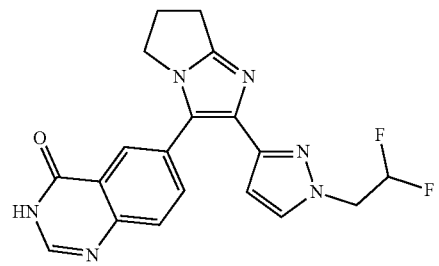 [SMILES: O=c1[nH]cnc2ccc(-c3c(-c4ccn(CC(F)F)n4)nc4n3CCC4)cc12]

6-{3-[1-(2,2-Difluoroethyl)-1H-pyrazol-3-yl]-1,4-diazabicyclo[3.3.0]octa-2,4-dien-2-yl}-3H-quinazolin-4-one |
| 50 | 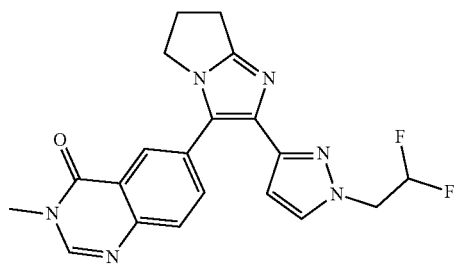 [SMILES: Cn1cnc2ccc(-c3c(-c4ccn(CC(F)F)n4)nc4n3CCC4)cc2c1=O]

6-{3-[1-(2,2-Difluoroethyl)-1H-pyrazol-3-yl]-1,4-diazabicyclo[3.3.0]octa-2,4-dien-2-yl}-3-methyl-3H-quinazolin-4-one |
| 51 | 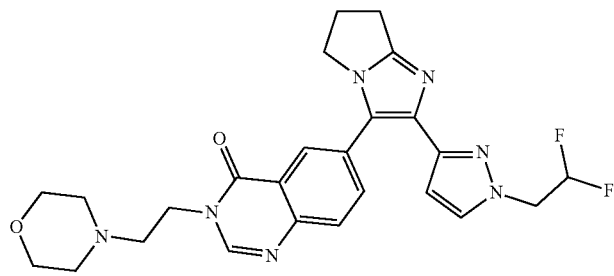 [SMILES: O=c1c2cc(-c3c(-c4ccn(CC(F)F)n4)nc4n3CCC4)ccc2ncn1CCN1CCOCC1]

6-{3-[1-(2,2-Difluoroethyl)-1/-pyrazol-3-yl]-1,4-diazabicyclo[3.3.0]octa-2,4-dien-2-yl}-3-(2-morpholinoethyl)-3H-quinazolin-4-one |
| 52 | 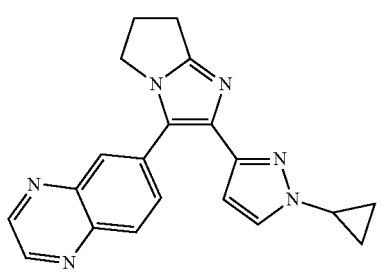 [SMILES: c1cnc2cc(-c3c(-c4ccn(C5CC5)n4)nc4n3CCC4)ccc2n1]

1-Cyclopropyl-3-{2-(6-quinoxalinyl)-1,4-diazabicyclo[3.3.0]octa-2,4-dien-3-yl}-1H-pyrazole |

TABLE 1-continued

EXEMPLARY COMPOUNDS OF FORMULA (I)

| Compound No. | Structure and Name |
|---|---|
| 53 | 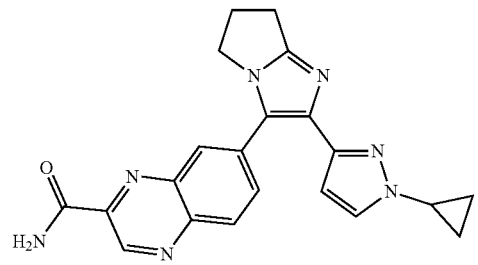 [SMILES: NC(=O)c1cnc2ccc(-c3c(-c4ccn(C5CC5)n4)nc4n3CCC4)cc2n1]<br>7-{3-(1-Cyclopropyl-1H-pyrazol-3-yl)-1,4-diazabicyclo[3.3.0]octa-2,4-dien-2-yl}-2-quinoxalinecarboxamide |
| 54 | 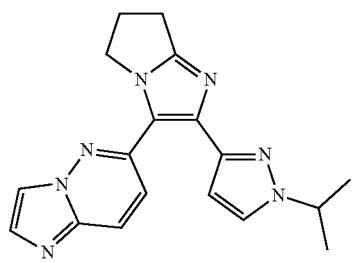 [SMILES: CC(C)n1ccc(-c2nc3n(c2-c2ccc4nccn4n2)CCC3)n1]<br>5-{3-(1-Isopropyl-1H-pyrazol-3-yl)-1,4-diazabicyclo[3.3.0]octa-2,4-dien-2-yl}-1,3a,4-triazaindene |
| 55 | 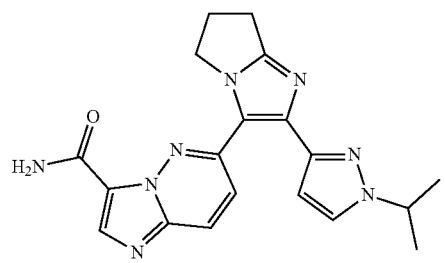 [SMILES: CC(C)n1ccc(-c2nc3n(c2-c2ccc4ncc(C(N)=O)n4n2)CCC3)n1]<br>5-{3-(1-Isopropyl-1H-pyrazol-3-yl)-1,4-diazabicyclo[3.3.0]octa-2,4-dien-2-yl}-1,3a,4-triaza-3-indenecarboxamide |
| 56 | 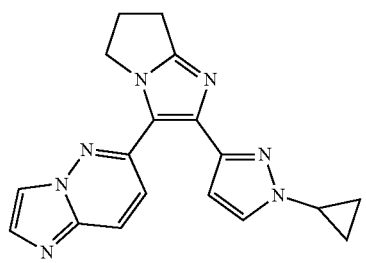 [SMILES: c1cn2nc(-c3c(-c4ccn(C5CC5)n4)nc4n3CCC4)ccc2n1]<br>5-{3-(1-Cyclopropyl-1H-pyrazol-3-yl)-1,4-diazabicyclo[3.3.0]octa-2,4-dien-2-yl}-1,3a,4-triazaindene |

TABLE 1-continued

EXEMPLARY COMPOUNDS OF FORMULA (I)

| Compound No. | Structure and Name |
|---|---|
| 57 | 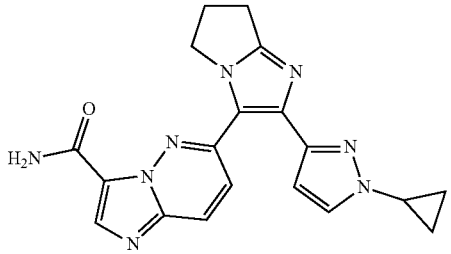

5-{3-(1-Cyclopropyl-1H-pyrazol-3-yl)-1,4-diazabicyclo[3.3.0]octa-2,4-dien-2-yl}-1,3a,4-triaza-3-indenecarboxamide |
| 58 | 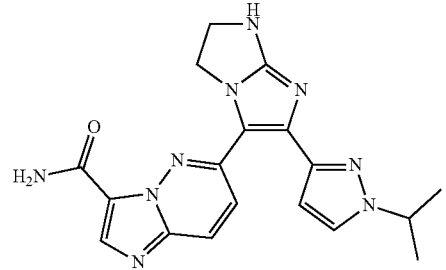 [SMILES: CC(C)n1ccc(-c2nc3n(c2-c2ccc4ncc(C(N)=O)n4n2)CCN3)n1]

5-{3-(1-Isopropyl-1H-pyrazol-3-yl)-1,4,6-triazabicyclo[3.3.0]octa-2,4-dien-2-yl}-1,3a,4-triaza-3-indenecarboxamide |
| 59 | 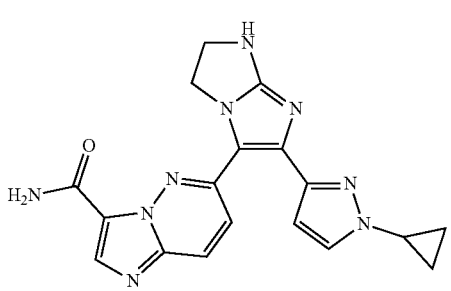 [SMILES: NC(=O)c1cnc2ccc(-c3c(-c4ccn(C5CC5)n4)nc4n3CCN4)nn12]

5-{3-(1-Cyclopropyl-1H-pyrazol-3-yl)-1,4,6-triazabicyclo[3.3.0]octa-2,4-dien-2-yl}-1,3a,4-triaza-3-indenecarboxamide |
| 60 | 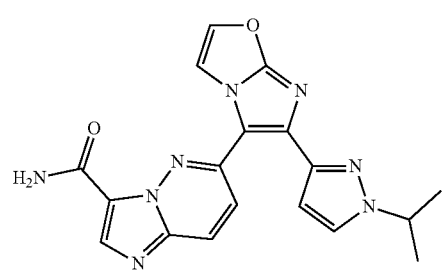

5-{7-(1-Isopropyl-1H-pyrazol-3-yl)-4-oxa-1,6-diazabicyclo[3.3.0]octa-2,5,7-trien-8-yl}-1,3a,4-triaza-3-indenecarboxamide |

TABLE 1-continued

EXEMPLARY COMPOUNDS OF FORMULA (I)

| Compound No. | Structure and Name |
|---|---|
| 61 | 5-{7-(1-Cyclopropyl-1H-pyrazol-3-yl)-4-oxa-1,6-diazabicyclo[3.3.0]octa-2,5,7-trien-8-yl}-1,3a,4-triaza-3-indenecarboxamide |
| 62 | 5-{7-(1-Isopropyl-1H-pyrazol-3-yl)-4-thia-1,6-diazabicyclo[3.3.0]octa-2,5,7-trien-8-yl}-1,3a,4-triaza-3-indenecarboxamide |
| 63 | 5-{7-(1-Cyclopropyl-1H-pyrazol-3-yl)-4-thia-1,6-diazabicyclo[3.3.0]octa-2,5,7-trien-8-yl}-1,3a,4-triaza-3-indenecarboxamide |
| 64 | 1-(5-(Imidazo[1,2-a]pyridin-6-yl)-6-(1-isopropyl-1H-pyrazol-3-yl)-2,3-dihydro-1H-imidazo[1,2-a]imidazol-1-yl)ethan-1-one |

TABLE 1-continued
EXEMPLARY COMPOUNDS OF FORMULA (I)
| Compound No. | Structure and Name |
| --- | --- |
65
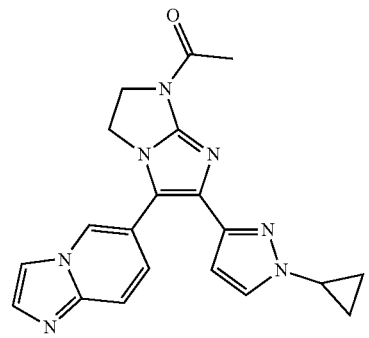 [SMILES: CC(=O)N1CCn2c1nc(-c1ccn(C3CC3)n1)c2-c1ccc2nccn2c1]
1-(6-(1-Cyclopropyl-1H-pyrazol-3-yl)-5-(imidazo[1,2-a]pyridin-6-yl)-2,3-dihydro-1H-imidazo[1,2-a]imidazol-1-yl)ethan-1-one
66
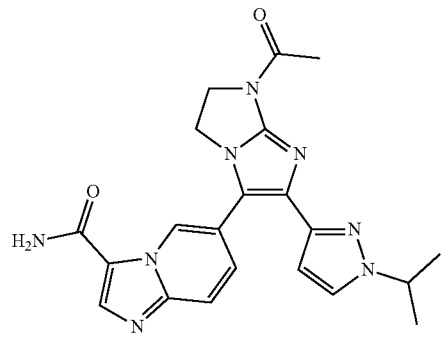 [SMILES: CC(=O)N1CCn2c1nc(-c1ccn(C(C)C)n1)c2-c1ccc2ncc(C(N)=O)n2c1]
6-(1-Acetyl-6-(1-isopropyl-1H-pyrazol-3-yl)-2,3-dihydro-1H-imidazo[1,2-a]imidazol-5-yl)imidazo[1,2-a]pyridine-3-carboxamide
67
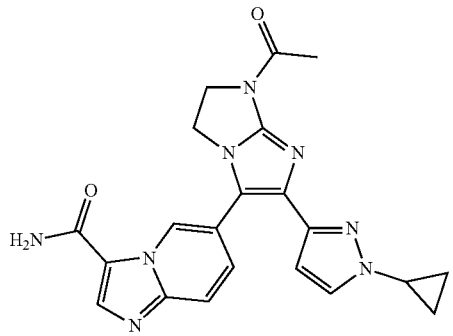 [SMILES: CC(=O)N1CCn2c1nc(-c1ccn(C3CC3)n1)c2-c1ccc2ncc(C(N)=O)n2c1]
5-{6-Acetyl-3-(1-cyclopropyl-1H-pyrazol-3-yl)-1,4,6-triazabicyclo[3.3.0]octa-2,4-dien-2-yl}-1,3a-diaza-3-indenecarboxamide TABLE 1-continued
EXEMPLARY COMPOUNDS OF FORMULA (I)
| Compound No. | Structure and Name |
| --- | --- |
| 68 | 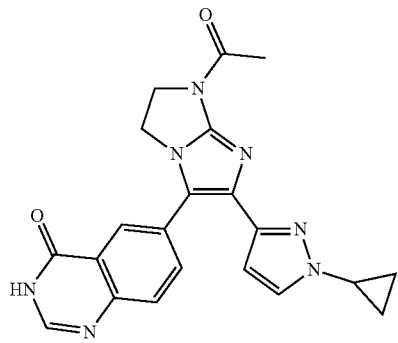 [SMILES: CC(=O)N1CCn2c1nc(-c1ccn(C3CC3)n1)c2-c1ccc2nc[nH]c(=O)c2c1]<br>7-(1-Acetyl-6-(1-cyclopropyl-1H-pyrazol-3-yl)-2,3-dihydro-1H-imidazo[1,2-a]imidazol-5-yl)isoquinolin-1(2H)-one |
| 69 | 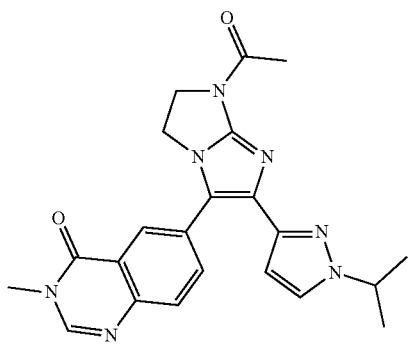 [SMILES: CC(=O)N1CCn2c1nc(-c1ccn(C(C)C)n1)c2-c1ccc2ncn(C)c(=O)c2c1]<br>6-(1-Acetyl-6-(1-isopropyl-1H-pyrazol-3-yl)-2,3-dihydro-1H-imidazo[1,2-a]imidazol-5-yl)-3-methylquinazolin-4(3H)-one |
| 70 | 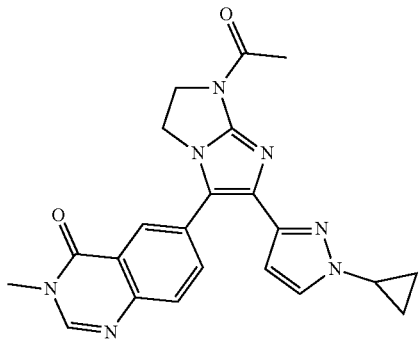 [SMILES: CC(=O)N1CCn2c1nc(-c1ccn(C3CC3)n1)c2-c1ccc2ncn(C)c(=O)c2c1]<br>6-(1-Acetyl-6-(1-cyclopropyl-1H-pyrazol-3-yl)-2,3-dihydro-1H-imidazo[1,2-a]imidazol-5-yl)-3-methylquinazolin-4(3H)-one |

TABLE 1-continued

EXEMPLARY COMPOUNDS OF FORMULA (I)

| Compound No. | Structure and Name |
|---|---|
| 71 | 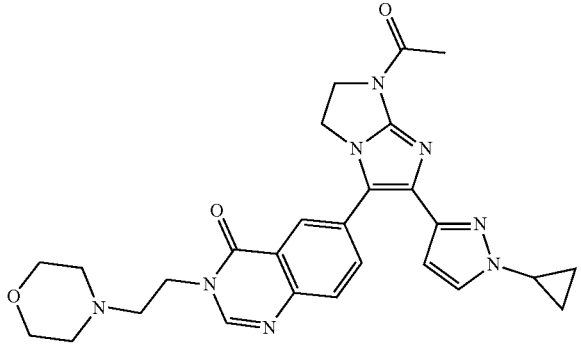 [SMILES: CC(=O)N1CCn2c1nc(-c1ccn(C3CC3)n1)c2-c1ccc2ncn(CCN3CCOCC3)c(=O)c2c1]<br>6-(1-Acetyl-6-(1-cyclopropyl-1H-pyrazol-3-yl)-2,3-dihydro-1H-imidazo[1,2-a]imidazol-5-yl)-3-(2-morpholinoethyl)quinazolin-4(3H)-one |
| 72 | 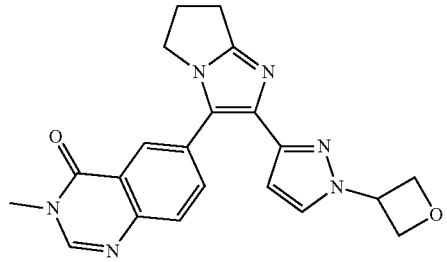 [SMILES: Cn1cnc2ccc(-c3c(-c4ccn(C5COC5)n4)nc4n3CCC4)cc2c1=O]<br>3-Methyl-6-(2-(1-(oxetan-3-yl)-1H-pyrazol-3-yl)-6,7-dihydro-5H-pyrrolo[1,2-a]imidazol-3-yl)quinazolin-4(3H)-one |
| 73 | 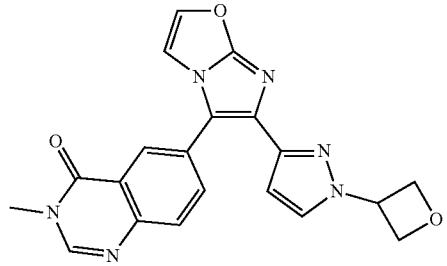 [SMILES: Cn1cnc2ccc(-c3c(-c4ccn(C5COC5)n4)nc4occn34)cc2c1=O]<br>3-Methyl-6-(6-(1-(oxetan-3-yl)-1H-pyrazol-3-yl)imidazo[2,1-b]oxazol-5-yl)quinazolin-4(3H)-one |
| 74 | 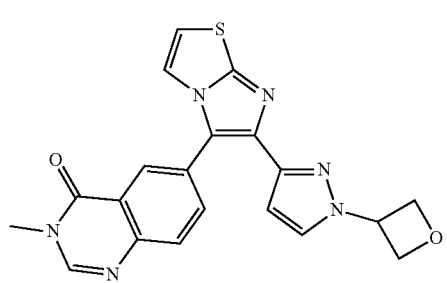<br>3-Methyl-6-(6-(1-(oxetan-3-yl)-1H-pyrazol-3-yl)imidazo[2,1-b]thiazol-5-yl)quinazolin-4(3H)-one |

TABLE 1-continued

EXEMPLARY COMPOUNDS OF FORMULA (I)

| Compound No. | Structure and Name |
|---|---|
| 75 | 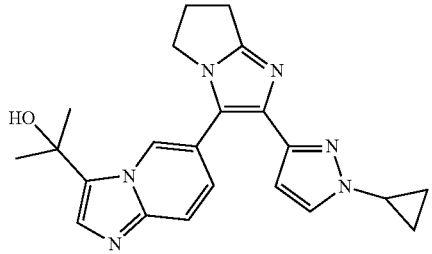 [SMILES: CC(C)(O)c1cnc2ccc(-c3c(-c4ccn(C5CC5)n4)nc4n3CCC4)cn12]
2-(6-(2-(1-Cyclopropyl-1H-pyrazol-3-yl)-6,7-dihydro-5H-pyrrolo[1,2-a]imidazol-3-yl)imidazo[1,2-a]pyridin-3-yl)propan-2-ol |
| 76 | 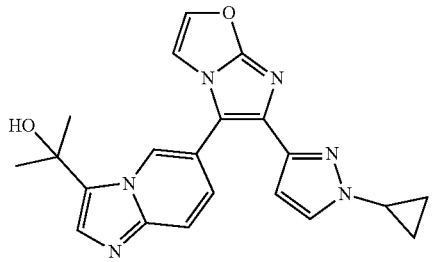 [SMILES: CC(C)(O)c1cnc2ccc(-c3c(-c4ccn(C5CC5)n4)nc4occn34)cn12]
2-(6-(6-(1-Cyclopropyl-1H-pyrazol-3-yl)imidazo[2,1-b]oxazol-5-yl)imidazo[1,2-a]pyridin-3-yl)propan-2-ol |
| 77 | 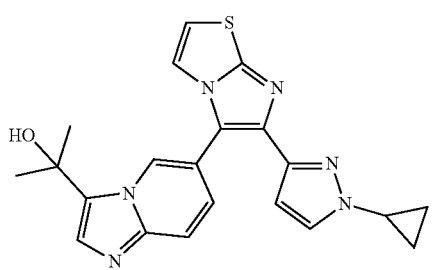
2-(6-(6-(1-Cyclopropyl-1H-pyrazol-3-yl)imidazo[2,1-b]thiazol-5-yl)imidazo[1,2-a]pyridin-3-yl)propan-2-ol |
| 78 | 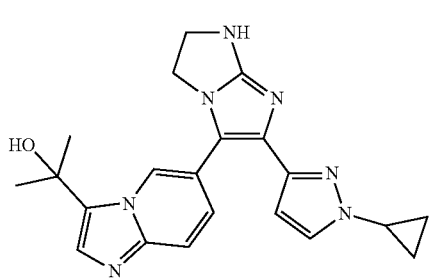 [SMILES: CC(C)(O)c1cnc2ccc(-c3c(-c4ccn(C5CC5)n4)nc4n3CCN4)cn12]
2-(6-(6-(1-Cyclopropyl-1H-pyrazol-3-yl)-2,3-dihydro-1H-imidazo[1,2-a]imidazol-5-yl)imidazo[1,2-a]pyridin-3-yl)propan-2-ol |

TABLE 1-continued

EXEMPLARY COMPOUNDS OF FORMULA (I)

| Compound No. | Structure and Name |
|---|---|
| 79 | 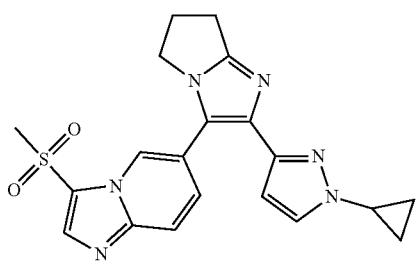 [SMILES: CS(=O)(=O)c1cnc2ccc(-c3c(-c4ccn(C5CC5)n4)nc4n3CCC4)cn12]
6-(2-(1-Cyclopropyl-1H-pyrazol-3-yl)-6,7-dihydro-5H-pyrrolo[1,2-a]imidazol-3-yl)-3-(methylsulfonyl)imidazo[1,2-a]pyridine |
| 80 | 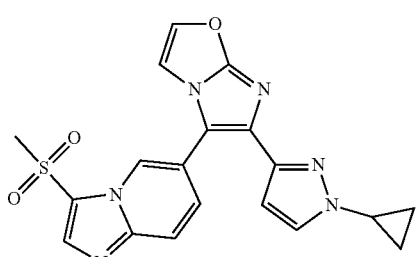
6-(1-Cyclopropyl-1H-pyrazol-3-yl)-5-(3-(methylsulfonyl)imidazo[1,2-a]pyridin-6-yl)imidazo[2,1b]oxazole |
| 81 | 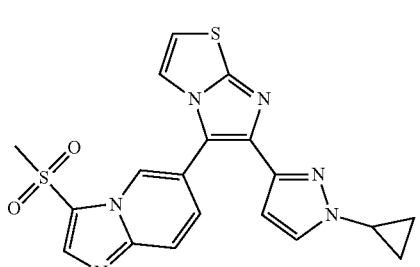
6-(1-Cyclopropyl-1H-pyrazol-3-yl)-5-(3-(methylsulfonyl)imidazo[1,2-a]pyridin-6-yl)imidazo[2,1b]thiazole |
| 82 | 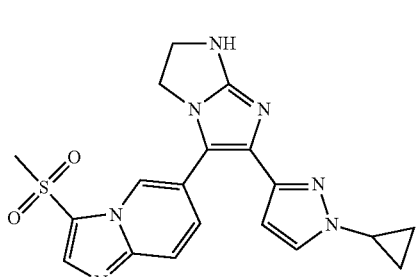
6-(6-(1-Cyclopropyl-1H-pyrazol-3-yl)-2,3-dihydro-1H-imidazo[1,2-a]imidazol-5-yl)-3-(methylsulfonyl)imidazo[1,2-a]pyridine |

TABLE 1-continued

EXEMPLARY COMPOUNDS OF FORMULA (I)

| Compound No. | Structure and Name |
|---|---|
| 83 | 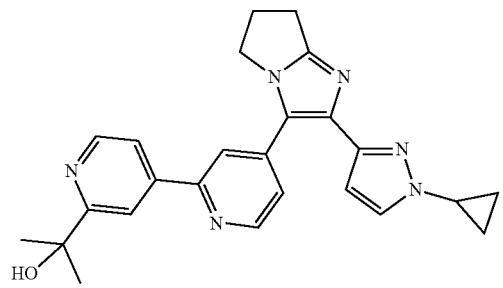 [SMILES: CC(C)(O)c1cc(-c2cc(-c3c(-c4ccn(C5CC5)n4)nc4n3CCC4)ccn2)ccn1]

2-(4-(2-(1-Cyclopropyl-1H-pyrazol-3-yl)-6,7-dihydro-5H-pyrrolo[1,2-a]imidazol-3-yl)-[2,4'-bipyridin]-2'-yl)propan-2-ol |
| 84 | 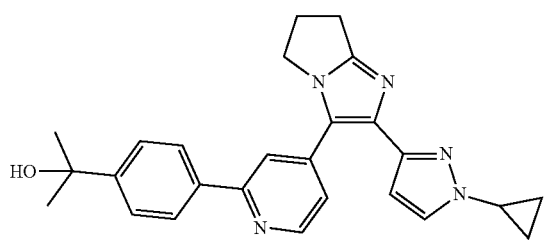 [SMILES: CC(C)(O)c1ccc(-c2cc(-c3c(-c4ccn(C5CC5)n4)nc4n3CCC4)ccn2)cc1]

2-(4-(4-(2-(1-Cyclopropyl-1H-pyrazol-3-yl)-6,7-dihydro-5H-pyrrolo[1,2-a]imidazol-3-yl)pyridin-2-yl)phenyl)propan-2-ol |
| 85 | 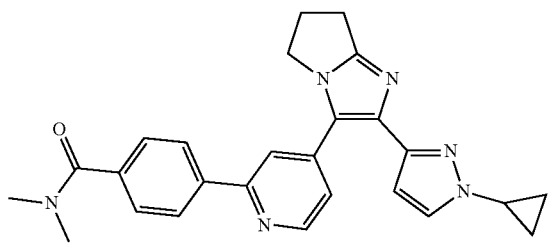 [SMILES: CN(C)C(=O)c1ccc(-c2cc(-c3c(-c4ccn(C5CC5)n4)nc4n3CCC4)ccn2)cc1]

4-(4-(2-(1-Cyclopropyl-1H-pyrazol-3-yl)-6,7-dihydro-5H-pyrrolo[1,2-a]imidazol-3-yl)pyridin-2-yl)-N,N-dimethylbenzamide |
| 86 | 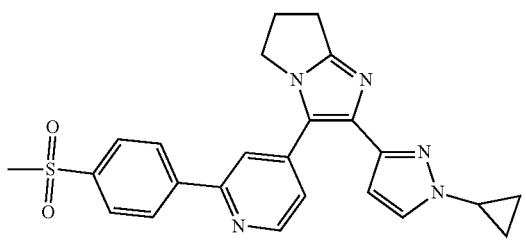 [SMILES: CS(=O)(=O)c1ccc(-c2cc(-c3c(-c4ccn(C5CC5)n4)nc4n3CCC4)ccn2)cc1]

2-(1-Cyclopropyl-1H-pyrazol-3-yl)-3-(2-(4-(methylsulfonyl)phenyl)pyridin-4-yl)-6,7-dihydro-5H-pyrrolo[1,2-a]imidazole |

TABLE 1-continued

EXEMPLARY COMPOUNDS OF FORMULA (I)

| Compound No. | Structure and Name |
|---|---|
| 87 | 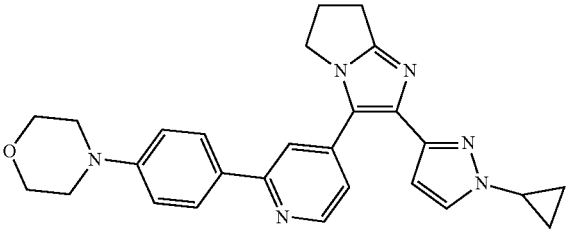 [SMILES: c1cc(-c2c(-c3ccn(C4CC4)n3)nc3n2CCC3)cc(-c2ccc(N3CCOCC3)cc2)n1]  4-(4-(4-(2-(1-Cyclopropyl-1H-pyrazol-3-yl)-6,7-dihydro-5H-pyrrolo[1,2-a]imidazol-3-yl)pyridin-2-yl)phenyl)morpholine |
| 88 | 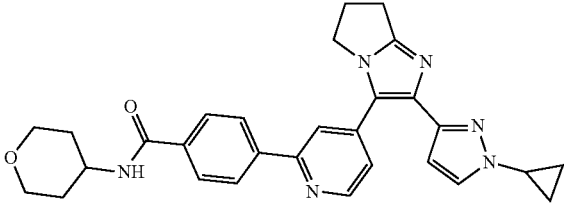 [SMILES: O=C(NC1CCOCC1)c1ccc(-c2cc(-c3c(-c4ccn(C5CC5)n4)nc4n3CCC4)ccn2)cc1]  4-(4-(2-(1-Cyclopropyl-1H-pyrazol-3-yl)-6,7-dihydro-5H-pyrrolo[1,2-a]imidazol-3-yl)pyridin-2-yl)-N-(tetrahydro-2H-pyran-4-yl)benzamide |
| 89 | 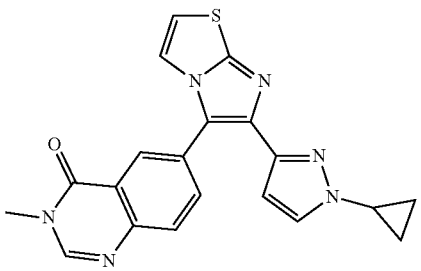 [SMILES: Cn1cnc2ccc(-c3c(-c4ccn(C5CC5)n4)nc4sccn34)cc2c1=O]  6-{7-(1-Cyclopropyl-1H-pyrazol-3-yl)-4-thia-1,6-diazabicyclo[3.3.0]octa-2,5,7-trien-8-yl}-3-methyl-3H-quinazolin-4-one |
| 90 | 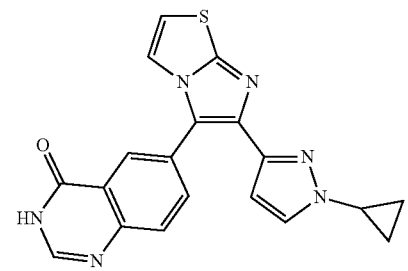 [SMILES: O=c1[nH]cnc2ccc(-c3c(-c4ccn(C5CC5)n4)nc4sccn34)cc12]  6-{7-(1-Cyclopropyl-1H-pyrazol-3-yl)-4-thia-1,6-diazabicyclo[3.3.0]octa-2,5,7-trien-8-yl}-3H-quinazolin-4-one |

TABLE 1-continued

EXEMPLARY COMPOUNDS OF FORMULA (I)

| Compound No. | Structure and Name |
|---|---|
| 91 | 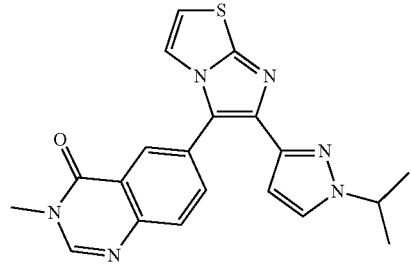 [SMILES: CC(C)n1ccc(-c2nc3sccn3c2-c2ccc3ncn(C)c(=O)c3c2)n1]<br>6-(6-(1-Isopropyl-1H-pyrazol-3-yl)imidazo[2,1-b]thiazol-5-yl)-3-methylquinazolin-4(3H)-one |
| 92 | 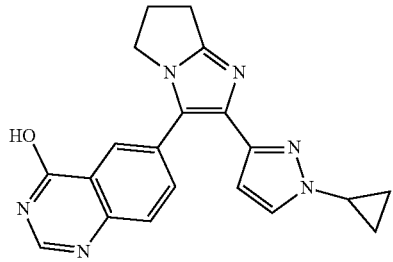 [SMILES: Oc1ncnc2ccc(-c3c(-c4ccn(C5CC5)n4)nc4n3CCC4)cc12]<br>6-(2-(1-Cyclopropyl-1H-pyrazol-3-yl)-6,7-dihydro-5H-pyrrolo[1,2-a]imidazol-3-yl)quinazolin-4-ol |
| 93 | 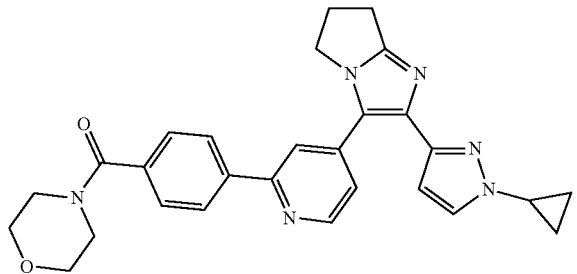 [SMILES: O=C(c1ccc(-c2cc(-c3c(-c4ccn(C5CC5)n4)nc4n3CCC4)ccn2)cc1)N1CCOCC1]<br>(4-(4-(2-(1-Cyclopropyl-1H-pyrazol-3-yl)-6,7-dihydro-5H-pyrrolo[1,2-a]imidazol-3-yl)pyridin-2-yl)phenyl)(morpholino)methanone |
| 94 | 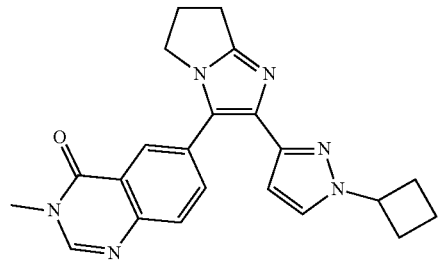 [SMILES: Cn1cnc2ccc(-c3c(-c4ccn(C5CCC5)n4)nc4n3CCC4)cc2c1=O]<br>6-(2-(1-Cyclobutyl-1H-pyrazol-3-yl)-6,7-dihydro-5H-pyrrolo[1,2-a]imidazol-3-yl)-3-methylquinazolin-4(3H)-one |

TABLE 1-continued

EXEMPLARY COMPOUNDS OF FORMULA (I)

| Compound No. | Structure and Name |
|---|---|
| 95 | 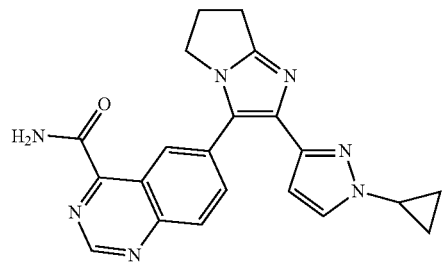 [SMILES: NC(=O)c1ncnc2ccc(-c3c(-c4ccn(C5CC5)n4)nc4n3CCC4)cc12]<br>6-(2-(1-Cyclopropyl-1H-pyrazol-3-yl)-6,7-dihydro-5H-pyrrolo[1,2-a]imidazol-3-yl)quinazoline-4-carboxamide |
| 96 | 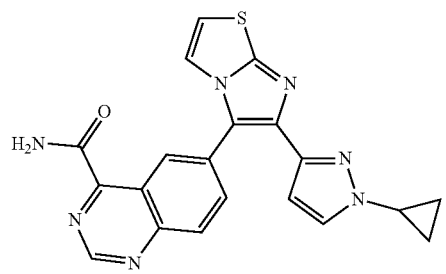 [SMILES: NC(=O)c1ncnc2ccc(-c3c(-c4ccn(C5CC5)n4)nc4sccn34)cc12]<br>6-(6-(1-Cyclopropyl-1H-pyrazol-3-yl)imidazo[2,1-b]thiazol-5-yl)quinazoline-4-carboxamide |
| 97 | 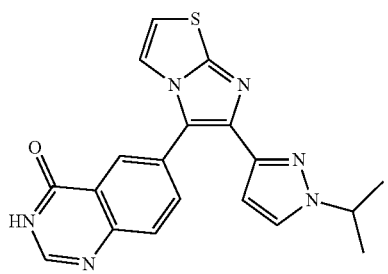<br>6-(6-(1-Isopropyl-1H-pyrazol-3-yl)imidazo[2,1-b]thiazol-5-yl)quinazolin-4(3H)-one hydrochloride |
| 98 | 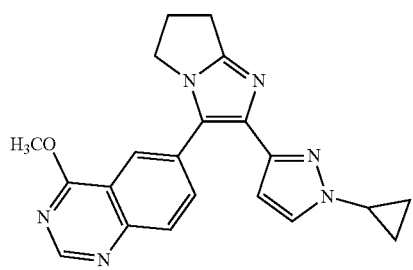 [SMILES: COc1ncnc2ccc(-c3c(-c4ccn(C5CC5)n4)nc4n3CCC4)cc12]<br>6-(2-(1-Cyclopropyl-1H-pyrazol-3-yl)-6,7-dihydro-5H-pyrrolo[1,2-a]imidazol-3-yl)-4-methoxyquinazoline |

TABLE 1-continued

EXEMPLARY COMPOUNDS OF FORMULA (I)

| Compound No. | Structure and Name |
|---|---|
| 99 | 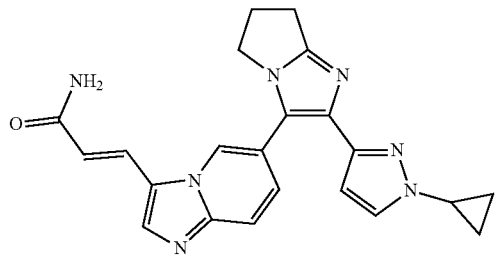 [SMILES: NC(=O)/C=C/c1cnc2ccc(-c3c(-c4ccn(C5CC5)n4)nc4n3CCC4)cn12]<br>(E)-3-(5-{3-(1-Cyclopropyl-1H-pyrazol-3-yl)-1,4-diazabicyclo[3.3.0]octa-2,4-dien-2-yl}-1,3a-diaza-4-indenyl)acrylamide |
| 100 | 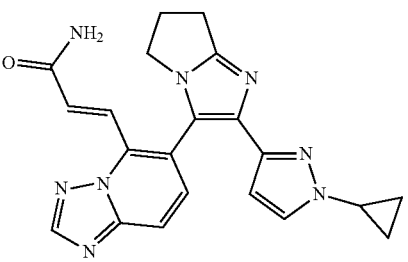 [SMILES: NC(=O)/C=C/c1c(-c2c(-c3ccn(C4CC4)n3)nc3n2CCC3)ccc2ncnn12]<br>(E)-3-(5-{3-(1-Cyclopropyl-1H-pyrazol-3-yl)-1,4-diazabicyclo[3.3.0]octa-2,4-dien-2-yl}-1,3,3a-triaza-4-indenyl)acrylamide |
| 101 | 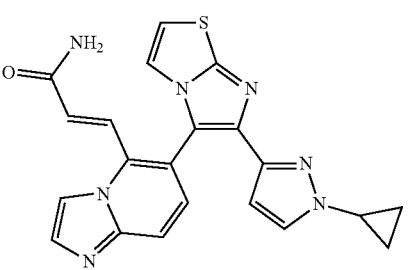 [SMILES: NC(=O)/C=C/c1c(-c2c(-c3ccn(C4CC4)n3)nc3sccn23)ccc2nccn12]<br>(E)-3-(5-{7-(1-Cyclopropyl-1/-pyrazol-3-yl)-4-thia-1,6-diazabicyclo[3.3.0]octa-2,5,7-trien-8-yl}-1,3a-diaza-4-indenyl)acrylamide |
| 102 | 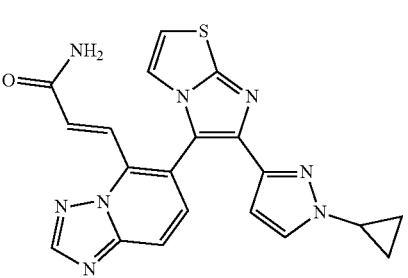<br>(E)-3-(5-{7-(1-Cyclopropyl-1H-pyrazol-3-yl)-4-thia-1,6-diazabicyclo[3.3.0]octa-2,5,7-trien-8-yl}-1,3,3a-triaza-4-indenyl)acrylamide |

TABLE 1-continued

EXEMPLARY COMPOUNDS OF FORMULA (I)

| Compound No. | Structure and Name |
|---|---|
| 103 | 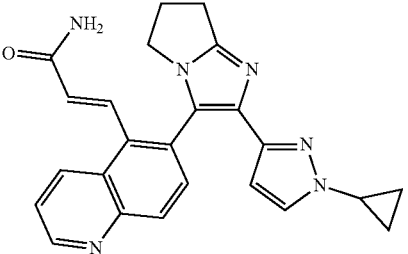 [SMILES: NC(=O)/C=C/c1c(-c2c(-c3ccn(C4CC4)n3)nc3n2CCC3)ccc2ncccc12]<br>E)-3-(6-{3-(1-Cyclopropyl-1H-pyrazol-3-yl)-1,4-diazabicyclo[3.3.0]octa-2,4-dien-2-yl}-5-quinolyl)acrylamide |
| 104 | 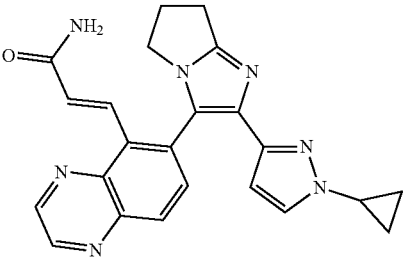 [SMILES: NC(=O)/C=C/c1c(-c2c(-c3ccn(C4CC4)n3)nc3n2CCC3)ccc2nccnc12]<br>(E)-3-(6-{3-(1-Cyclopropyl-1H-pyrazol-3-yl)-1,4-diazabicyclo[3.3.0]octa-2,4-dien-2-yl}-5-quinoxalinyl)acrylamide |
| 105 | 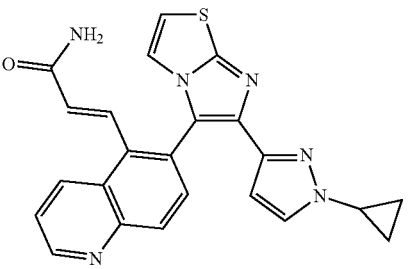 [SMILES: NC(=O)/C=C/c1c(-c2c(-c3ccn(C4CC4)n3)nc3sccn23)ccc2ncccc12]<br>(E)-3-(6-{7-(1-Cyclopropyl-1H-pyrazol-3-yl)-4-thia-1,6-diazabicyclo[3.3.0]octa-2,5,7-trien-8-yl}-5-quinolyl)acrylamide |
| 106 | 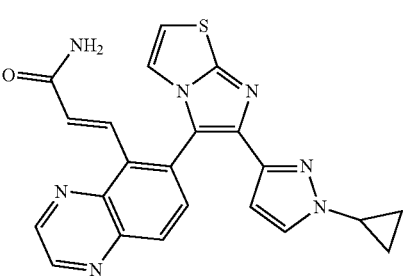 [SMILES: NC(=O)/C=C/c1c(-c2c(-c3ccn(C4CC4)n3)nc3sccn23)ccc2nccnc12]<br>(E)-3-(6-{7-(1-Cyclopropyl-1H-pyrazol-3-yl)-4-thia-1,6-diazabicyclo[3.3.0]octa-2,5,7-trien-8-yl}-5-quinoxalinyl)acrylamide |

TABLE 1-continued

EXEMPLARY COMPOUNDS OF FORMULA (I)

| Compound No. | Structure and Name |
|---|---|
| 107 | 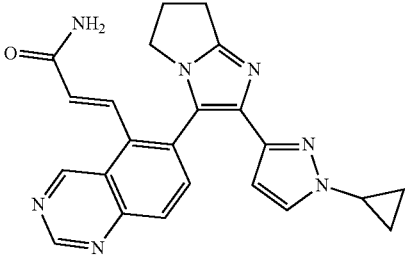 [SMILES: NC(=O)/C=C/c1c(-c2c(-c3ccn(C4CC4)n3)nc3n2CCC3)ccc2ncncc12]

(E)-3-(6-{3-(1-Cyclopropyl-1H-pyrazol-3-yl)-1,4-diazabicyclo[3.3.0]octa-2,4-dien-2-yl}-5-quinazolinyl)acrylamide |
| 108 | 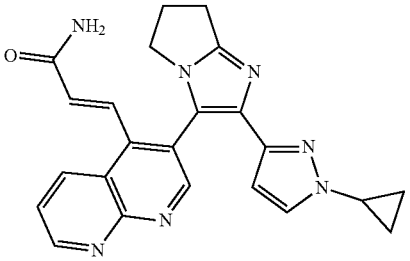 [SMILES: NC(=O)/C=C/c1c(-c2c(-c3ccn(C4CC4)n3)nc3n2CCC3)cnc2ncccc12]

(E)-3-(3-{3-(1-Cyclopropyl-1H-pyrazol-3-yl)-1,4-diazabicyclo[3.3.0]octa-2,4-dien-2-yl}-1,8-diaza-4-naphthyl)acrylamide |
| 109 | 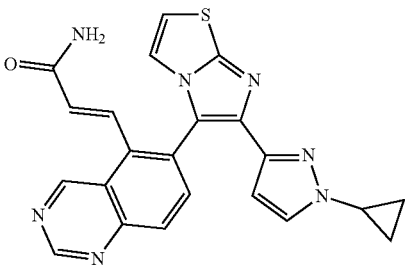 [SMILES: NC(=O)/C=C/c1c(-c2c(-c3ccn(C4CC4)n3)nc3sccn23)ccc2ncncc12]

(E)-3-(6-{7-(1-Cyclopropyl-1H-pyrazol-3-yl)-4-thia-1,6-diazabicyclo[3.3.0]octa-2,5,7-trien-8-yl}-5-quinazolinyl)acrylamide |
| 110 | 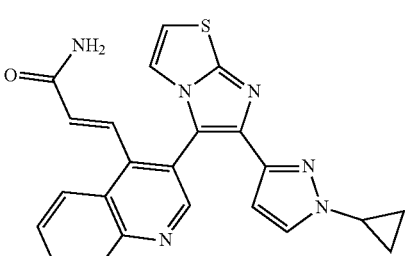

(E)-3-(3-{7-(1-Cyclopropyl-1H-pyrazol-3-yl)-4-thia-1,6-diazabicyclo[3.3.0]octa-2,5,7-trien-8-yl}-1,8-diaza-4-naphthyl)acrylamide |

TABLE 1-continued

EXEMPLARY COMPOUNDS OF FORMULA (I)

| Compound No. | Structure and Name |
|---|---|
| 111 | (E)-3-(5-{7-(1-Cyclopropyl-1H-pyrazol-3-yl)-4-oxa-1,6-diazabicyclo[3.3.0]octa-2,5,7-trien-8-yl}-1,3a-diaza-4-indenyl)acrylamide |
| 112 | (E)-3-(5-{7-(1-Cyclopropyl-1H-pyrazol-3-yl)-4-oxa-1,6-diazabicyclo[3.3.0]octa-2,5,7-trien-8-yl}-1,3,3a-triaza-4-indenyl)acrylamide |
| 113 | (E)-3-(6-{7-(1-Cyclopropyl-1H-pyrazol-3-yl)-4-oxa-1,6-diazabicyclo[3.3.0]octa-2,5,7-trien-8-yl}-5-quinolyl)acrylamide |
| 114 | (E)-3-(6-{7-(1-Cyclopropyl-1H-pyrazol-3-yl)-4-oxa-1,6-diazabicyclo[3.3.0]octa-2,5,7-trien-8-yl}-5-quinoxalinyl)acrylamide |

TABLE 1-continued

EXEMPLARY COMPOUNDS OF FORMULA (I)

| Compound No. | Structure and Name |
|---|---|
| 115 | 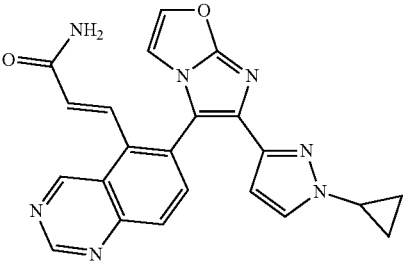 [SMILES: NC(=O)/C=C/c1c(-c2c(-c3ccn(C4CC4)n3)nc3occn23)ccc2ncncc12]<br>(E)-3-(6-{7-(1-Cyclopropyl-1H-pyrazol-3-yl)-4-oxa-1,6-diazabicyclo[3.3.0]octa-2,5,7-trien-8-yl}-5-quinazolinyl)acrylamide |
| 116 | 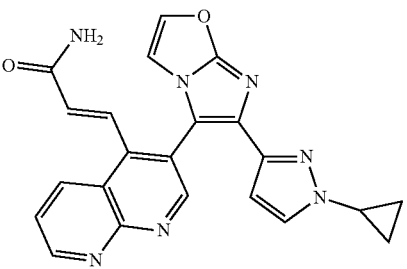 [SMILES: NC(=O)/C=C/c1c(-c2c(-c3ccn(C4CC4)n3)nc3occn23)cnc2ncccc12]<br>(E)-3-(3-{7-(1-Cyclopropyl-1H-pyrazol-3-yl)-4-oxa-1,6-diazabicyclo[3.3.0]octa-2,5,7-trien-8-yl}-1,8-diaza-4-naphthyl)acrylamide |

It will be recognized by one skilled in the art that basic nitrogen atoms present in the compounds disclosed herein may be combined with organic or inorganic acids resulting in the formation of salts. Some embodiments encompass an ALK5 inhibitor as described above that is a derivative or a pharmaceutically acceptable salt thereof as the active biological agent. In addition, solvates comprised of either organic or inorganic solvents may also be prepared and found to be pharmaceutically acceptable or even preferable. Many of the compounds disclosed herein, whether as salts or free bases, may exist in one or more crystalline forms. Such polymorphic forms may have differing properties regarding, but not limited to, absorption, solubility, and stability, one or more of which may be pharmaceutically acceptable or even preferable.

In the case of ALK5 inhibitors that are to be administered orally, blending of the active ingredient with pharmaceutically acceptable carriers (e.g. excipients, disintegrants, binders, colorants, flavorings, emulsifiers, coatings, etc.), diluents, or solubilizing agents may provide a finished pharmaceutical product in the form of tablets, granules, powders, capsules, suspensions, syrups, or solutions, some of which may be designed for either quick release or timed release of the active drug agent. Similar or different formulations may be used for compounds specified for delivery via an intravenous, pulmonary, intramuscular route, or via suppository. One skilled in the art—with the aid of this disclosure-will also appreciate that drug compounds of disclosed herein may be derivatized as prodrugs designed to release the active ingredient in the GI system or in plasma. Thus, such prodrug derivatives are within the scope of this disclosure.

It will also be understood by skilled practitioners of the art that the scope of the compounds or synthetic intermediates embodied in the formula above may include molecules containing chiral centers. The present disclosure includes embodiments where such compounds are present in the form of enantiomers, diastereomers, meso structures, or racemic mixtures.

Generally, it is preferred in some embodiments that compounds disclosed herein, if they are comprised of enantiomers or diastereomers with one or more chiral centers, the preferred compound will be used as a single enantiomer or diastereomer. Single enantiomers or diastereomers may be prepared by using enantiomerically or diasteromerically pure starting reagents, or by the use of synthetic transformations known to provide control of chirality. Alternatively, racemic or diastereomeric mixtures may be resolved into enantiomerically or diastereomerically pure components through the use of standard chiral separation and/or crystallization techniques.

Also included in the scope of this disclosure are radiolabeled isomers or derivatives of the compounds of the formula described above that may be suitable for various in vivo biological studies.

One skilled in the art may prepare compounds of the Formula (I) by any of a number of known synthetic methods beginning with starting materials available from a commercial source or synthesized from simpler available molecules.

The following five reaction schemes are provided as various examples for synthesizing various embodiments of compounds of Formula (I). Some compounds of the disclosure may be synthesized, as described below, where $R^2$ and $R^4$ are as defined above in the description of Formula (I).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds provided by the present disclosure include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labeled compounds are useful in metabolic studies (for example with $^{14}C$), reaction kinetic studies (with, for example $^{2}H$ or $^{3}H$), detection or imagine techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly suitable for PET or SPECT studies. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds provided by the present disclosure and prodrugs thereof can generally be prepared by carrying out the procedures disclosed in the schemes or in the examples and preparations described below by substituting a readily available isotopically labeled reagent for a non-isotopically related reagent. Deuteration is particularly appropriate for compounds containing methyl or methylene groups.

Table 2, below, describes the results of assays carried out on some compounds provided by the present disclosure. Exemplified compounds are confirmed to inhibit ALK5 activity in enzyme and cellular assays in the following assay systems conducted by ThermoFisher in Madison, WI according to their commercially available protocols.

ThermoFisher SelectScreen™ Biochemical Kinase Profiling Service, LanthaScreen™ Eu Kinase Binding Assay TGFBR1 (ALK5)

Exemplified compounds are screened in 1% DMSO (final concentration) by 3-fold serial dilutions from 10,000 nM to 0.316 nM or at single concentrations of 10,000, 1000 and 100 nM according to the following protocol. To low volume, white 384-well plates (Greiner Cat #784207) add 160 nL 100× compound in 100% DMSO, 3.84 uL kinase buffer (50 mM HEPES, pH 7.5, 0.01% BRIJ-35, 10 mM $MgCl_2$, 1 mM EGTA), 8 uL 2× kinase/antibody mixture in kinase buffer (final ALK5 concentration of 5 nM; final Eu-anti-GST antibody concentration of 2 nM), 4 uL 4× Tracer #178 in kinase buffer (final concentration of 5 nM). Gently shake the plates for 30 seconds and incubate at room temperature for 1 hour before reading fluorescence on a plate reader. Percent inhibition is determined compared to DMSO only control (maximal ALK5 tracer binding) and sigmoidal dose response curve fit yielded $IC_{50}$ values as indicated in Table 2.

ThermoFisher SelectScreen™ Cell-Based Pathway Profiling Service GeneBLAzer Beta-Lactamase (Bla) Reporter Technology—TGF-Beta 1 Stimulated SBE-Bla HEK 293T Cell-Based Assay SBE-bla BEK 293T cells are thawed and re-suspended in Assay Media (OPTI-MEM, 0.5% dialyzed FBS, 0.1 mM NEAA, 1 mM Sodium Pyruvate, 100 U/mL/100 μg/mL Pen/Strep) to a concentration of 625,000 cells/mL. 32 μL of cell suspension (20,000 cells) is added to each well of a 384-well Poly-D-Lysine assay plate. Cells in Assay Media are incubated for 16-24 hours in the plate at 37° C./5% $CO_2$ in a humidified incubator. 4 μL of a 10× serial dilution of ALK5 inhibitors (10×=100,000-3.16 nM) is added to appropriate wells of the plate and pre-incubated at 37° C./5% $CO_2$ in a humidified incubator with cells for 30 minutes. Final concentration of inhibitor ranged from 10,000 nM to 0.316 nM. 4 μL of 10×TGF-beta 1 (final concentration of 0.03 nM) is added to wells containing the inhibitors. The plate is incubated for 5 hours at 37° C./5% $CO_2$ in a humidified incubator. 8 μL of 1 μM Substrate Loading Solution is added to each well and the plate is incubated for 2 hours at room temperature before being read on a fluorescence plate reader. Percent inhibition is determined compared to DMSO only control (maximal TGF-beta 1 stimulation) and sigmoidal dose response curve fit yielded $IC_{50}$ values as indicated in Table 2.

TABLE 2

Biological activity assay results

| Compound No. | Cells (SBE_HEK293T) IC50 (nM) | TβRI (ALK5) Binding IC50 (nM) |
| --- | --- | --- |
| 7 | 248 | 5.5 |
| 8 | 84 | 3.3 |
| 16 | 117 | 2.6 |
| 18 | 69 | 6.7 |
| 22 | 27.4 | 7.2 |
| 23 | 239 | 5.2 |
| 24 | 37 | 1.8 |
| 25 | 238 | 7.2 |
| 26 | 33.8 | 3.1 |
| 28 | — | 107 |
| 49 | 2400 | 52 |
| 50 | 253 | 90 |
| 75 | 930 | 66 |
| 86 | 1400 | 129 |
| 88 | 988 | 55 |
| 89 | 27 | 2.5 |
| 90 | 35.6 | 2.5 |
| 91 | 1100 | 22 |
| 92 | 57 | 11 |
| 93 | — | 244 |
| 94 | 4080 | 27 |
| 95 | 151 | 8.9 |
| 96 | 24.9 | 1.7 |
| 97 | 528 | 12.5 |

In Scheme 1 (illustrated below), Exemplary Formula A, which is a subset of compounds encompassed by Formula (I) where n=0, y is a single bond, and X=$CH_2$, may be prepared beginning with ketone (II). Bromination with bromine in methylene chloride provides bromide (III), which is then treated with 4,5-dihydro-3H-pyrrol-2-ylamine hydrobromide (IV) to give the cyclized product (V). Bromination of (V) with N-bromosuccinimide (NBS) in chloroform gives bromide (VI). Suzuki coupling of (VI) with an appropriate boronic ester, for example (VII), gives nitrile (VIII), which is then converted to the corresponding primary amide (IX), Exemplary Formula A, by treatment with sulfuric acid. One skilled in the art will appreciate that use of 4,5-dihydro-3H-pyrrol-2-ylamine hydrobromide substituted with one or more substituents on one of the carbon atoms provides a route to substituted compounds of Formula (I) where n>0 and $R^1$ does not equal hydrogen.

Scheme 1

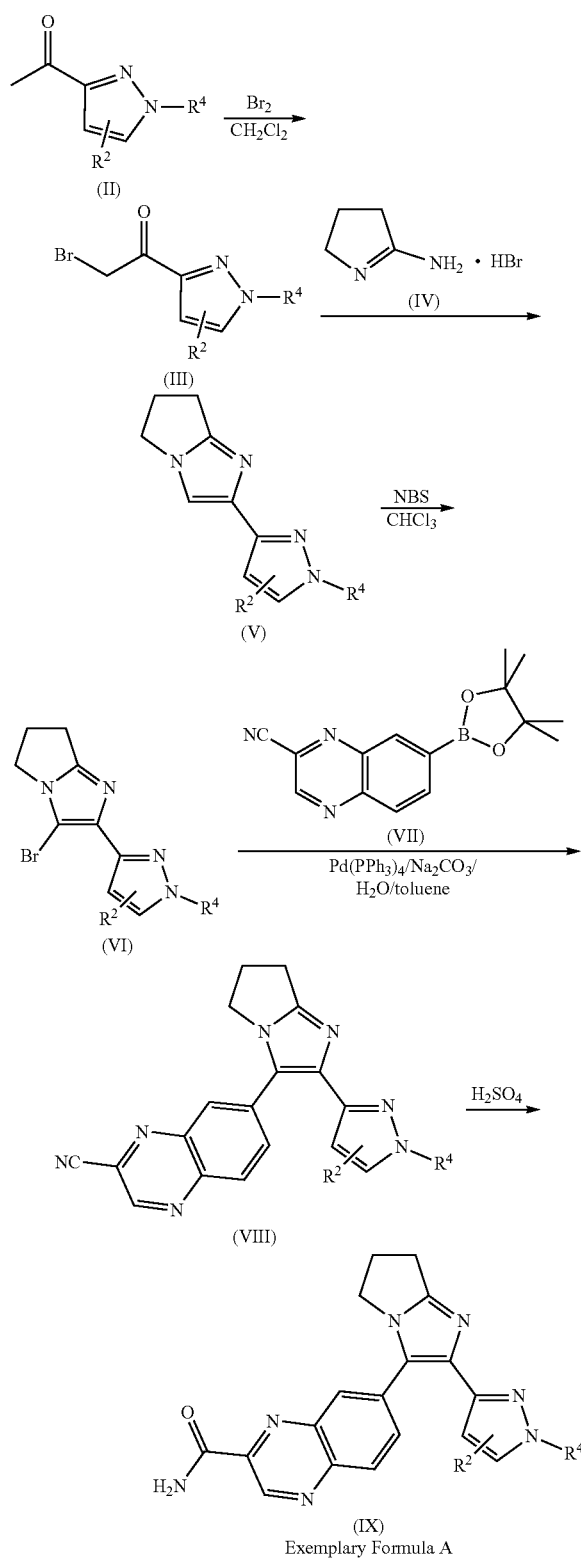

In Scheme 2 (illustrated below), Exemplary Formula B, which is a subset of compounds encompassed by Formula (I) where n=0, y is a single bond, and X=NH, may be prepared beginning with ketone (III). Condensation of (III) with 1-acetylguanidine in dimethylformamide (DMF) provides imidazole (X). Cyclization with 1,2-dibromoethane under basic conditions gives (XI), which is then brominated with N-bromosuccinimide to provide bromide (XII). Suzuki coupling of (XII) with an appropriate boronic ester, for example (XIII), gives amide (XIV), which is then converted to the corresponding free amine (XV), Exemplary Formula B, by treatment with aqueous sodium hydroxide. One skilled in the art will appreciate that use of dibromoethanes with one or more substituents on one or both carbon atoms provides a route to substituted compounds of Formula (I) where n>0 and $R^1$ does not equal hydrogen.

Scheme 2

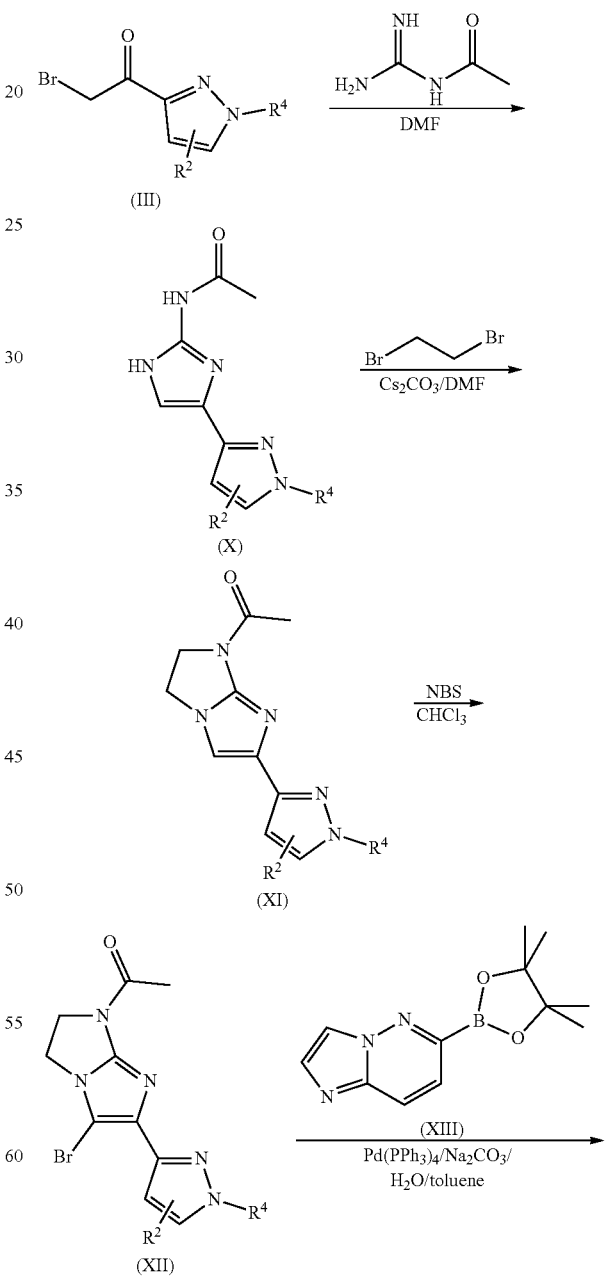

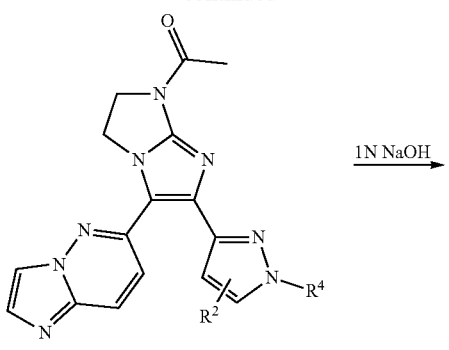

(XIV)

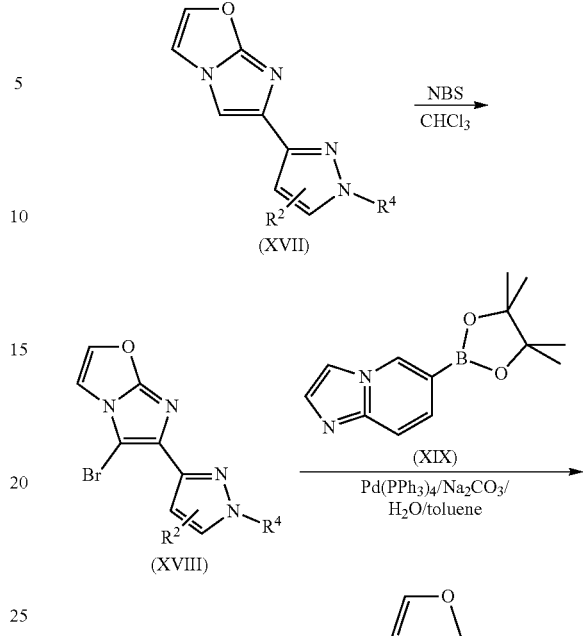

(XV)

Exemplary Formula B

In Scheme 3 (illustrated below), Exemplary Formula C, which is a subset of compounds encompassed by Formula (I) where n=0, y is a double bond, and X=O, may be prepared beginning with ketone (III). Condensation of (III) with 2-aminooxazole in tetrahydrofuran (THF) gives adduct (XVI), which is then treated with titanium(IV) chloride in toluene to provide the cyclized product (XVII). Bromination of (XVII) with N-bromosuccinimide gives bromide (XVIII). Suzuki coupling of (XVIII) with an appropriate boronic ester, such as (XIX), then gives (XX), Exemplary Formula C. One skilled in the art will appreciate that substitution of 2-aminothiazole in place of 2-aminooxazole will provide the compound corresponding to (XX) where the oxygen atom is replaced by a sulfur atom.

Scheme 3

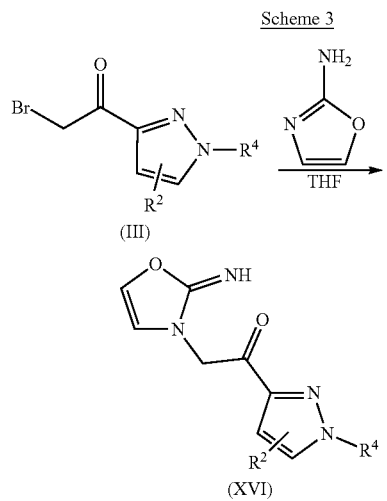

In Scheme 4 (illustrated below), Exemplary Formula D, which is a subset of compounds encompassed by Formula (I) where n=0, y is a single bond, and X=CH$_2$, may be prepared beginning with bromide (VI). Suzuki coupling of boronic ester (XXI) with bromide (VI) gives ester (XXII), which when treated with formamide gives the cyclized product (XXIII), Exemplary Formula D.

Scheme 4

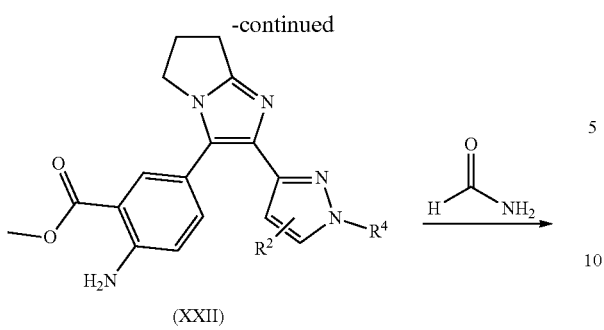

(XXII)

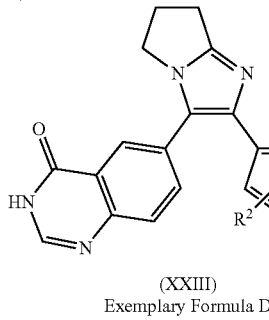

(XXIII)
Exemplary Formula D

In Scheme 5 (illustrated below), Exemplary Formula E which is a subset of compounds encompassed by Formula (I) where n=0, y is a single bond, and X=CH₂, may be prepared beginning with intermediate ester (XXII). Treatment of (XXII) with methylamine in methanol in a sealed tube at elevated temperature gives amide (XXIV). Cyclization of (XXIV) with dimethylformamide-dimethylacetal in DMF at 120° C. provides compound (XXV), Exemplary Formula E. One skilled in the art will appreciate that replacing methylamine in Scheme 5 with other primary amines affords entry into analogues of (XXV) where the methyl group is replaced with other groups including, but not limited to, alkyl, alkenyl, alkynyl, aryl, and heteroaryl groups, or alkyl groups substituted with heterocyclic rings containing one or more heteroatoms.

Scheme 5

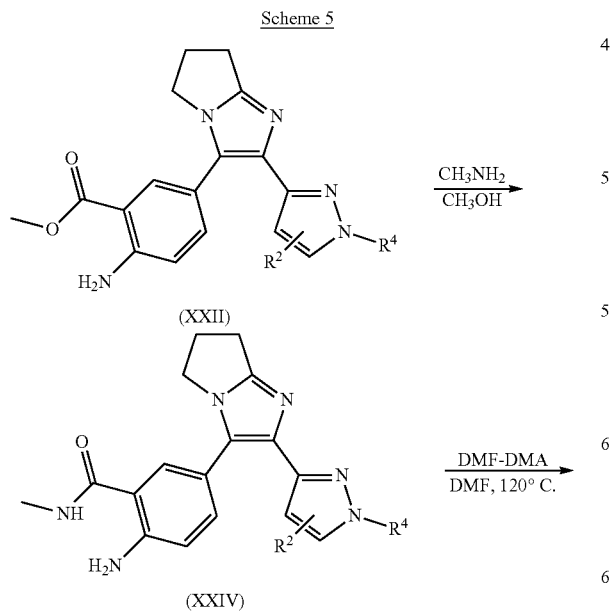

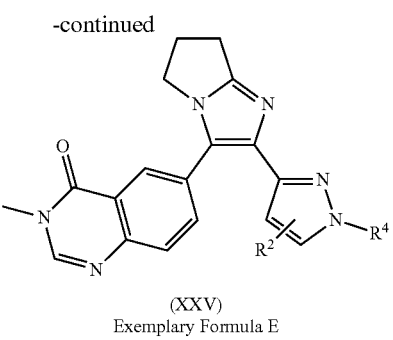

(XXV)
Exemplary Formula E

In Scheme 6 (illustrated below), Exemplary Formula F, which is a subset of compounds encompassed by Formula (I) where n=0, y is a single bond, and X=CH₂, may be prepared beginning with bromide (VI), where treatment with 4,4,4',4',5,5,5',5'-octamethyl-2,2'-bi-1,3,2-dioxaborolane in the presence of potassium acetate and [1,1'-bis(diphenylphosphino)ferrocene]dichloropalladiu(II) (Pd(dppt)Cl₂) in refluxing dioxane gives the pinacol boronic ester (XXVI). Further reaction of (XXVI) with the known intermediate ethyl (E)-3-(5-iodo-1,3,3a-triaza-4-indenyl)acrylate (XXVII) (see: WO 2017/215506) using standard Suzuki coupling conditions provides ester (XXVIII). Treatment of (XXVIII) with trimethylaluminum and ammonium chloride in toluene gives the final amide (XXIX), Exemplary Formula F. One skilled in the art will appreciate that replacing ammonium chloride in the last step with primary or secondary amines affords entry into analogues of (XXIX) where the NH₂ group is replaced by NHR or NR₂ groups, where R can be alkyl, aryl, etc.

Scheme 6

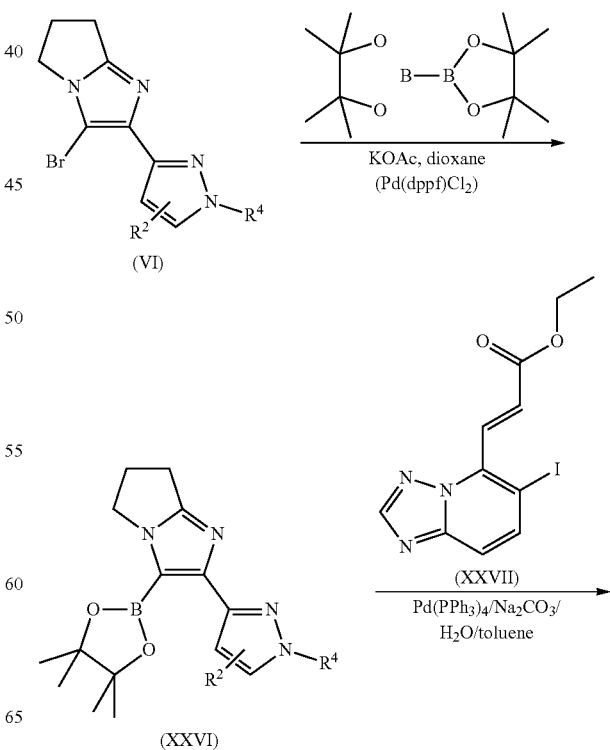

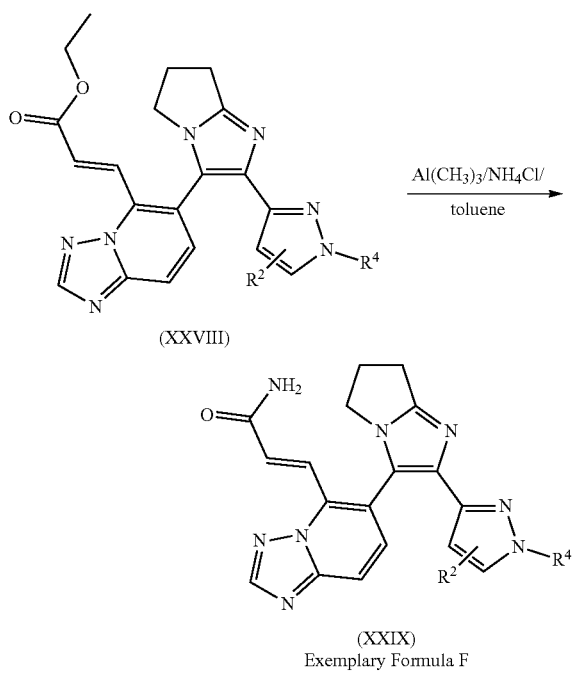

(XXVIII)

(XXIX)
Exemplary Formula F

EXAMPLES

Example 1: Synthesis of 3,4-dihydro-2H-pyrrol-5-amine (iii)

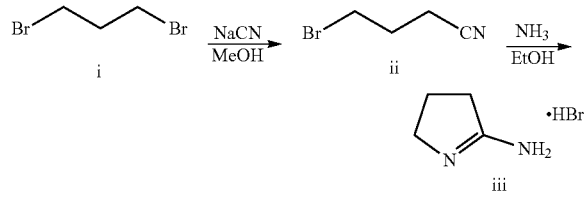

To a solution of 2.5 kg (12.38 mol) 1,3-dibromopropane i (CAS #109-64-8) in 5 L methanol (MeOH—) is added a solution of sodium cyanide (600 g, 12.5 mol) in water (1.25 L) dropwise. The mixture is heated to 55° C. for 8 hours. The mixture is poured into water (7 L) and extracted into dichloromethane (DCM). The organic layer is washed with water (5 L), then dried over sodium sulfate and concentrated to give nitrile ii, which is used in the next step without further purification.

Nitrile ii (200 g, 135 mol) is dissolved in ethanolic ammonia (4 M, 1.25 L) in an autoclave. The autoclave is heated to 110° C. for 6 hours, then cooled to room temperature. The reaction mixture is transferred to a round bottom flask and concentrated under vacuum. The crude residue is washed with methyl tert-butyl ether (MITBE), then 5% methanol in ethyl acetate. The mixture is stirred for 15 minutes at 10° C., and the resultant solid is filtered to give amine iii (130 g, 0.79 mol) as an off-white solid which is used without further purification.

Example 2: Synthesis of 2-bromo-1-(1-isopropyl-1H-pyrazol-3-yl)ethan-1-one (x)

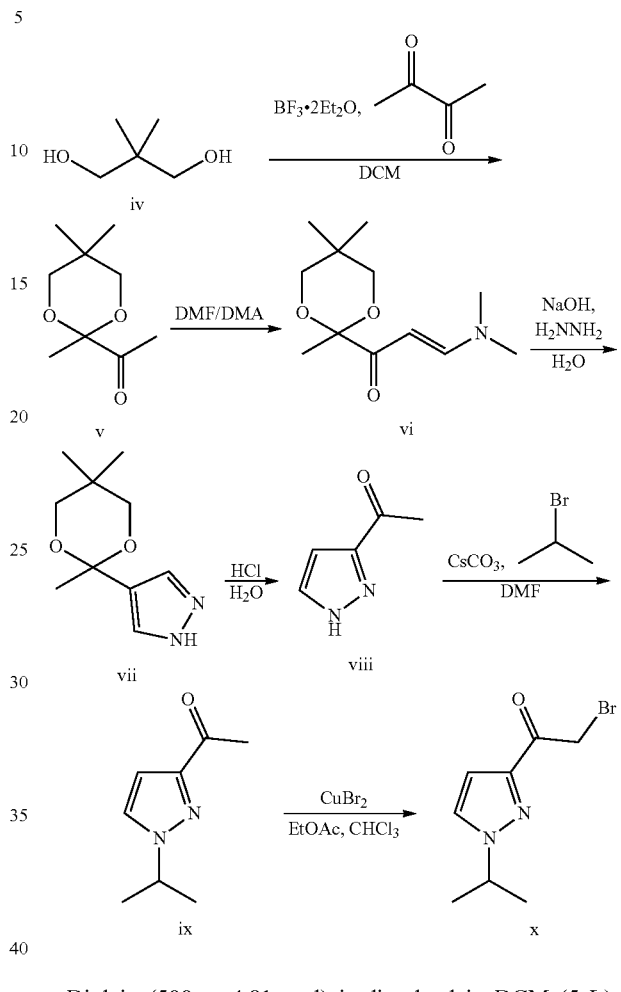

Diol iv (500 g, 4.81 mol) is dissolved in DCM (5 L). Boron trifluoride diethyl etherate ($BF_3 \cdot Et_2O$) (50% in ether, 300 mL, 1.83 mol) is added slowly, followed by diacetyl (400 mL, 4.70 mol). The reaction is stirred for 12 hours, then washed with water (2×2 L). The organic layer is dried over sodium sulfate and concentrated to give ketone v (0.80 kg, 4.65 mol) as a pale yellow liquid which is used without further purification.

Ketone v (800 g, 4.65 mol) is placed in a round bottom flask, and dimethyl formamide dimethyl acetal (DMF/DMA) (1.6 L, 15.04 mol) is added slowly. The reaction is heated to 120° C. for 2 hours, with azeotropic distillation to remove methanol. The solvent is evaporated under vacuum, then hexanes (2 L) are added and the mixture cooled to 5° C. The solid is filtered to give amine vi (1.1 kg, 4.84 mol), which is used without further purification.

A solution of sodium hydroxide (NaOH) (200 g, 5 mol) in water (2 L) is cooled to 10° C., then hydrazine hydrate (99%, 300 mL) is added dropwise. The reaction is warmed to room temperature and amine vi (1 kg, 4.40 mol) is added. The reaction is stirred for 2 hours, then ice cold water (1L) is added, and the mixture stirred for 1 hour at 10 C. The solid is filtered and washed with ice cold water to give acetal vii (800 g, 4.08 mol) as an off-white solid which is used without further purification.

A solution of hydrochloric acid (2.4 L) in water (2.4 L) is cooled to 10° C. Acetal vii (1.2 kg, 6.12 mol) is added and the mixture is stirred for 12 hours. The reaction is cooled to 5° C., and the pH adjusted to 7 by addition of 50% NaOH. The mixture is extracted into 5% methanol in dichloronethane. The organic layer is dried over sodium sulfate, concentrated, and purified by flash column chromatography (1:4 ethyl acetate:petroleum ether) to give pyrazole viii (500 g, 4.54 mol) in 74% yield.

Pyrazole viii (30 g, 0.27 mol) and cesium carbonate (98 g, 030 mol) are dissolved in dimethylformarnide (DMF) (300 mL). 2-Bromopropane (30 mL, 0.32 mol) is added dropwise and the mixture is stirred for 12 hours. The mixture is poured onto water (1 L) and extracted into ethyl acetate. The organic layer is washed with brine, dried over sodium sulfate, and concentrated to give substituted pyrazole ix (22 g, 0.14 mol) as a pale yellow liquid which is used without further purification.

To a solution of pyrazole ix (3 g, 19.7 mmol) in ethyl acetate (EtOAc) (30 mL) and chloroform (300 mL) is added copper (II) bromide (8.8 g, 39.4 mmol). The reaction is heated at 70° C. for 16 hours, after which the mixture is cooled to room temperature and poured onto 10% sodium bicarbonate (300 mL) and extracted into chloroform. The organic layer is washed with brine and concentrated. The residue is purified by flash column chromatography (10% ethyl acetate in petroleum ether) to give bromide x (2.6 g, 11.3 mmol) as a yellow liquid in 57% yield.

Example 3: Synthesis of 3-bromo-2-(1-isopropyl-1H-pyrazol-3-yl)-6,7-dihydro-5H-pyrrolo[1,2-a]imidazole (xii)

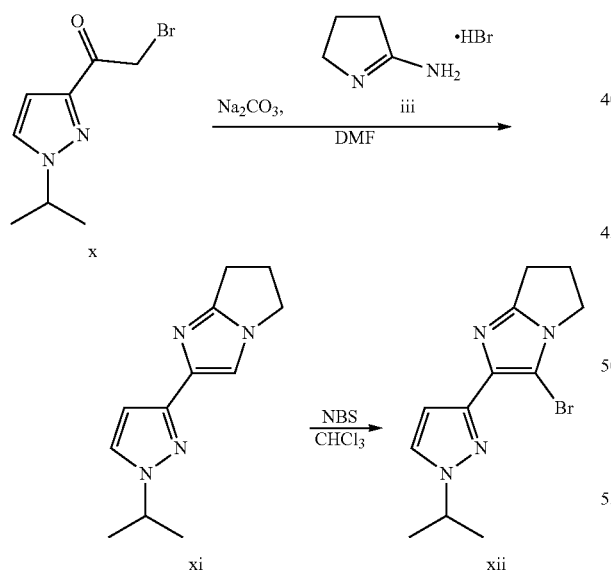

To a solution of bromide x (2.0 g, 8.7 mmol) in DMF (40 mL) is added amine iii (4.2 g, 25.6 mmol) and sodium carbonate (4.6 g, 43.4 mmol). The mixture is heated to 80° C. and stirred for 12 hours, then cooled to room temperature, poured onto water (100 mL) and extracted into 10% isopropanol in chloroform. The organic layer is concentrated under vacuum, then moved to high vacuum to remove residual DMF. The residue is purified by flash column chromatography (3%-5% methanol in DCM) to give imidazole xi (950 mg, 4.39 mmol) as a brown amorphous solid in 50% yield.

A solution of imidazole xi (150 mg, 0.69 mmol) in chloroform (8 mL) is cooled to −10° C., and N-bromosuccinimide (NBS) (76 mg, 0.43 mmol) is added. The temperature is slowly increased to 0° C., and the reaction is stirred for 1 hour. The mixture is poured into an aqueous solution of 10% sodium bicarbonate and extracted into DCM. The organic layer is washed with brine, dried over sodium sulfate, and concentrated. The residue is purified by flash column chromatography (2%-5% methanol in DCM) to give bromide xii (110 mg, 0.37 mmol) as a brown solid in 54% yield.

Example 4: Synthesis of 6-(4,4,5,5-tetramethyl-1,3,2-dioxaborolan-2-yl)imidazo[1,2-a]pyridine-3-carbonitrile (xvi)

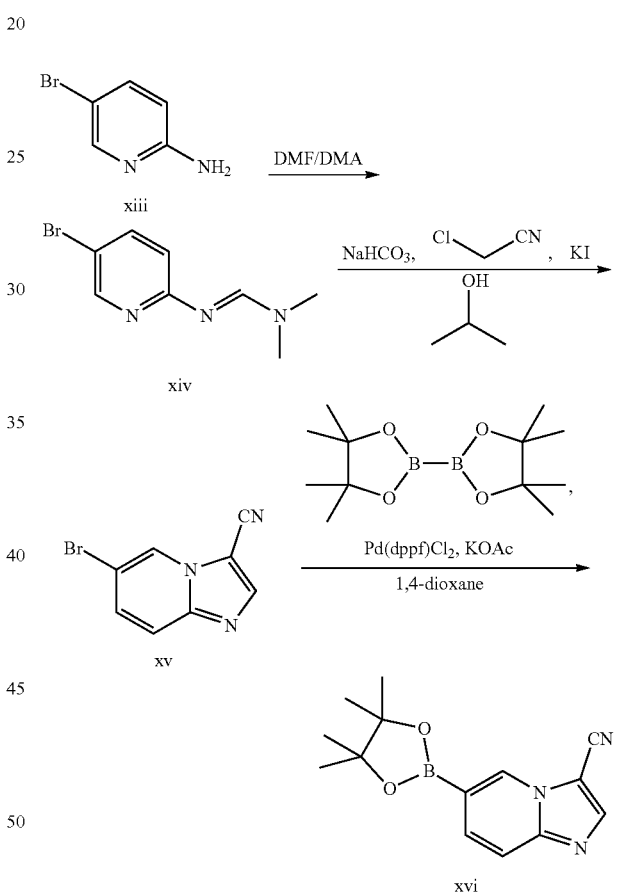

A solution of pyridine xiii (300 g, 1.73 mol) in DMF/DMA (310 g 2.6 mol) is heated to 120° C. with azeotropic distillation to remove methanol for 8 hours. The solvent is removed under vacuum, hexanes (500 mL) is added, and the mixture is cooled to 5° C. The solid is filtered and washed with hexanes to give amine xiv (340 g, 1.50 mol) as a light brown solid which is used without further purification Amine xiv (100 g, 0.44 mol) and sodium bicarbonate (65 g, 0.62 mol) are dissolved in isopropanol (500 mL). Chloroacetonitrile (50 mL, 0.79 mol) and potassium iodide (5 g, 0.30 mob) are added. The mixture is heated to reflux for 18 hours, then concentrated. Water is added to the residue and the mixture is extracted into ethyl acetate. Activated carbon (10% wt/wt) is then added to the ethyl acetate solution, and the mixture is heated to 55° C. for 15 minutes before filtering. The filtrate is dried over sodium sulfate and concentrated. Hexanes are added to the residue and the mixture is cooled and filtered to give bromide xv (50 g, 0.23 mol) as an off-white solid which is used without further purification.

A solution of bromide xv (1.0 g, 4.5 mmol) in 1,4-dioxane (80 mL) is degassed for 30 minutes under inert atmosphere, then bis(pinacolato diboron) (B$_2$pin$_2$) (1.36 g, 5.4 mmol) is added and the mixture is degassed for a further 30 minutes. Potassium acetate (1.6 g, 16.3 mmol) is added, followed by degassing for 5 minutes, after which [1,1'-bis(diphenylphosphino)ferrocene]dichloropalladium(II) (Pd(dppf)Cl$_2$) (320 mg, 0.44 mmol) is added, and the mixture is degassed for 10 minutes. The reaction is heated to 80° C. for 12 hours, then cooled to room temperature, filtered through Celite®, and concentrated. The residue is purified by flash column chromatography (3% methanol in DCM) to give dioxaborolane xvi (600 mg, 0.22 mmol) as a grey solid in 5% yield.

Example 5: Synthesis of 6-(2-(1-isopropyl-1H-pyrazol-3-yl)-6,7-dihydro-5l-pyrrolo[1,2-a]imidazol-3-yl)imidazo[1,2-a]pyridine-3-carbonitrile (xvii)

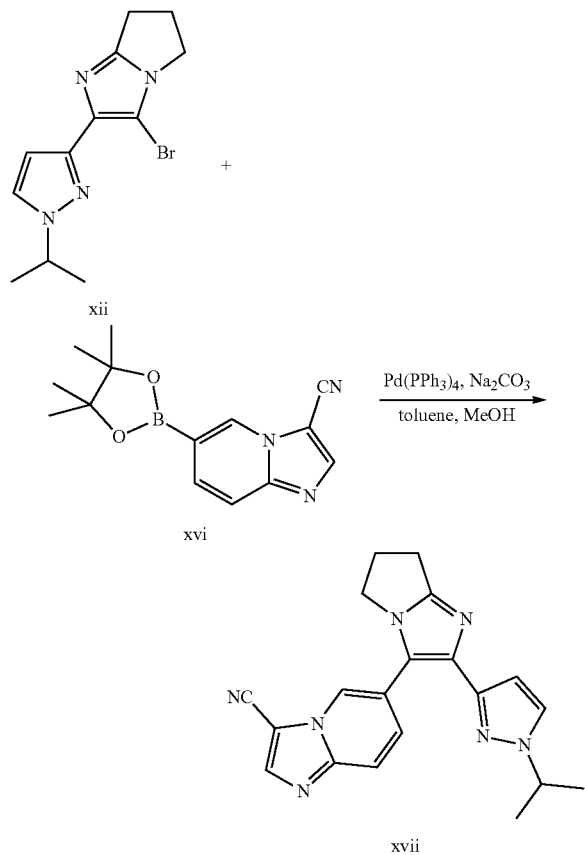

for 12 hours. The mixture is cooled to room temperature, filtered through Celite®, and washed with 10% methanol in DCM. The filtrate is concentrated under vacuum and the residue purified by flash column chromatography (2%-4% methanol in DCM) to give nitrile (xvii) (22 mg, 0.06 mmol) in 31% yield; m/z: 358.1.

Example 6: Synthesis of 6-(2-(1-isopropyl-1H-pyrazol-3-yl)-6,7-dihydro-5H-pyrrolo[1,2-a]imidazol-3-yl)imidazo[1,2-a]pyridine-3-carboxamide (7)

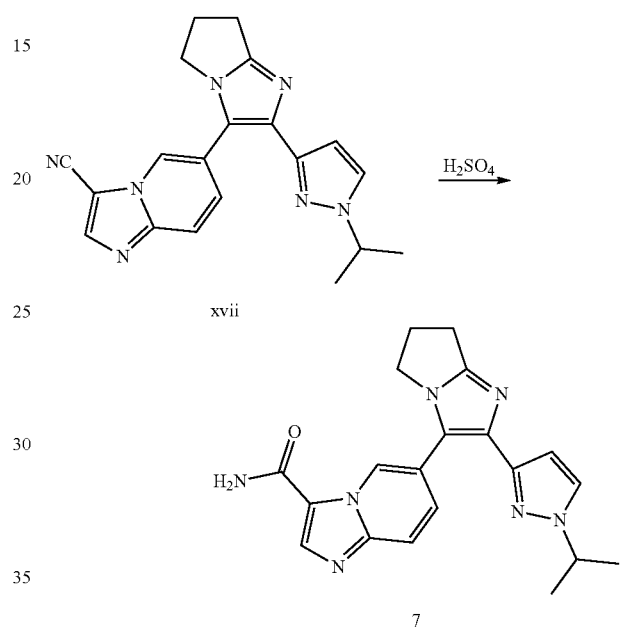

Nitrile xvii (34.0 mg, 0.095 mmol) is dissolved in sulfuric acid (1 mL) at 5° C. The reaction is allowed to warm to room temperature and stirred for 4 hours. The mixture is poured into ice cold water, and aqueous ammonia (18% solution) is added until pH 9 is reached. The mixture is extracted into DCM and the organic layer is washed with brine, dried over sodium sulfate, and concentrated. The residue is purified by flash column chromatography (3%-6% methanol in DCM) to give 7 (18 mg, 0.05 mmol) as an off-white solid in 53% yield.

Other compounds that may be synthesized using the methods described in the Examples above are shown in Table 3.

TABLE 3

| # | Structure and Name |
|---|---|
| 1 | |

TABLE 3-continued

| # | Structure and Name |
|---|---|
| 2 | 6-(2-(1-isopropyl-1H-pyrazol-3-yl)-6,7-dihydro-5H-pyrrolo[1,2-a]imidazol-3-yl)imidazo[1,2-a]pyridine |
| | 3-{2-(1,3a-Diaza-5-indenyl)-1,4-diazabicyclo[3.3.0]octa-2,4-dien-3-yl}-1-cyclopropyl-1H-pyrazole |
| 8 | 5-(3-(1-Cyclopropyl-1H-pyrazol-3-yl)-1,4-diazabicyclo[3.3.0]octa-2,4-dien-2-yl}-1,3a-diaza-3-indenecarboxamide |
| 43 | 5-{3-(1-Cyclobutyl-1H-pyrazol-3-yl)-1,4-diazabicyclo[3.3.0]octa-2,4-dien-2-yl}-1,3a-diaza-3-indenecarboxamide |
| 47 | 5-{3-[1-(3,3-Difluorocyclobutyl)-1H-pyrazol-3-yl]-1,4-diazabicyclo[3.3.0]octa-2,4-dien-2-yl}-1,3a-diaza-3-indenecarboxamide |
| 48 | 5-{3-[1-(2,2-Difluoroethyl)-1H-pyrazol-3-yl]-1,4-diazabicyclo[3.3.0]octa-2,4-dien-2-yl}-1,3a-diaza-3-indenecarboxamide |
| 79 | 6-(2-(1-cyclopropyl-1H-pyrazol-3-yl)-6,7-dihydro-5H-pyrrolo[1,2-a]imidazol-3-yl)-3-(methylsulfonyl)imidazo[1,2-a]pyridine |

Example 7: Synthesis of methyl 2-amino-5-(4,4,5,5-tetraethyl-1,3,2-dioxaborolan-2-yl)benzoate (xx)

A solution of amine xviii (100 g, 0.66 mol) in DMF (500 mL) is cooled to 10° C. and NBS (129.6 g, 0.73 mol) is added. The reaction is stirred for 2 hours, then a saturated aqueous solution of sodium carbonate is added until the pH reaches 7. The mixture is extracted into ethyl acetate, and the organic layer is washed with brine, dried over sodium sulfate, and concentrated. The residue is purified by flash column chromatography (10% ethyl acetate in petroleum ether) to give bromide xix (108 g, 0.47 mol) as a white solid in 71% yield.

The synthesis is completed as described above in Example 4 in the synthesis of dioxaborolane xiv to give dioxaborolane xx in 75% yield.

Example 8: Synthesis of 6-{3-(1-cyclopropyl-1H-pyrazol-3-yl)-1,4-diazabicyclo[3.3.0]octa-2,4-dien-2-yl}-3H-quinazolin-4-one (16)

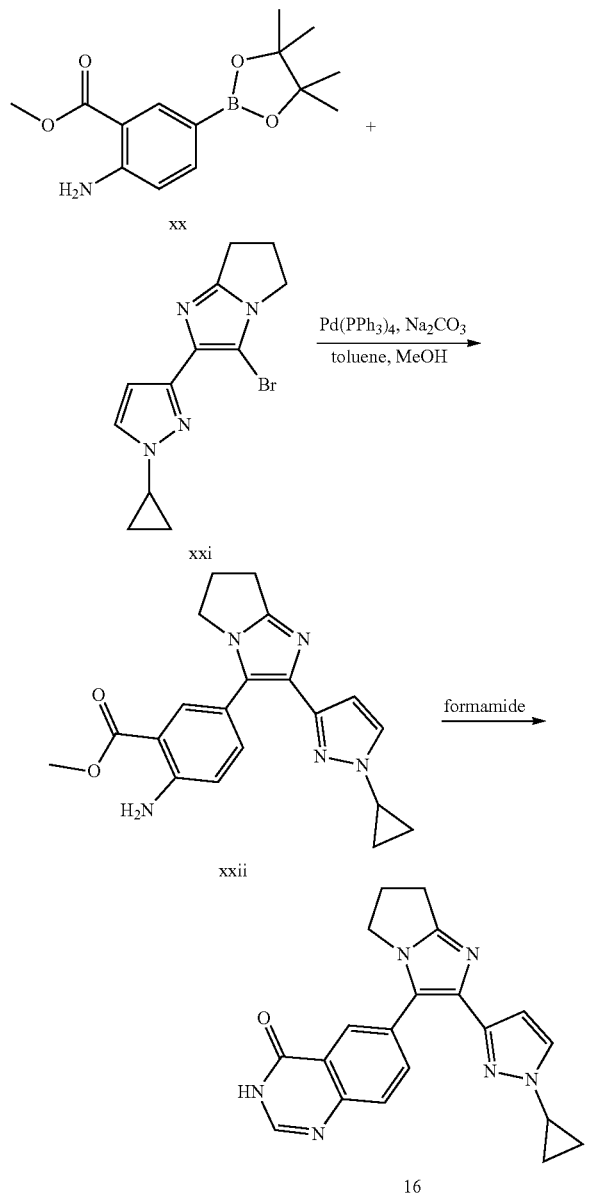

Bromide xxi is synthesized as described in Examples 1-3, using the procedure described in Example 28 to provide cyclopropyl substituted pyrazole lxxxiii. Bromide xxi is coupled to dioxaborolane xx as described in Example 5 to give ester xxii.

Ester xxii (110 ng, 0.31 mmol) is dissolved in formarnide (2 nL). The mixture is heated to 160° C. for 10 hours, then cold water is added, and the mixture is extracted into DCM. The organic layer is washed with water and concentrated under vacuum. The residue is purified by flash column chromatography (3%-6% methanol in DCM) to give 16 (18 mg, 0.05 mmol) as a brown solid in 16% yield.

Further compounds that may also be synthesized using the methods described in Example 8 are shown in Table 4.

TABLE 4

| # | Structure and Name |
|---|---|
| 15 | 6-{3-(1-Isopropyl-1H-pyrazol-3-yl)-1,4-diazabicyclo[3.3.0]octa-2,4-dien-2-yl}-3H-quinazolin-4-one |
| 49 | 6-{3-[1-(2,2-Difluoroethyl)-1H-pyrazol-3-yl]-1,4-diazabicyclo[3.3.0]octa-2,4-dien-2-yl}-3H-quinazolin-4-one |

Example 9: Synthesis of 6-{3-(1-cyclopropyl-1H-pyrazol-3-yl)-1,4-diazabicyclo[3.3.0]octa-2,4-dien-2-yl}-3-methyl-3H-quinazolin-4-one (18)

87

-continued

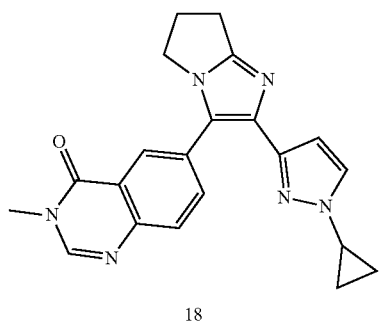

18

To a solution of 16 (12 mg, 0.03 mmol) in methanol (MeOH) (4.0 mL) is added sodium methoxide (NaOMe) (6 mg, 0.11 mmol), followed by methyl iodide (MeI) (10 mg, 0.07 mmol). The reaction is stirred for 12 hours, then concentrated. Water is added to the residue and the mixture is extracted into DCM. The organic layer is concentrated and the crude residue is purified by flash column chromatography (3%-5% methanol in DCM) to give 18 (7 mg, 0.02 mmol) in 63% yield. MS: m/z 373.

Alternatively, 18 may be prepared using the method described in Example 21.

Other compounds that may also be synthesized using the method described in Example 9 are shown below in Table 5.

TABLE 5

| # | Structure and Name |
|---|---|
| 17 | 6-{3-(1-Isopropyl-1H-pyrazol-3-yl)-1,4-diazabicyclo[3.3.0]octa-2,4-dien-2-yl}-3-methyl-3H-quinazolin-4-one |
| 50 | 6-{3-[1-(2,2-Difluoroethyl)-1H-pyrazol-3-yl]-1,4-diazabicyclo[3.3.0]octa-2,4-dien-2-yl}-3-methyl-3H-quinazolin-4-one |

88

TABLE 5-continued

| # | Structure and Name |
|---|---|
| 72 | 3-methyl-6-(2-(1-(oxetan-3-yl)-1H-pyrazol-3-yl)-6,7-dihydro-5H-pyrrolo[1,2-a]imidazol-3-yl)quinazolin-4(3H)-one |

Example 10: Synthesis of 6-{3-(1-cyclopropyl-1H-pyrazol-3-yl)-1,4-diazabicyclo[3.3.0]octa-2,4-dien-2-yl}-3-(2-morpholinoethyl)-3H-quinazolin-4-one (28)

To a solution of 16 (100 mg, 0.28 mmol) in DMF (3 mL) is added cesium carbonate (109 mg, 0.34 mmol) and 1,2-dibromoethane (1132 mg, 0.70 mmol). The reaction is heated to 85° C. for 4 hours, then cooled to room temperature. Water is added, and the mixture is extracted into DCM. The organic layer is washed with brine, dried over sodium sulfate, and concentrated. The residue is purified by flash column chromatography (3%-4% methanol in DCM) to give bromide xxiii (48 mg, 0.10 mmol) as a brown solid in 36% yield.

Bromide xxiii (100 mg, 0.22 mmol) is dissolved in morpholine (4 mL, 46.3 mmol) and heated to 120° C. The mixture is stirred for 4 hours, then concentrated. The crude residue is purified by flash column chromatography (3%-6% methanol in DCM) to give 28 (8 mg, 0.02 mmol) in 8% yield MIS: m/z 472.3.

Compound 27, shown below in Table 6, may also be synthesized using the methods described in Example 10.

TABLE 6

| # | Structure and Name |
|---|---|
| 27 | 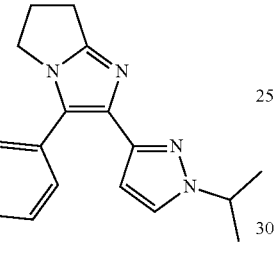<br>6-{3-(1-Isopropyl-1H-pyrazol-3-yl)-1,4-diazabicyclo[3.3.0]octa-2,4-dien-2-yl}-3-(2-morpholinoethyl)-3H-quinazolin-4-one |

Example 11: Synthesis of 2-(6-(2-(1-cyclopropyl-1H-pyrazol-3-yl)-6,7-dihydro-5H-pyrrolo[1,2-a]imidazol-3-yl)imidazo[1,2-a]pyridin-3-yl)propan-2-ol (75)

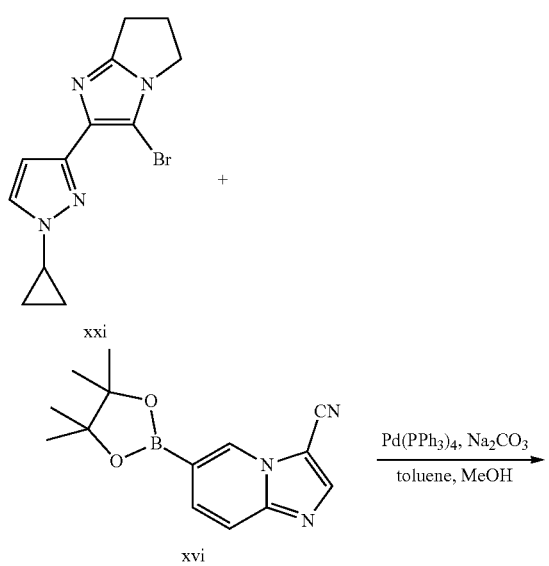

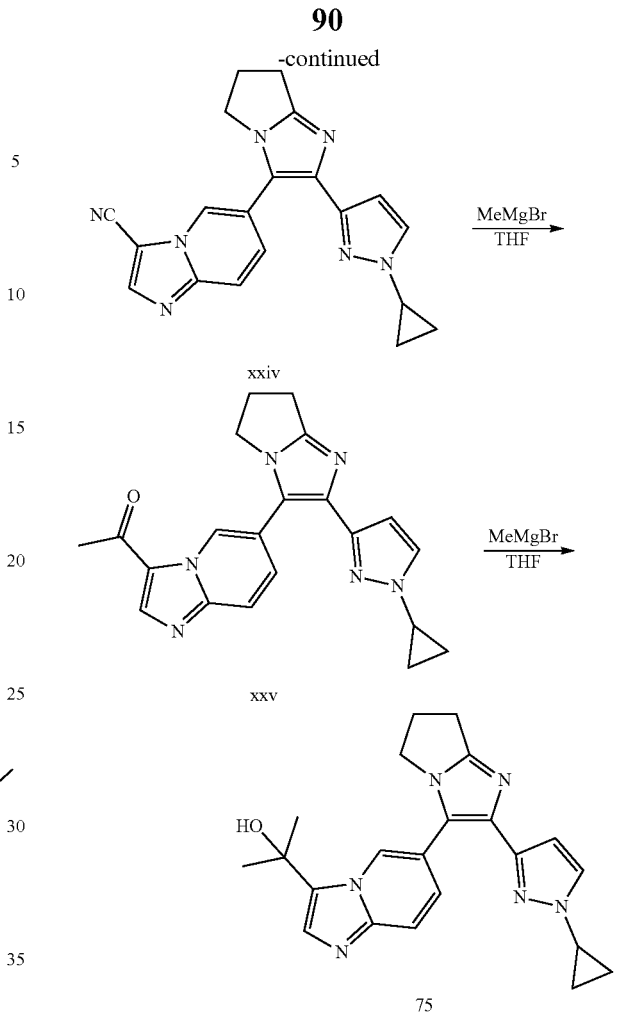

Nitrile xxiv is synthesized as described in Examples 1-3. Nitrile xxiv (50 mg, 0.14 mmol) is dissolved in tetrahydrofuran (THF) (6 mL). Methyl magnesium bromide (1.3 M in THF, 0.13 mL, 0.17 mmol) is added. After 1 hour, the starting material is still present by TLC (thin layer chromatography). A further 0.43 mL (0.56 mmol) of methyl magnesium bromide (1.3 M in THF) is added and the reaction is stirred for a further 30 minutes, after which the reaction is complete by TLC. The reaction is quenched with aqueous ammonium chloride (18% solution) and extracted into ethyl acetate. The organic layer is washed with brine, dried over sodium sulfate, and concentrated. The residue is purified by flash column chromatography (5% methanol in DCM) to give ketone xxv as an off-white solid in 50% yield.

Ketone xxv (60 mg, 0.16 mmol) is dissolved in THE (5 mL). Methyl magnesium bromide (1.3 M in THF, 0.62 mL, 0.81 mmol) is added, and the mixture is stirred for 30 minutes. The reaction is quenched with a saturated aqueous solution of ammonium chloride, then extracted into ethyl acetate. The organic layer is washed with brine, dried over sodium sulfate, and concentrated. The residue is purified by flash column chromatography (2%-5% methanol in DCM) to give 75 as a brown solid (18 mg, 0.05 mmol) in 29% yield. MS: m/z 389.3.

Example 12: Synthesis of 6-{3-[1-(2,2-difluoro-ethyl)-1H-pyrazol-3-yl]-1,4-diazabicyclo[3.3.0]octa-2,4-dien-2-yl}-3H-quinazolin-4-one (49)

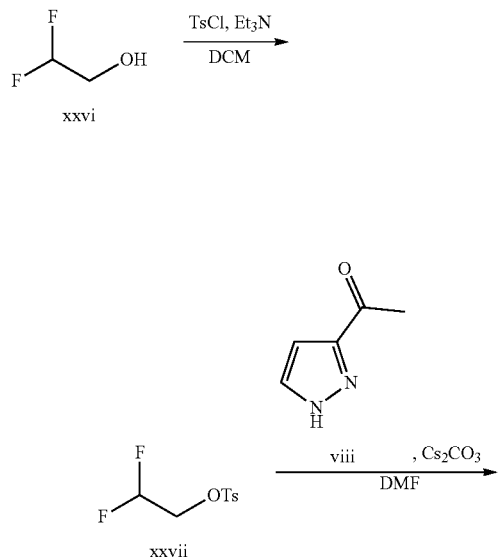

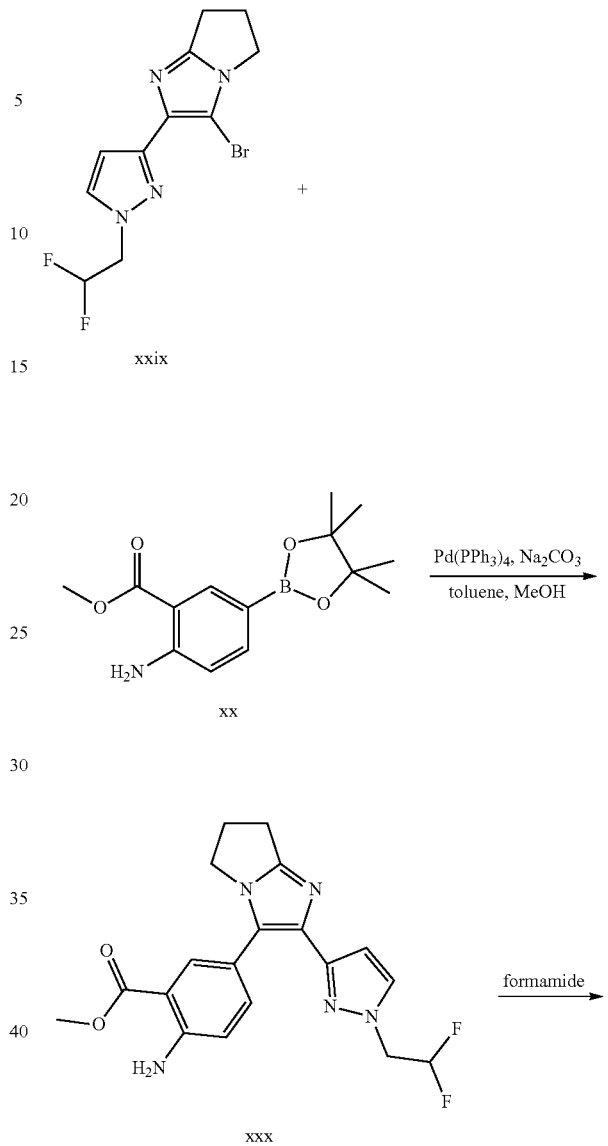

2,2-Difluoroethanol xxvi (25 g, 0.30 mol) is dissolved in DCM (500 mL). Triethylamine (Et₃N) (94 g, 0.93 mmol) is added, and the mixture is cooled to 0° C. p-Toluene sulfonyl chloride (TsCl) (89 g, 0.47 mmol) is added, and the reaction is stirred for 12 hours, after which water is added and the mixture is stirred for 15 minutes before extracting into DCM. The solvent is removed, and the residue is purified by flash column chromatography (50% petroleum ether in ethyl acetate) to give tosylate xxvii (20 g, 0.08 mol) in 28% yield.

Pyrazole viii (20 g, 0.18 mol) is dissolved in dimethylformamide (DMF) (300 mL), and cesium carbonate (70 g, 0.22 mol) is added, followed by tosylate xxvii (45 g, 0.19 mol). The mixture is stirred for 12 hours, then poured into ice cold water and extracted into ethyl acetate. The organic layer is washed with brine, dried over sodium sulfate, and concentrated. The residue is purified by flash column chromatography (10% ethyl acetate in petroleum ether) to give difluoride xxviii (2.56 g, 0.15 mol) in 83% yield.

Difluoride xxviii is then subjected to the conditions described in Example 2 for the formation of bromine x, and those described in Example 3 in the synthesis of xii to give bromide xxix shown below.

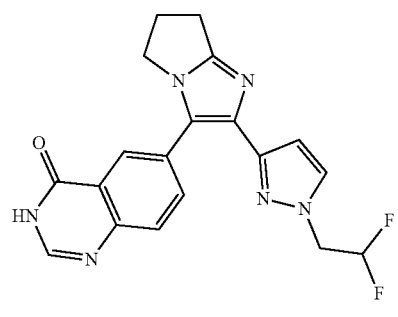

Once accessed, bromide xxix is subjected to the conditions described in Example 8 to give 49 in 44% yield from xxx. MS: m/z 383.2.

Using these conditions, along with those described in the previous examples, the compounds shown below in Table 7 may be synthesized.

TABLE 7

| # | Structure and Name |
|---|---|
| 48 | 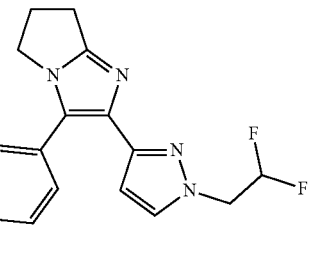<br>5-{3-[1-(2,2-Difluoroethyl)-1H-pyrazol-3-yl]-1,4-diazabicyclo[3.3.0]octa-2,4-dien-2-yl}-1,3a-diaza-3-indenecarboxamide |
| 50 | 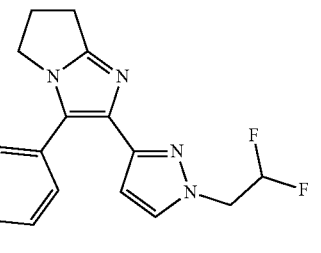<br>6-{3-[1-(2,2-Difluoroethyl)-1H-pyrazol-3-yl]-1,4-diazabicyclo[3.3.0]octa-2,4-dien-2-yl}-3-methyl-3H-quinazolin-4-one |
| 51 | 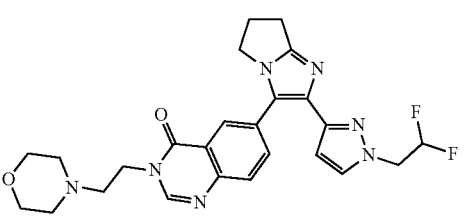 [SMILES: O=c1c2cc(-c3c(-c4ccn(CC(F)F)n4)nc4n3CCC4)ccc2ncn1CCN1CCOCC1]<br>6-{3-[1-(2,2-Difluoroethyl)-1H-pyrazol-3-yl]-1,4-diazabicyclo[3.3.0]octa-2,4-dien-2-yl}-3-(2-morpholinoethyl)-3H-quinazolin-4-one |

Example 13: Synthesis of 6-(2-(1-cyclobutyl-1H-pyrazol-3-yl)-6,7-dihydro-5H-pyrrolo[1,2-a]imidazol-3-yl)-3-methylquinazolin-4(3H)-one (94)

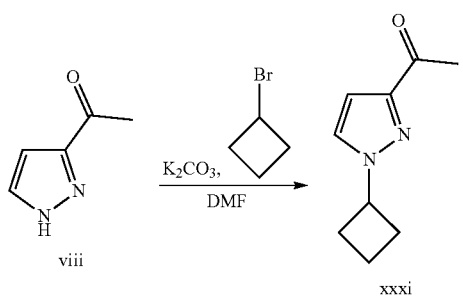

Pyrazole viii (8 grams, 72.7 mmol) is dissolved in DMF (120 mL). Potassium carbonate (15 g, 107.9 mmol) is added, followed by bromocyclobutane (10.7 g, 79.3 mmol). The reaction is stirred at 65° C. for 16 hours, after which water is added. The mixture is extracted into ethyl acetate and the organic layer is concentrated under vacuum. The residue is purified by flash column chromatography (12% ethyl acetate in petroleum ether) to give cyclobutane xxxi (5 g, 30.4 mmol) as a pale yellow oil in 42% yield.

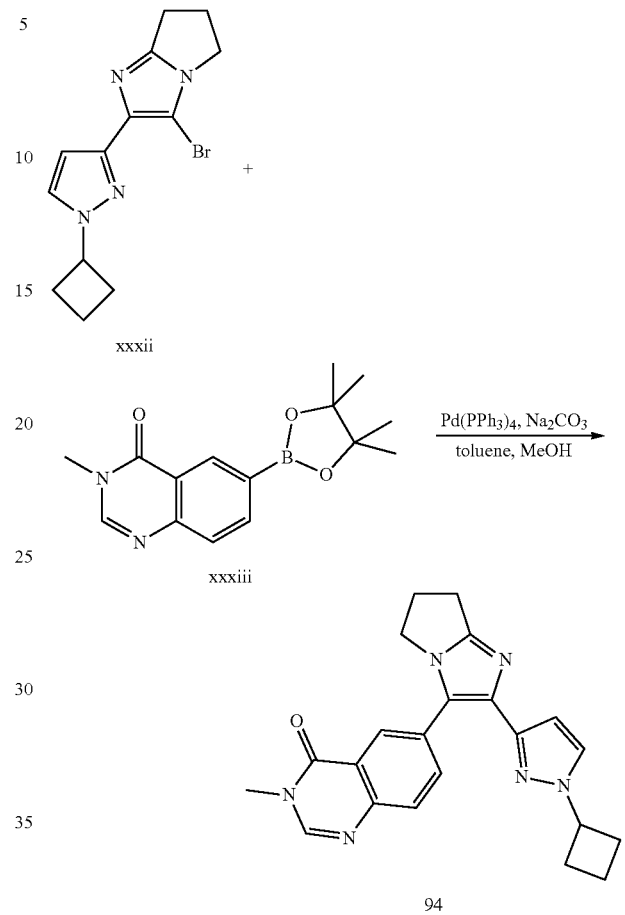

Cyclobutane xxxi is further modified according to the conditions described in Example 2 in the formation of x and Example 3 in the formation of xii to give bromide xxxii. Dioxaborolane xxxiii is synthesized as described in Example 20. Bromide xxxii and dioxaborolane xxxiii are subjected to the conditions described in Example 8 to give 94 (38 mg, 0.10 mmol) as a brown solid in 15% yield from xxxii. MS: m/z 387.2.

In addition to 94, compound 43 (shown in Table 8) may also be synthesized using these methods.

TABLE 8

| # | Structure and Name |
|---|---|
| 43 | 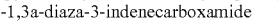<br>5-{3-(1-Cyclobutyl-1H-pyrazol-3-yl)-1,4-diazabicyclo[3.3.0]octa-2,4-dien-2-yl}-1,3a-diaza-3-indenecarboxamide |

Example 14: Synthesis of 5-bromo-6-(1-cyclopropyl-1H-pyrazol-3-yl)imidazo[2,1-b]thiazole (xl)

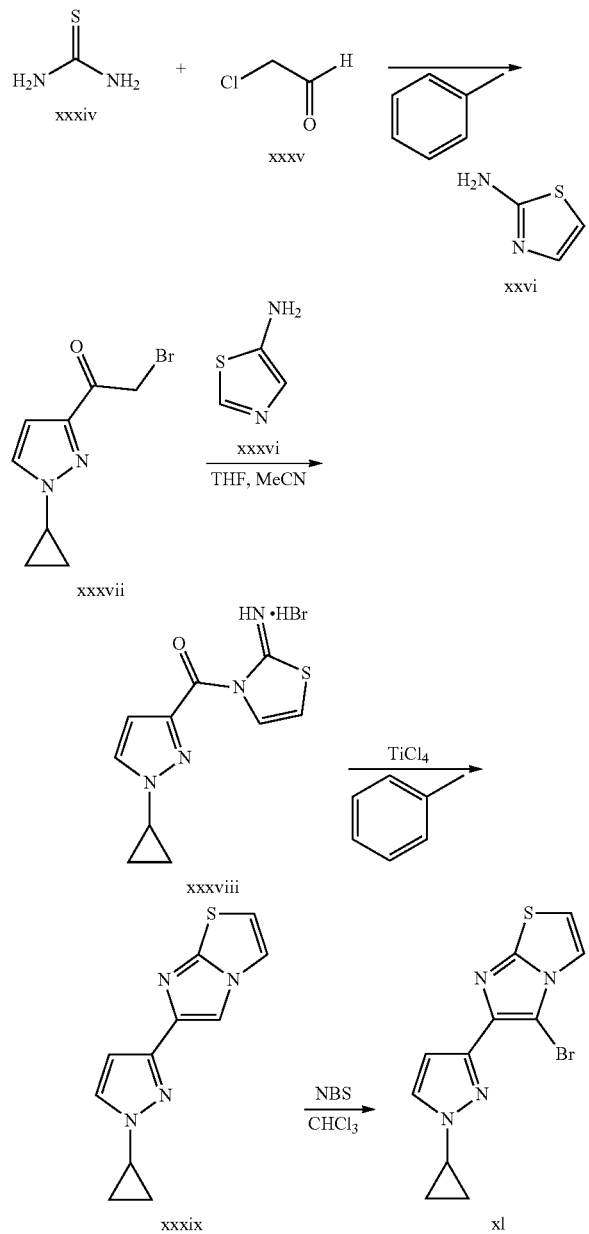

Thiourea xxxiv (50% in H₂O, 184 g, 1.17 mol) is added to toluene (600 mL). 2-Chloroacetaldehyde xxxv (60 g, 0.79 mol) is added, and the mixture is heated to 80° C. for 3 hours, then cooled to 10° C. The pH is adjusted to 7 with aqueous sodium bicarbonate and the mixture is extracted into ethyl acetate and concentrated to give xxxvi as a brown solid in 78% yield.

Bromide xxxvii is synthesized as described in Example 2, substituting bromocyclopropane for 2-bromopropane.

To a solution of thiazole xxxvi (2.0 g, 20.0 mmol) in tetrahydrofuran (THF) (25 mL) and acetonitrile (MeCN) (50 mL) is added bromide xxxvii (5.0 g, 21.8 mmol). The mixture is stirred for 18 hours, then cooled to 10° C. and stirred for a further 30 minutes. The precipitate is filtered and washed with MeCN to give bromide salt xxxviii (2.05 g, 6.5 mmol), which is used without further purification.

Bromide salt xxxviii (4 g, 12.7 mmol) is dissolved in toluene (80 mL) and cooled to 0° C. Titanium tetrachloride (1.0 M in toluene, 61 mL, 61 mmol) is added dropwise, after which the reaction is heated 100° C. for 6 hours. The reaction is cooled to 10° C. and 10% aqueous sodium bicarbonate is slowly added until the pH reached 9. The mixture is stirred for one hour, then extracted into ethyl acetate. The organic layers are washed with brine, dried over sodium sulfate, and concentrated. The crude residue is purified by flash column chromatography (3% to 6% methanol in DCM) to give thiazole xxxix (2.4 g, 10.2 mmol) as a brown solid in 85% yield.

Thiazole xxxix is brominated using the method described in the synthesis of xii (Example 3) to give bromide xl in 44% yield.

One of skill in the art will appreciate that the same synthetic techniques may be applied to access the compounds shown below in Table 9.

TABLE 9

| # | Structure and Name |
|---|---|
| 13 | 5-{7-(1-Isopropyl-1H-pyrazol-3-yl)-4-thia-1,6-diazabicyclo[3.3.0]octa-2,5,7-trien-8-yl}-1,3a-diaza-3-indenecarboxamide |
| 14 | 5-{7-(1-Cyclopropyl-1H-pyrazol-3-yl)-4-thia-1,6-diazabicyclo[3.3.0]octa-2,5,7-trien-8-yl}-1,3a-diaza-3-indenecarboxamide |
| 33 | 6-{7-(1-Isopropyl-1H-pyrazol-3-yl)-4-thia-1,6-diazabicyclo[3.3.0]octa-2,5,7-trien-8-yl}-3-(2-morpholinoethyl)-3H-quinazolin-4-one |

TABLE 9-continued

| # | Structure and Name |
|---|---|
| 34 | 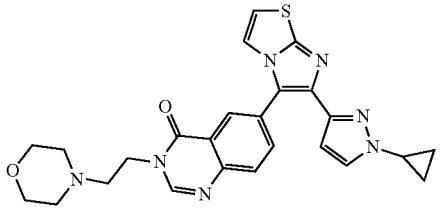 [SMILES: O=c1c2cc(-c3c(-c4ccn(C5CC5)n4)nc4sccn34)ccc2ncn1CCN1CCOCC1]
6-{7-(1-Cyclopropyl-1H-pyrazol-3-yl)-4-thia-1,6-diazabicyclo[3.3.0] octa-2,5,7-trien-8-yl}-3-(2-morpholinoethyl)-3H-quinazolin-4-one |
| 39 | 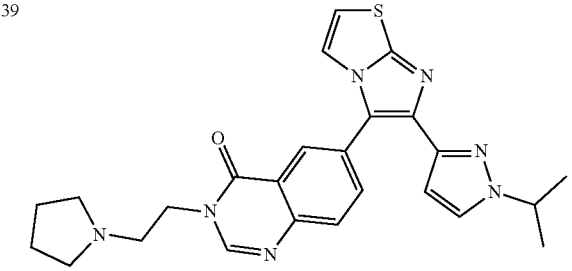
6-{7-(1-Isopropyl-1H-pyrazol-3-yl)-4-thia-1,6-diazabicyclo[3.3.0]octa-2,5,7-trien-8-yl}-3-[2-(1-pyrrolidinyl)ethyl]-3H-quinazolin-4-one |
| 40 | 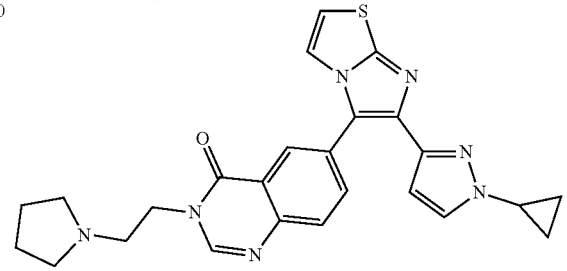
6-{7-(1-Cyclopropyl-1H-pyrazol-3-yl)-4-thia-1,6-diazabicyclo[3.3.0] octa-2,5,7-trien-8-yl}-3-[2-(1-pyrrolidinyl)ethyl]-3H-quinazolin-4-one |
| 46 | 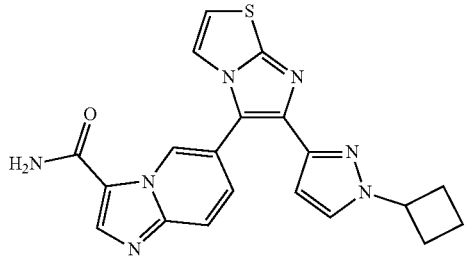 [SMILES: NC(=O)c1cnc2ccc(-c3c(-c4ccn(C5CCC5)n4)nc4sccn34)cn12]
5-{7-(1-Cyclobutyl-1H-pyrazol-3-yl)-4-thia-1,6-diazabicyclo[3.3.0] octa-2,5,7-trien-8-yl}-1,3a-diaza-3-indenecarboxamide |
| 77 | 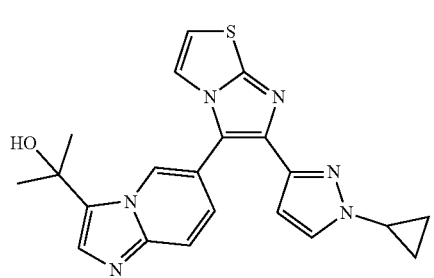 [SMILES: CC(C)(O)c1cnc2ccc(-c3c(-c4ccn(C5CC5)n4)nc4sccn34)cn12]
2-(6-(6-(1-cyclopropyl-1H-pyrazol-3-yl)imidazo[2,1-b]thiazol-5-yl)imidazo[1,2-a]pyridin-3-yl)propan-2-ol |

TABLE 9-continued

| # | Structure and Name |
|---|---|
| 81 | 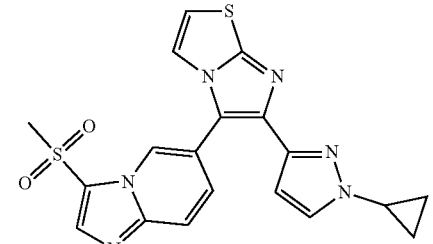
6-(1-cyclopropyl-1H-pyrazol-3-yl)-5-(3-(methylsulfonyl)imidazo[1,2-a]pyridin-6-yl)imidazo[2,1b]thiazole |

Example 15: Synthesis of 6-(6-(1-isopropyl-1H-pyrazol-3-yl)imidazo[2,1-b]thiazol-5-yl)quinazolin-4(3H)-one hydrochloride (97)

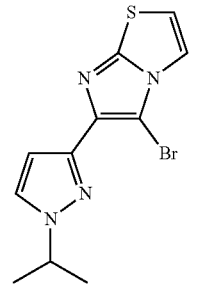

xli

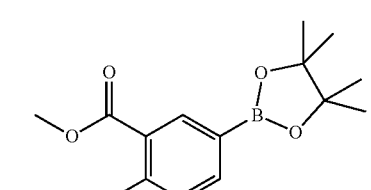

xx

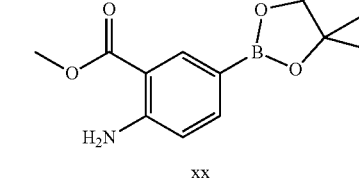

xlii

Bromide xli and dioxaborolane xx are coupled and the synthesis is completed as described in Example 8 to give intermediate xliii via intermediate xlii. Dihydropyrimidinone xliii (80 mg, 0.21 mmol) is then treated with 10% methanolic hydrochloric acid (10 mL) at 10° C. for 30 minutes. The solvent is removed under vacuum at 45° C., and the residue is dissolved in methyl tert-butyl ether. The resultant solid is filtered and dried to give 97 (38 mg, 0.09 mmol) as a brown solid in 44% yield. MS: m/z 377.1.

Bromide xli is also used to synthesize the compound 91 (shown in Table 10) by following the procedures described in the foregoing Example, followed by methylation as described in Example 9. MS: m/z 391.3.

TABLE 10

| # | Structure and Name |
|---|---|
| 91 | 6-(6-(1-isopropyl-1H-pyrazol-3-yl)imidazo[2,1-b]thiazol-5-yl)-3-methylquinazolin-4(3H)-one |

Example 16: Synthesis of 5-bromo-6-(1-cyclopropyl-1H-pyrazol-3-yl)imidazo[2,1-b]oxazole (xlviii)

To a solution of bromoacetaldehyde dimethyl acetal (5 g, 29.6 mmol) in water (30 mL) is added HCl (6 M, 10 mL). The mixture is heated to 60° C. for 1 hour, then urea xliv (2.66 g, 44.3 mmol) in water (20 mL) is added. The temperature is increased to 95° C. and the reaction is stirred for 1 hour before cooling to 0° C. The pH is adjusted to between 9 and 10 with aqueous sodium hydroxide, and the mixture is extracted into ethyl acetate. The organic layer is washed with brine, dried over sodium sulfate, and concentrated. The residue is purified by flash column chromatography (3%-5% methanol in DCM) to give oxazoline xlv as an off-white solid (900 mg, 10.7 mmol) in 36% yield.

A solution of bromide xxxvii (3 g, 13.0 mmol) and oxazoline xlv (13.1 mmol) in tetrahydrofuran (THF) (30 mL) and acetonitrile (60 mL) is stirred at room temperature for 2 hours, then cooled to 10° C. and stirred for 30 minutes. The resultant solid is filtered, washed with acetonitrile (20 mL) and dried to give hydrobromide salt xlvi (2.6 g, 8.7 mmol) as a white solid in 67% yield.

A solution of hydrobromide salt xlvi (3.2 g, 10.7 mmol) in toluene (70 mL) is cooled to 0° C., then neat titanium tetrachloride (5.7 mL, 51.9 mmol) is added over 15 minutes. The mixture is heated to 110° C. for 10 hours, then cooled to 10° C. and the solution adjusted to pH 9.0 by addition of 10% aqueous sodium carbonate. The mixture is stirred for 1 hour, then extracted into ethyl acetate. The organic layer is washed with brine, dried over sodium sulfate and concentrated. The residue is purified by flash column chromatography (2%-5% methanol in DCM) to give oxazoline xlvii (2.0 g, 9.3 mmol) as a brown solid in 87% yield.

A solution of oxazoline xlvii (500 mg, 2.4 mmol) in chloroform (15 mL) is cooled to −10° C., and N-bromosuccinimide (NBS) (331 mg, 1.9 mmol) is added over 5 minutes and the reaction is stirred at −10° C. for 15 hours. The reaction is quenched with aqueous sodium bicarbonate and stirred at −10° C. for a further 15 minutes, after which DCM is added and the layers are separated. The aqueous layer is extracted into DCM and the combined organic layers are dried over sodium sulfate, filtered through cotton, and the product is distilled at 50° C. to give 480 mg of bromide xlviii, in 70% yield.

Example 17: Synthesis of 6-{7-(1-cyclopropyl-1H-pyrazol-3-yl)-4-oxa-1,6-diazabicyclo[3.3.0]octa-2,5,7-trien-8-yl}-3H-quinazolin-4-one (24)

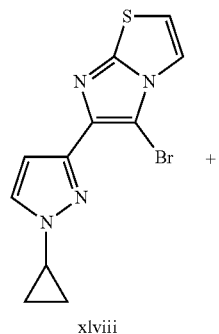

xlviii

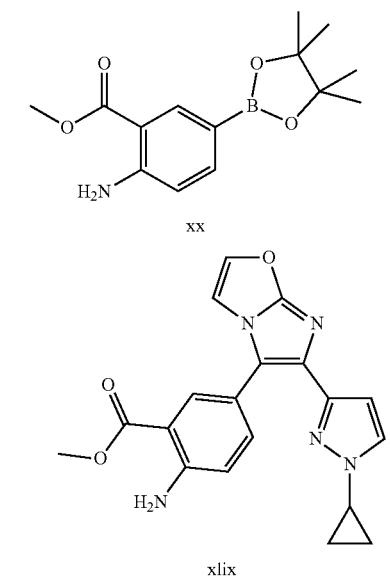

Bromide xlviii and dioxaborolane xx are subjected to the conditions described for the synthesis of Example 8 to give 24 as a brown solid in 7% yield via intermediate ester xlix. MS: m/z 357.2.

Example 18: Synthesis of 6-{7-(1-cyclopropyl-1H-pyrazol-3-yl)-4-oxa-1,6-diazabicyclo[3.3.0]octa-2,5,7-trien-8-yl}-3-methyl-3H-quinazolin-4-one (26)

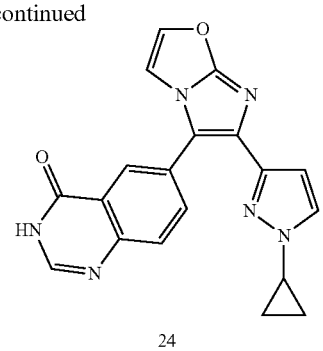

24

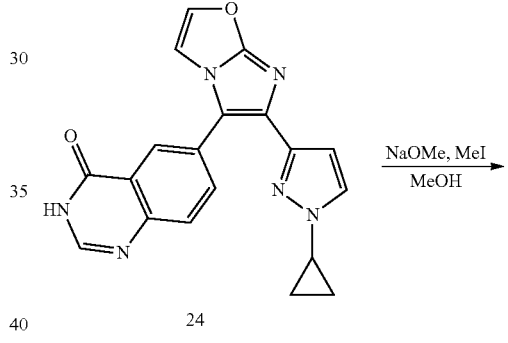

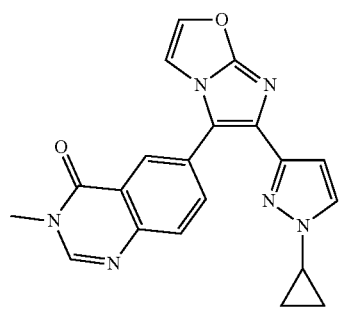

26

Once the synthesis of 24 is completed, it is further elaborated using the methods described in Example 9 to provide 26 as a white solid in 19% yield. MS m/z 373.1.

Other compounds that are synthesized using the methods described in Examples 16, 17, and 18 are shown below in Table 11.

TABLE 11

| # | Structure and Name | Physical Data (MS, m/z M + 1) |
|---|---|---|
| 23 | 6-{7-(1-Isopropyl-1H-pyrazol-3-yl)-4-oxa-1,6-diazabicyclo[3.3.0]octa-2,5,7-trien-8-yl}-3H-quinazolin-4-one | 361.2 |
| 25 | 6-{7-(1-Isopropyl-1H-pyrazol-3-yl)-4-oxa-1,6-diazabicyclo[3.3.0]octa-2,5,7-trien-8-yl}-3-methyl-3H-quinazolin-4-one | 375.2 |

One of skill in the art will appreciate that the same synthetic techniques may be used to access the compounds shown below in Table 12.

TABLE 12

| # | Structure and Name |
|---|---|
| 5 | 8-(1,3a-Diaza-5-indenyl)-7-(1-isopropyl-1H-pyrazol-3-yl)-4-oxa-1,6-diazabicyclo[3.3.0]octa-2,5,7-triene |
| 6 | 8-(1,3a-Diaza-5-indenyl)-7-(1-cyclopropyl-1H-pyrazol-3-yl)-4-oxa-1,6-diazabicyclo[3.3.0]octa-2,5,7-triene |
| 11 | 5-{7-(1-Isopropyl-1H-pyrazol-3-yl)-4-oxa-1,6-diazabicyclo[3.3.0]octa-2,5,7-trien-8-yl}-1,3a-diaza-3-indenecarboxamide |
| 12 | 5-{7-(1-Cyclopropyl-1H-pyrazol-3-yl)-4-oxa-1,6-diazabicyclo[3.3.0]octa-2,5,7-trien-8-yl}-1,3a-diaza-3-indenecarboxamide |
| 31 | 6-{7-(1-Isopropyl-1H-pyrazol-3-yl)-4-oxa-1,6-diazabicyclo[3.3.0]octa-2,5,7-trien-8-yl}-3-(2-morpholinoethyl)-3H-quinazolin-4-one |
| 32 | 6-{7-(1-Cyclopropyl-1H-pyrazol-3-yl)-4-oxa-1,6-diazabicyclo[3.3.0]octa-2,5,7-trien-8-yl}-3-(2-morpholinoethyl)-3H-quinazolin-4-one |
| 37 | 6-{7-(1-Isopropyl-1H-pyrazol-3-yl)-4-oxa-1,6-diazabicyclo[3.3.0]octa-2,5,7-trien-8-yl}-3-[2-(1-pyrrolidinyl)ethyl]-3H-quinazolin-4-one |

TABLE 12-continued

| # | Structure and Name |
|---|---|
| 38 | 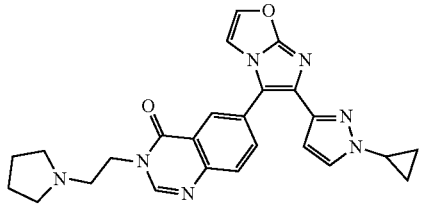 [SMILES: O=c1c2cc(-c3c(-c4ccn(C5CC5)n4)nc4occn34)ccc2ncn1CCN1CCCC1]<br>6-{7-(1-Cyclopropyl-1H-pyrazol-3-yl)-4-oxa-1,6-diazabicyclo[3.3.0] octa-2,5,7-trien-8-yl}-3-[2-(1-pyrrolidinyl)ethyl]-3H-quinazolin-4-one |
| 45 | 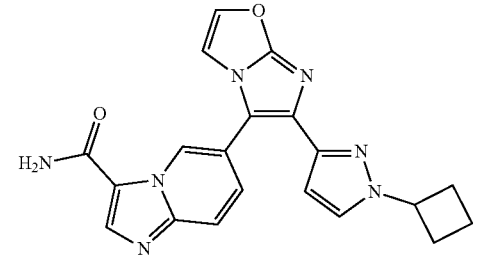 [SMILES: NC(=O)c1cnc2ccc(-c3c(-c4ccn(C5CCC5)n4)nc4occn34)cn12]<br>5-{7-(1-Cyclobutyl-1H-pyrazol-3-yl)-4-oxa-1,6-diazabicyclo[3.3.0] octa-2,5,7-trien-8-yl}-1,3a-diaza-3-indenecarboxamide |
| 73 | 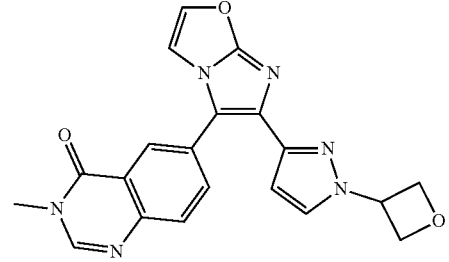 [SMILES: Cn1cnc2ccc(-c3c(-c4ccn(C5COC5)n4)nc4occn34)cc2c1=O]<br>3-methyl-6-(6-(1-(oxetan-3-yl)-1H-pyrazol-3-yl)imidazo[2,1-b]oxazol-5-yl)quinazolin-4(3H)-one |
| 76 | 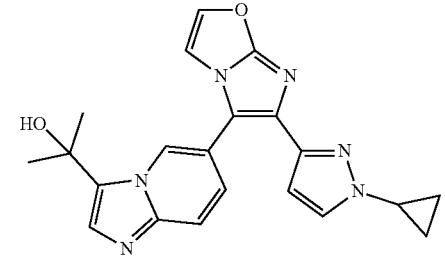<br>2-(6-(6-(1-cyclopropyl-1H-pyrazol-3-yl)imidazo[2,1-b]oxazol-5-yl)imidazo[1,2-a]pyridin-3-yl)propan-2-ol |
| 80 | 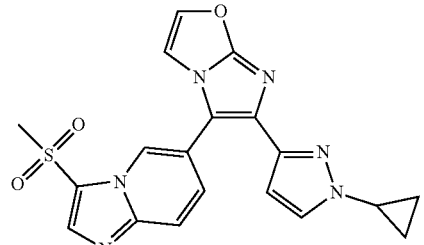<br>6-(1-cyclopropyl-1H-pyrazol-3-yl)-5-(3-(methylsulfonyl)imidazo[1,2-a]pyridin-6-yl)imidazo[2,1-b]oxazole |

Example 19: Synthesis of 1-(5-bromo-6-(1-cyclopropyl-1H-pyrazol-3-yl)-2,3-dihydro-1H-imidazo[1,2-a]imidazol-1-yl)ethan-1-one (liii)

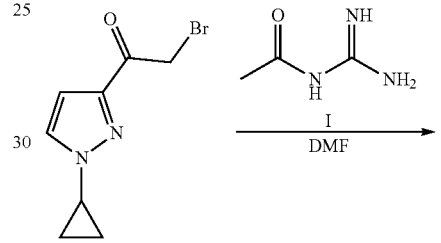

xxxvii

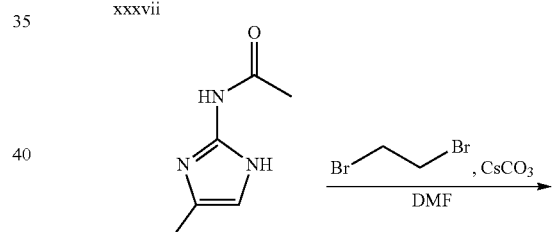

li

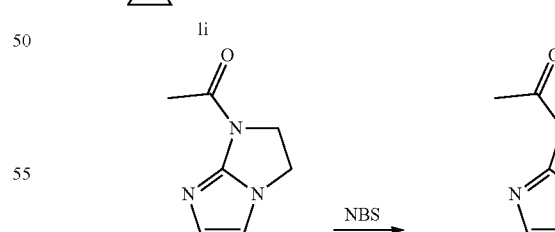

lii     liii

To a solution of bromide xxxvii (10 g, 43.5 mmol) in dimethylformamide (DMF) (60 mL) is added N-acetylguanine 1 (13.1 g, 129.7 mmol), and the reaction is stirred for 20 hours. The mixture is poured onto water and extracted into ethyl acetate. The organic layer is washed with brine, dried over sodium sulfate, and concentrated. The residue is purified by flash column chromatography (3%-5% methanol in DCM) to give amide li (4.2 g, 18.2 mmol) in 42% yield.

Amide li (500 mg, 2.2 mmol) is dissolved in DMF (5 mL) and cesium carbonate (3.5 g, 10.8 mmol) is added. The mixture is stirred for 30 minutes, after which 1,2-dibromoethane (0.56 mL, 6.5 mmol) is added. The mixture is heated to 100° C. for 6 hours, then cooled to room temperature before adding water. The mixture is extracted into ethyl acetate, and the organic layer is dried over sodium sulfate and concentrated. The residue was purified by flash column chromatography (3%-6% methanol in DCM) to give amide lii (180 mg, 0.70 mmol) in 32% yield.

To a solution of imidazoline lii (500 mg, 1.9 mmol) in chloroform (15 mL) is added N-bromosuccinimide (277 mg, 1.6 mmol) in three portions at −10° C. The reaction is stirred at −5° C. for 1 hour, then poured into a 10% aqueous sodium bicarbonate solution and extracted into DCM. The organic layer is washed with brine, dried over sodium sulfate, and concentrated. The residue was purified by flash column chromatography (3%-5% methanol in DCM) to give bromide liii (400 mg, 1.2 mmol) in 63% yield.

Example 20: Synthesis of 3-methyl-6-(4,4,5,5-tetramethyl-1,3,2-dioxaborolan-2-yl)quinazolin-4(3H)-one (xxxiii)

A solution of bromide xix (100 g, 0.43 mol) in formamide (2 L) is heated to 60° C. for 24 hours. The mixture is then cooled to 0° C. to permit formation of a solid. Isopropanol is added, and the mixture is stirred for 30 minutes. The solid is filtered and washed with isopropanol to give bromide liv (60 g, 0.27 mol) which is used without further purification.

A solution of sodium methoxide (7.2 g, 0.13 mol) in methanol (200 mL) is cooled to 0° C., then bromide liv (10 g, 0.04 mol) is added, followed by methyl iodide (5.5 mL, 0.09 mol). The reaction is allowed to warm to room temperature and is stirred for 12 hours. The mixture is concentrated under vacuum, and the residue is diluted with water and extracted into DCM. The organic layer is dried over sodium sulfate and concentrated. The residue was purified by flash column chromatography (2% methanol in DCM) to give methylquinazolinone lv (8 g, 0.03 mol) in 75% yield.

A solution of methylquinazolinone lv (2 g, 8.4 mmol) in 1,4-dioxane (60 mL) is degassed under nitrogen for 10 minutes. Potassium acetate (2.8 g, 28.6 mmol), bis(pinacolato)diboron (2.5 g, 9.9 mmol), and [1,1′-bis(diphenylphosphino)ferrocene]dichloropalladium(II) (Pd(dppf)Cl$_2$) (600 mg, 0.82 mmol) are added. The reaction is heated to 120° C. for 12 hours, then cooled to room temperature, and the solid removed by filtration. The filtrate is concentrated, and the residue is purified by flash column chromatography (10% methanol in DCM) to give dioxaborolane xxxiii (1.5 g, 5.2 mmol) in 62% yield.

Example 21: Alternative synthesis of 6-{3-(1-cyclopropyl-1H-pyrazol-3-yl)-1,4-diazabicyclo[3.3.0]octa-2,4-dien-2-yl}-3-methyl-3H-quinazolin-4-one (18)

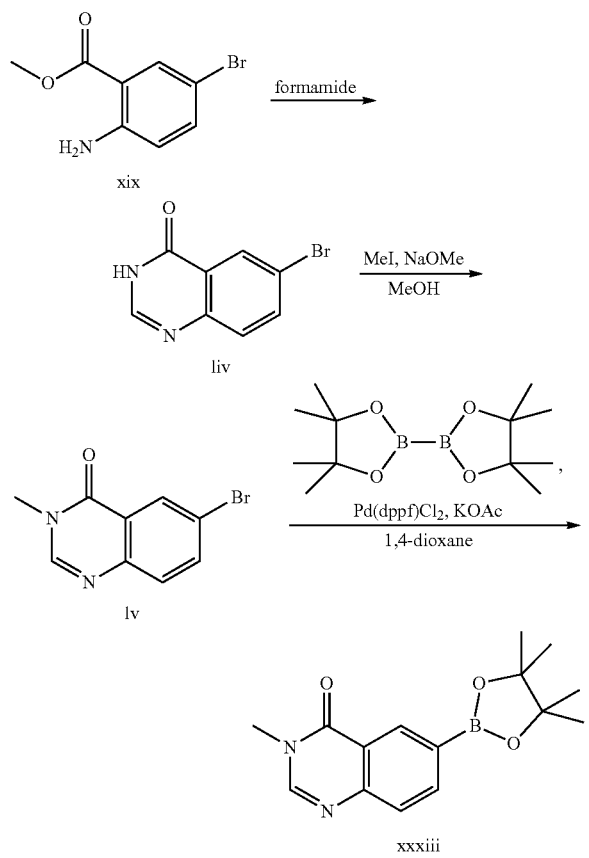

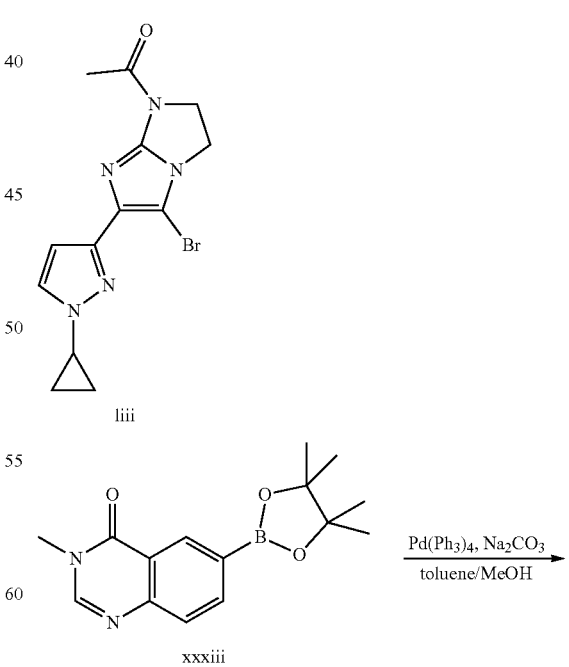

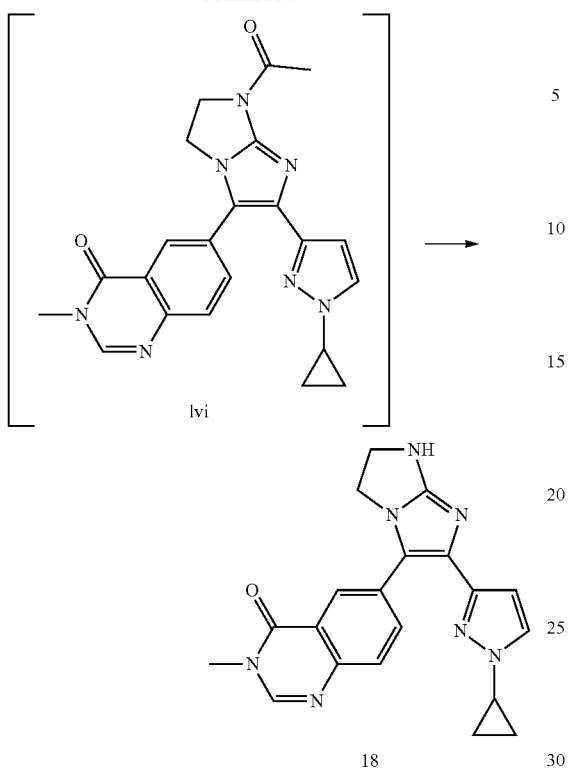

Bromide liii (200 mg, 0.59 mmol) and dioxaborolane xxxiii (222 mg, 0.69 mmol) are dissolved in toluene (12 mL) and methanol (6 mL) and the mixture is degassed under nitrogen for 10 minutes. Sodium carbonate (189 mg, 1.78 mmol) and tetrakis(triphenylphosphine) palladium (138 mg, 0.12 mmol) are added. The reaction is heated to 120° C. for 12 hours, then concentrated under vacuum. The residue is purified by flash column chromatography (3%-6% methanol in DCM) to give 18 (12 mg, 0.05 mmol) as a brown solid in 8% yield. MS: m/z 374.

The synthetic method described in Example 21, in conjunction with the foregoing example, may be used to synthesize the compounds shown below in Table 13.

TABLE 13-continued

| # | Structure and Name |
|---|---|
| 20 | 6-{3-(1-Cyclopropyl-1H-pyrazol-3-yl)-1,4,6-triazabicyclo[3.3.0]octa-2,4-dien-2-yl}-3H-quinazolin-4-one |
| 21 | 6-{3-(1-Isopropyl-1H-pyrazol-3-yl)-1,4,6-triazabicyclo[3.3.0]octa-2,4-dien-2-yl}-3-methyl-3H-quinazolin-4-one |
| 22 | 6-{3-(1-Cyclopropyl-1H-pyrazol-3-yl)-1,4,6-triazabicyclo[3.3.0]octa-2,4-dien-2-yl}-3-methyl-3H-quinazolin-4-one |
| 35 | 6-{3-(1-Isopropyl-1H-pyrazol-3-yl)-1,4,6-triazabicyclo[3.3.0]octa-2,4-dien-2-yl}-3-(2-morpholinoethyl)-3H-quinazolin-4-one |
| 36 | 6-{3-(1-Cyclopropyl-1H-pyrazol-3-yl)-1,4,6-triazabicyclo[3.3.0]octa-2,4-dien-2-yl}-3-(2-morpholinoethyl)-3H-quinazolin-4-one |
| 41 | 6-{3-(1-Isopropyl-1H-pyrazol-3-yl)-1,4,6-triazabicyclo[3.3.0]octa-2,4-dien-2-yl}-3-[2-(1-pyrrolidinyl)ethyl]-3H-quinazolin-4-one |
| 42 | 6-{3-(1-Cyclopropyl-1H-pyrazol-3-yl)-1,4,6-triazabicyclo[3.3.0]octa-2,4-dien-2-yl}-3-[2-(1-pyrrolidinyl)ethyl]-3H-quinazolin-4-one |
| 44 | 5-{3-(1-Cyclobutyl-1H-pyrazol-3-yl)-1,4,6-triazabicyclo[3.3.0]octa-2,4-dien-2-yl}-1,3a-diaza-3-indenecarboxamide |

TABLE 13-continued

| # | Structure and Name |
|---|---|
| 64 | 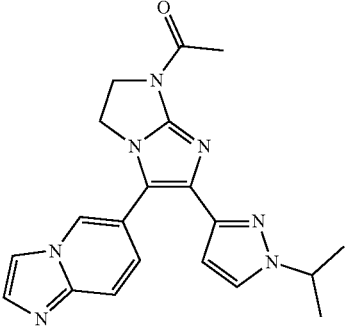
1-(5-(Imidazo[1,2-a]pyridin-6-yl)-6-(1-isopropyl-1H-pyrazol-3-yl)-2,3-dihydro-1H-imidazo[1,2-a]imidazol-1-yl)ethan-1-one |
| 65 | 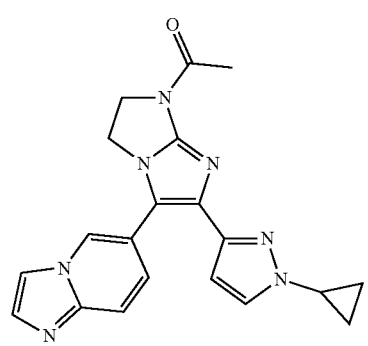
1-(6-(1-Cyclopropyl-1H-pyrazol-3-yl)-5-(imidazo[1,2-a]pyridin-6-yl)-2,3-dihydro-1H-imidazo[1,2-a]imidazol-1-yl)ethan-1-one |
| 66 | 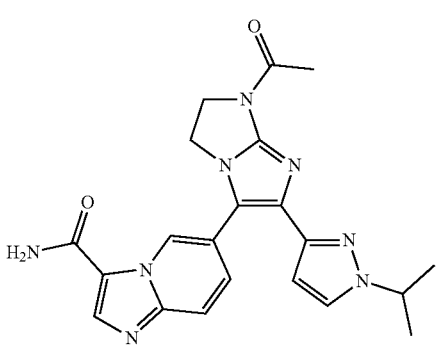
6-(1-Acetyl-6-(1-isopropyl-1H-pyrazol-3-yl)-2,3-dihydro-1H-imidazo[1,2-a]imidazol-5-yl)imidazo[1,2-a]pyridine-3-carboxamide |
| 67 | 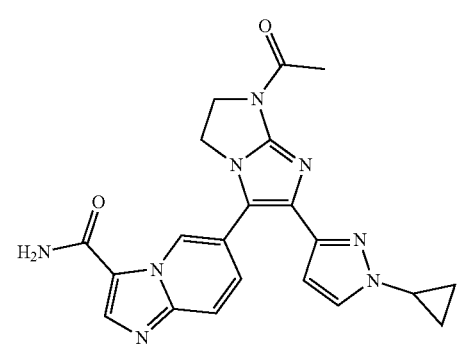
5-{6-Acetyl-3-(1-cyclopropyl-1H-pyrazol-3-yl)-1,4,6-triazabicyclo[3.3.0]octa-2,4-dien-2-yl}-1,3a-diaza-3-indenecarboxamide |
| 68 | 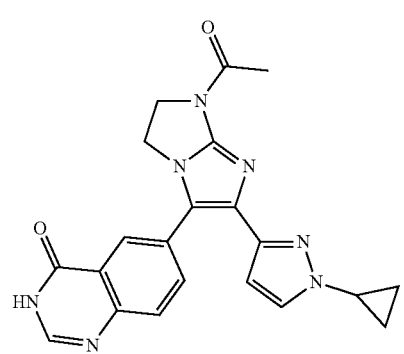
7-(1-acetyl-6-(1-cyclopropyl-1H-pyrazol-3-yl)-2,3-dihydro-1H-imidazo[1,2-a]imidazol-5-yl)isoquinolin-1(2H)-one |
| 69 | 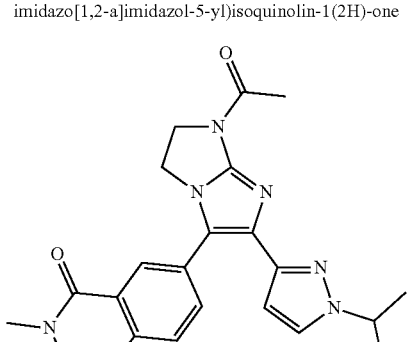
6-(1-acetyl-6-(1-isopropyl-1H-pyrazol-3-yl)-2,3-dihydro-1H-imidazo[1,2-a]imidazol-5-yl)-3-methylquinazolin-4(3H)-one |
| 70 | 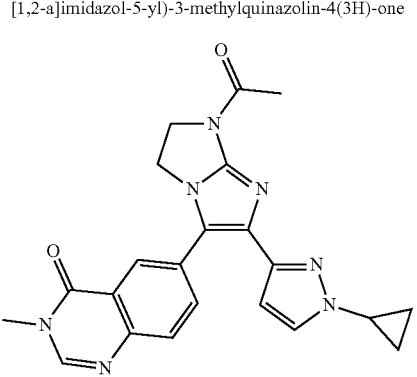
6-(1-acetyl-6-(1-cyclopropyl-1H-pyrazol-3-yl)-2,3-dihydro-1H-imidazo[1,2-a]imidazol-5-yl)-3-methylquinazolin-4(3H)-one |
| 71 | 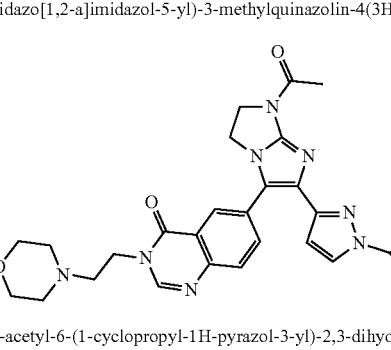
6-(1-acetyl-6-(1-cyclopropyl-1H-pyrazol-3-yl)-2,3-dihydro-1H-imidazo[1,2-a]imidazol-5-yl)-3-(2-morpholinoethyl)quinazolin-4(3H)-one |

TABLE 13-continued

| # | Structure and Name |
|---|---|
| 78 | 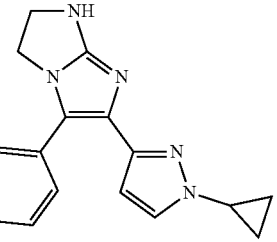<br>2-(6-(6-(1-cyclopropyl-1H-pyrazol-3-yl)-2,3-dihydro-1H-imidazo[1,2-a]imidazol-5-yl)imidazo[1,2-a]pyridin-3-yl)propan-2-ol |
| 82 | 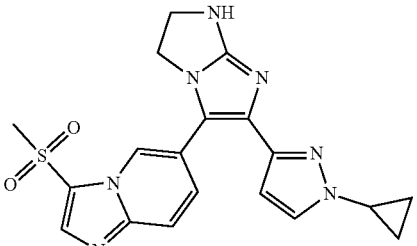<br>6-(6-(1-cyclopropyl-1H-pyrazol-3-yl)-2,3-dihydro-1H-imidazo[1,2-a]imidazol-5-yl)-3-(methylsulfonyl)imidazo[1,2-a]pyridine |

Example 22: Synthesis of 4-(4-(2-(1-cyclopropyl-1H-pyrazol-3-yl)-6,7-dihydro-5H-pyrrolo[1,2-a]imidazol-3-yl)pyridin-2-yl)-N-(tetrahydro-2H-pyran-4-yl)benzamide (88)

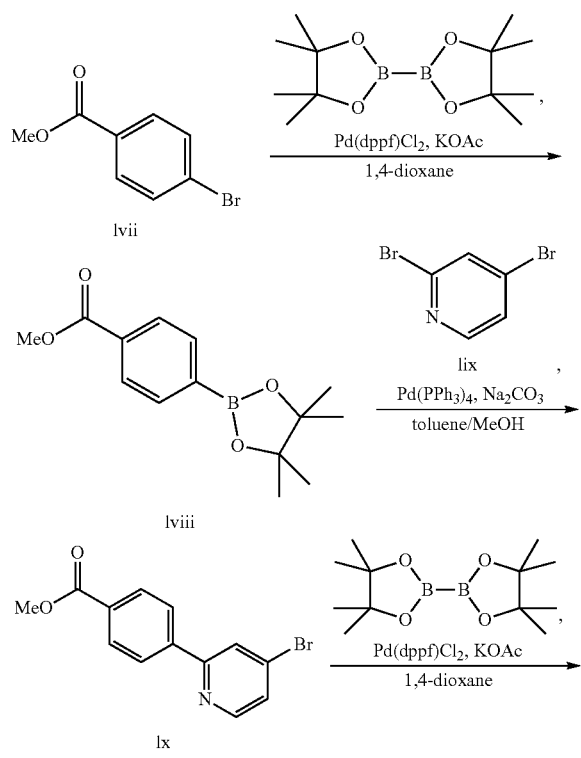

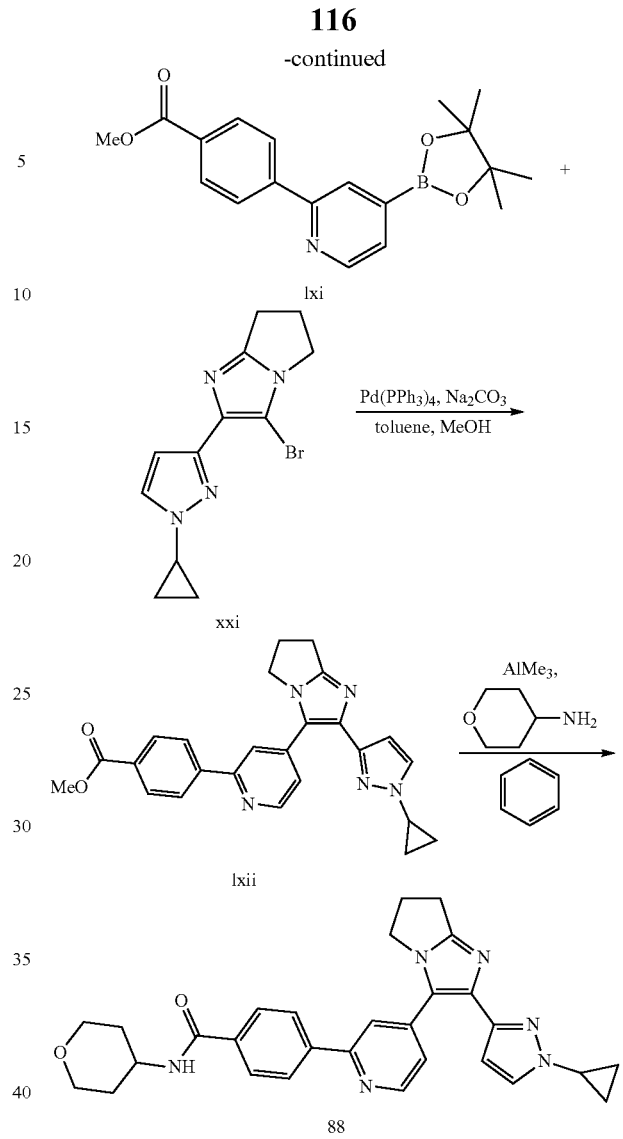

A solution of bromide lvii (5 g, 23.3 mmol) in 1,4-dioxane (150 mL) is degassed under nitrogen atmosphere for 10 minutes. Potassium acetate (8 g, 81.6 mmol), bis(pinacolato)diboron (7 g, 27.6 mmol), and [1,1'-bis(diphenylphosphino)ferrocene]dichloropalladium(II) (Pd(dppf)Cl2) (1.7 g, 2.3 mmol) are added. The mixture is heated to 90° C. for 12 hours, then concentrated under vacuum. The residue is purified by flash column chromatography (15% ethyl acetate in petroleum ether) to give dioxaborolane lviii (4 g, 15.3 mmol) as an off-white solid in 65% yield.

Dioxaborolane lviii (5.3 g, 20.1 mmol) and dibromopyridine lix (4 g, 16.9 mmol) are dissolved in toluene (200 mL) and methanol (120 mL) in a pressure tube. The mixture is degassed under nitrogen atmosphere for 10 minutes, then sodium carbonate (5.3 g, 50.0 mmol) and tetrakis(triphenylphosphine)palladium (1.9 g, 1.7 mmol) are added. The tube is sealed, and the mixture is heated to 110° C. for 12 hours before it is concentrated under reduced pressure. The residue is purified by flash column chromatography (10%-15% ethyl acetate in petroleum ether) to give bromide lx (2.1 g, 7.2 mmol) in 43% yield.

To a solution of bromide lx (1 g, 3.4 mmol) in 1,4-dioxane (30 mL) is added potassium acetate (1.25 g, 12.8 mmol), bis(pinacolato)diboron (1.2 g, 4.7 mmol), and [1,1'-bis(diphenylphosphino)ferrocene]dichloropalladiun(III) (Pd(dppf)Cl2) (250 mg, 0.3 mmol). The mixture is heated to 100° C. for 12 hours, then concentrated under reduced pressure. The residue is purified by flash column chromatography (2% methanol in DCM) to give dioxaborolane lxi (400 mg, 1.2 mmol) as an off-white solid in 35% yield.

A solution of dioxaborolane lxi (752 mg, 2.2 mmol) and bromide xxi (500 mg, 1.7 mmol) in toluene (30 mL) and methanol (15 mL) is degassed under nitrogen atmosphere for 10 minutes. Tetrakis(triphenylphosphine)palladium (395 mg, 0.3 mmol) and sodium carbonate (545 mg, 5.1 mmol) is added. The reaction is heated to 120° C. for 10 hours, then the mixture is concentrated under reduced pressure. The residue is purified by flash column chromatography (2%-5% methanol in DCM) to give ester lxii (220 mg, 0.5 mmol) as a yellow solid in 24% yield.

A solution of tetrahydro-2H-pyran-4-amine (400 mg, 3.96 mmol) in benzene (5 mL) is cooled to 0° C., and trimethyl aluminum (2.0 M in toluene, 2.0 mL) is added. The mixture is warmed to room temperature and stirred for 30 minutes. The solution was titrated to 0.2 M.

To a solution of ester lxii (150 mg, 0.35 mmol) in benzene (10 mL) is added the above described solution of trimethyl aluminum and tetrahydro-2H-pyran-4-amine (0.2 M, 4 mL). The mixture is heated to 80° C. for 5 hours, then cooled to room temperature and 5% aqueous hydrochloric acid is added. The mixture is stirred for 20 minutes, then 10% aqueous sodium bicarbonate is added, and the mixture is extracted into ethyl acetate. The organic layer is dried over sodium sulfate and concentrated, and the residue is purified by flash column chromatography (5% methanol in DCM) to give 88 (26 mg, 0.05 mmol) as a pale yellow solid in 15% yield. MS: m/z 495.4.

Example 23: Synthesis of(4-(4-(2-(1-cyclopropyl-1H-pyrazol-3-yl)-6,7-dihydro-5H-pyrrolo[1,2-a]imidazol-3-yl)pyridin-2-yl)phenyl)(morpholino)methanone (93)

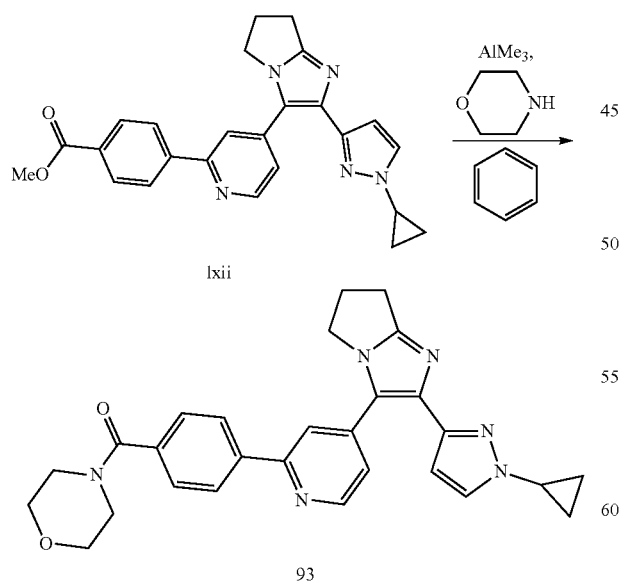

To a solution of ester lxii (100 mg, 0.24 mmol) in benzene (12 mL) is added a 2 M solution of morpholine trimethylaluminum (2 mL, prepared as described above in Example 22 only using morpholine in place of tetrahydro-2H-pyran-4-amine). The mixture is heated to reflux for 5 hours, then cooled to room temperature and 5% aqueous hydrochloric acid is added. The mixture is stirred for 20 minutes, then 10% aqueous sodium bicarbonate is added, and the mixture is extracted into ethyl acetate. The organic layer is dried over sodium sulfate and concentrated, and the residue is purified by flash column chromatography (5% methanol in DCM) to give 93 (21 mg, 0.04 mmol) as a brown solid in 18% yield. MS: m/z 481.3.

Example 24: Synthesis of 2-(1-cyclopropyl-1H-pyrazol-3-yl)-3-(2-(4-(methylsulfonyl)phenyl)pyridin-4-yl)-6,7-dihydro-5H-pyrrolo[1,2-a]imidazole (86)

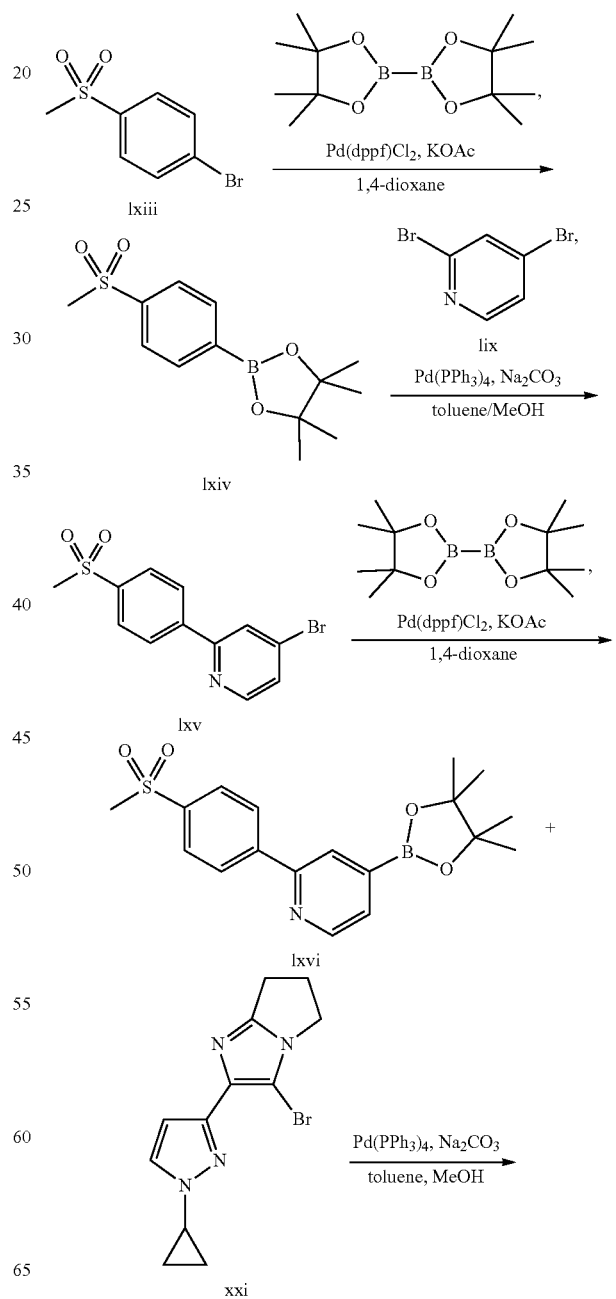

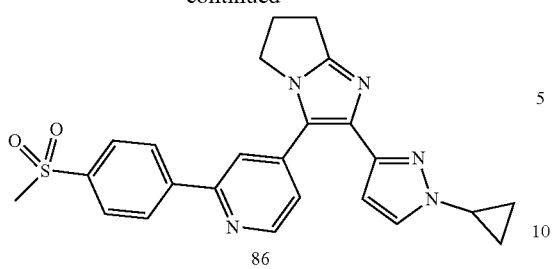

Bromide lxiii is treated as described in Example 22 in the synthesis of lxi to give dioxaborolane lxvi in 12% yield from lxiii. Dioxaborolane lxvi and bromide xxi are then treated as described in Example 5 to give 86 in 12.5% yield from bromide xxi. MS: m/z 446.1.

Example 25: Synthesis of 6-(2-(1-cyclopropyl-1H-pyrazol-3-yl)-6,7-dihydro-5H-pyrrolo[1,2-a]imidazol-3-yl)quinazoline-4-carboxamide (95)

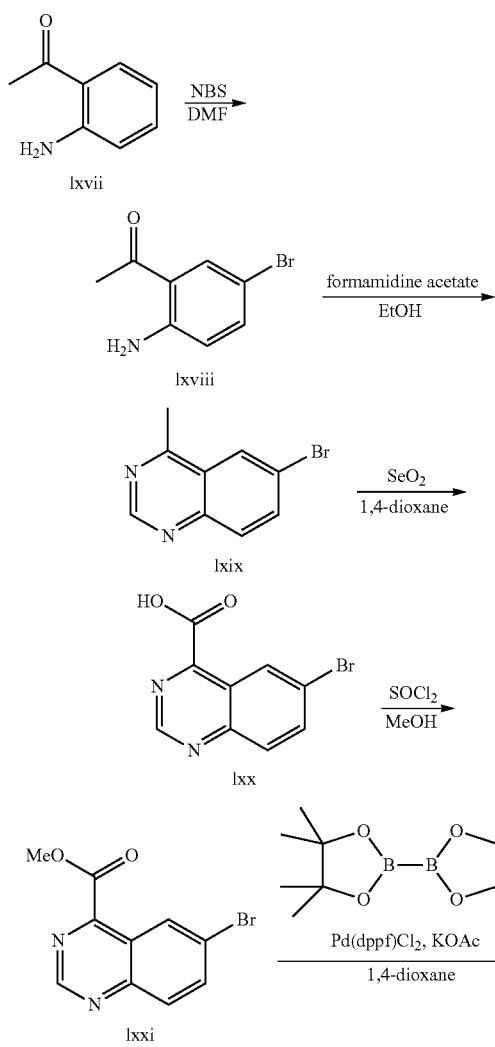

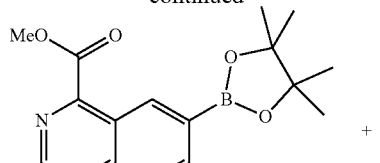

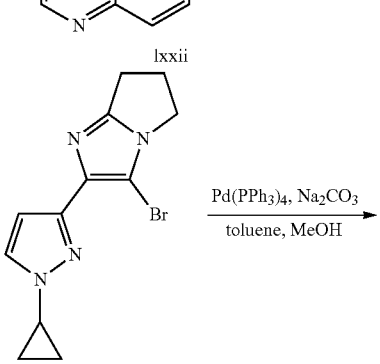

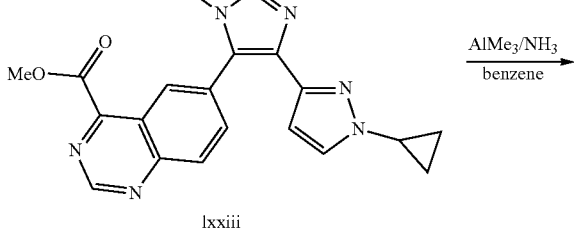

A solution of aniline lxvii (3 g, 17.5 mmol) in DMF (30 mL) is cooled to −10° C., and N-bromosuccinimide (3.12 g, 17.5 mmol) is added. The reaction is allowed to come to room temperature and is stirred for 2 hours, then quenched with 10% aqueous sodium bicarbonate. The mixture is stirred for 30 minutes, and the resultant solid is filtered, washed with water, and dried to give bromide lxvii is used without further purification.

To a solution of bromide lxviii (9 g, 42.0 mmol) in ethanol (270 mL) is added formamidine acetate (9 g, 86.4 mmol). The mixture is heated to 100° C. for 12 hours, then concentrated under vacuum. Aqueous sodium bicarbonate (10%) is added to the residue, and the mixture is extracted into ethyl acetate. The organic layers are dried over sodium sulfate and concentrated. The residue is purified by flash column chromatography (40% ethyl acetate in petroleum ether) to give quinazoline lxix (2.5 g, 11.2 mmol) in 27% yield.

To a solution of quinazoline lxix (2.5 g, 11.2 mmol) in 1,4-dioxane (50 mL) is added selenium dioxide (1.7 g, 15.3 mmol). The mixture is heated to 100° C. for 12 hours, then filtered to remove solids. The filtrate is concentrated under vacuum to give carboxylic acid lxx, which is used without further purification.

A solution of carboxylic acid lxx (500 mg, 1.9 mmol) in methanol (10 mL) is cooled to 10° C., and thionyl chloride (0.44 mL, 6.1 mmol) is added. The mixture is heated to 80° C. for 12 hours, then concentrated under vacuum. The residue is diluted with 10% aqueous sodium bicarbonate and extracted into ethyl acetate. The organic layer is dried over sodium sulfate and concentrated to give methyl ester lxxi, which is used without further purification.

Methyl ester lxxi is then treated as described in Example 24 in the synthesis of dioxaborolane lxiv. Dioxaborolane lxxii and bromide xxi are then treated as described in Example 5 to give methyl ester lxxiii (50 mg, 0.13 mmol) in 12% yield from lxxi.

A solution of ammonium chloride (100 mg, 1.9 mmol) in benzene (5 mL) is cooled to 0° C., and trimethyl aluminum (2.0 M in toluene, 0.93 mL) is added. The mixture is stirred at room temperature for 1 hour, and titrated to 0.15 M.

Methyl ester lxxiii (50 mg, 0.12 mmol) is dissolved in benzene (10 mL). The above described solution of trimethyl aluminum and ammonia (0.15 M, 3 mL) is added and the mixture is heated to 80° C. for 12 hours. The reaction is quenched with 10% aqueous sodium carbonate and the mixture is extracted into DCM. The organic layer is washed with brine, dried over sodium sulfate, and concentrated. The residue is purified by flash column chromatography (3%-6% methanol in DCM) to give 95 (9 mg, 0.02 mmol) as a brown solid in 19% yield. MS: m/z 386.3.

Example 26: Synthesis of 6-(6-(1-cyclopropyl-1H-pyrazol-3-yl)imidazo[2,1-b]thiazol-5-yl)quinazoline-4-carboxamide (96)

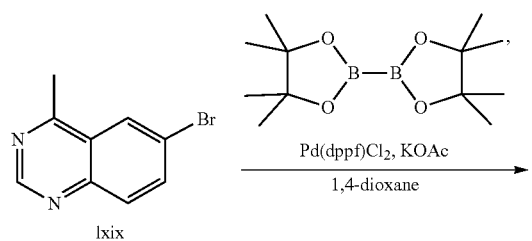

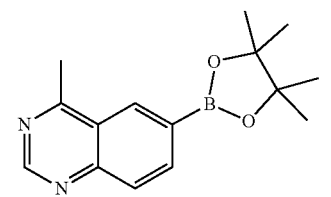

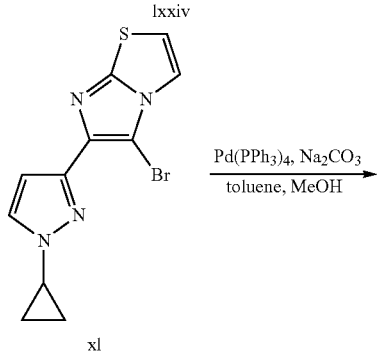

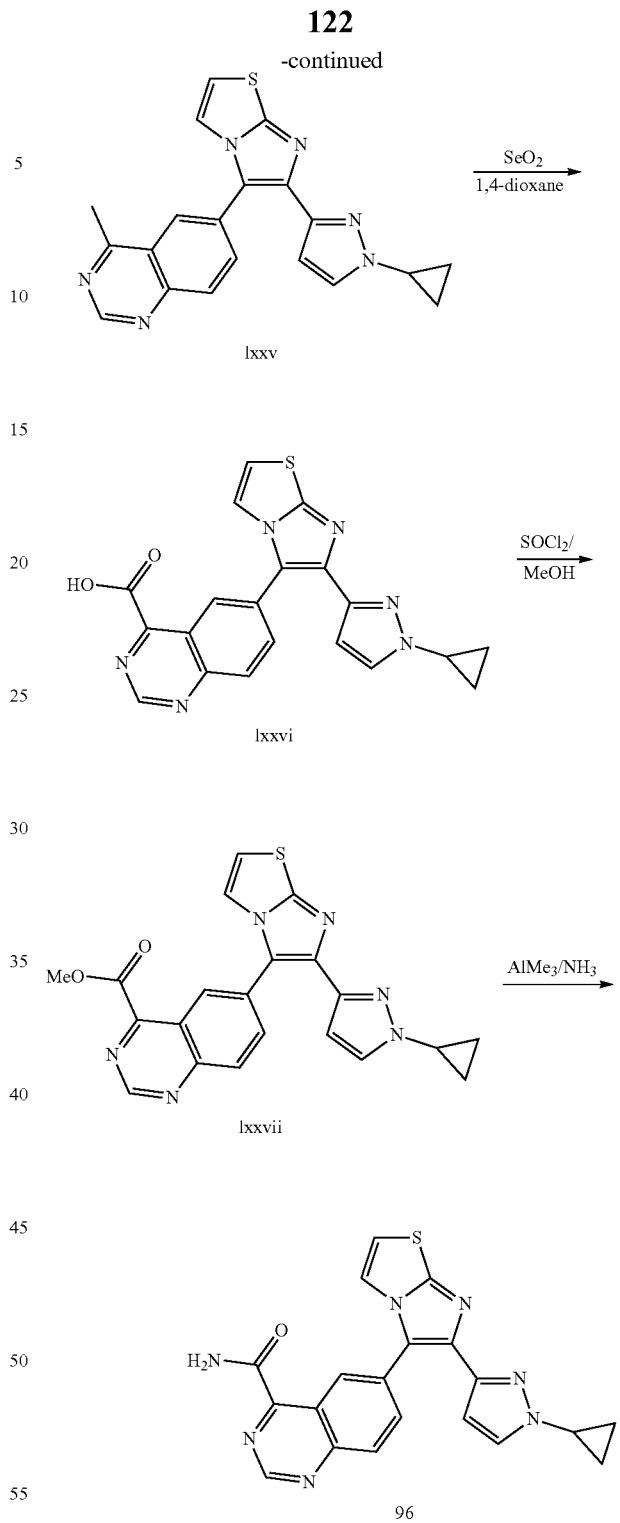

Bromide lxix is treated as described in Example 24 to furnish dioxaborolane lxxiv. Dioxaborolane lxxiv and bromide xl are then coupled as described in Example 5 to give quinazoline lxxv. Quinazoline lxxv is then oxidized with selenium dioxide as described in Example 25 to furnish carboxylic acid lxxvi. Carboxylic acid lxxvi is then derivatized to give methyl ester lxxvii as described in Example 25. Finally, methyl ester lxxvii is treated as described in Example 25 to give 96 (20 mg, 0.05 mmol) as a yellow solid in 21% yield from lxxvii. MS: m/z 402.1.

Example 27: Synthesis of 6-(2-(1-cyclopropyl-1H-pyrazol-3-yl)-6,7-dihydro-5H-pyrrolo[1,2-a]imidazol-3-yl)-4-methoxyquinazoline (98)

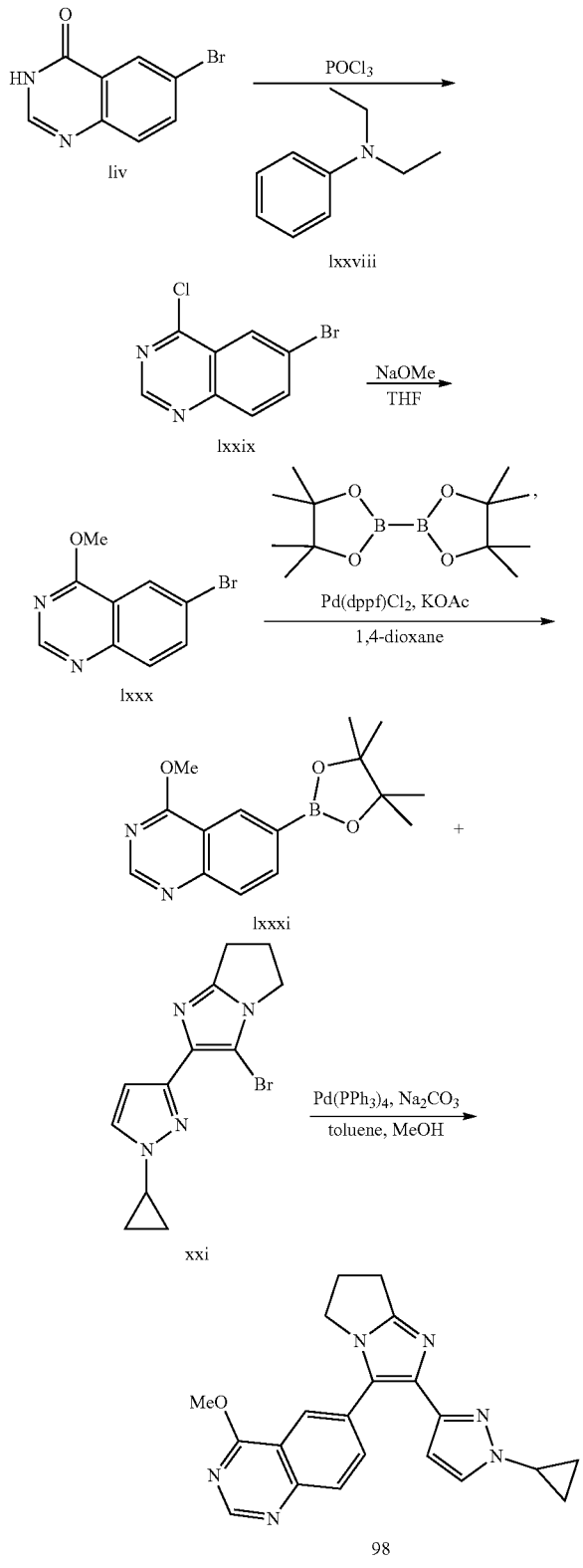

A solution of quinazolinone liv (30 g, 0.13 mol) in phosphorous oxychloride (300 mL) is heated to 95° C. for 1 hour. N,N-Diethylaniline lxxviii (42.2 mL, 0.26 mol) is added slowly, and the mixture is heated to 120° C. for 12 hours. The mixture is concentrated under vacuum, then 10% aqueous sodium bicarbonate is added until the pH reached 7. The mixture is extracted into ethyl acetate, filtered, and concentrated under vacuum. The residue is purified by flash column chromatography (30% ethyl acetate in petroleum ether) to give chloride lxxix (15 g, 0.06 mol) as a yellow solid in 47% yield.

To a solution of chloride lxxix (1 g, 4.1 mmol) in anhydrous tetrahydrofuran (20 mL) is added sodium methoxide (270 mg, 5 mmol). The reaction is stirred for 12 hours, then water is added, and the mixture is extracted into ethyl acetate. The organic layer is washed with brine, dried over sodium sulfate, filtered, and concentrated under vacuum. The residue is purified by flash column chromatography (30% ethyl acetate in petroleum ether) to give methoxide lxxx (700 mg, 2.9 mmol) as an off-white solid in 71% yield.

Methoxide lxxx is treated as described in Example 24 to give dioxaborolane lxxxi in 55% yield. Dioxaborolane lxxxi and bromide xxi are then treated as described in Example 5 to give 98 as a brown solid in 12% yield. MS: m/z 373.3.

Example 28: Synthesis of 1-(1-cyclopropyl-1H-pyrazol-3-yl)ethan-1-one (lxxxiii)

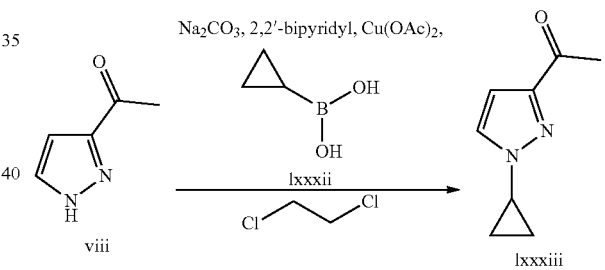

Pyrazole viii (80 g, 0.73 mol) and sodium carbonate (155 g, 1.46 mol) are dissolved in 1,2-dichloroethane (2 L). The mixture is stirred at room temperature for 30 minutes, then 2,2'-bipyridyl (118 g, 0.76 mol) is added, and the reaction is stirred for a further 30 minutes. Copper (II) acetate (150 g, 0.83 mol) is added and the reaction is stirred for 30 minutes prior to adding boronic acid lxxxii (96 g, 1.12 mol). The mixture is heated to 60° C. for 16 hours, then cooled to room temperature. DCM is added and the mixture is filtered through Celite® and washed with DCM. The filtrate is washed with 5% hydrochloric acid (2×1 L), then brine. The product is purified by flash column chromatography (50% ethyl acetate in hexanes) to give cyclopropane lxxxiii (32 g, 0.21 mol) in 29% yield.

Example 29: Synthesis of 6-{7-(1-Cyclopropyl-1H-pyrazol-3-yl)-4-thia-1,6-diazabicyclo[3.3.0]octa-2,5,7-trien-8-yl}-3H-quinazolin-4-one (90)

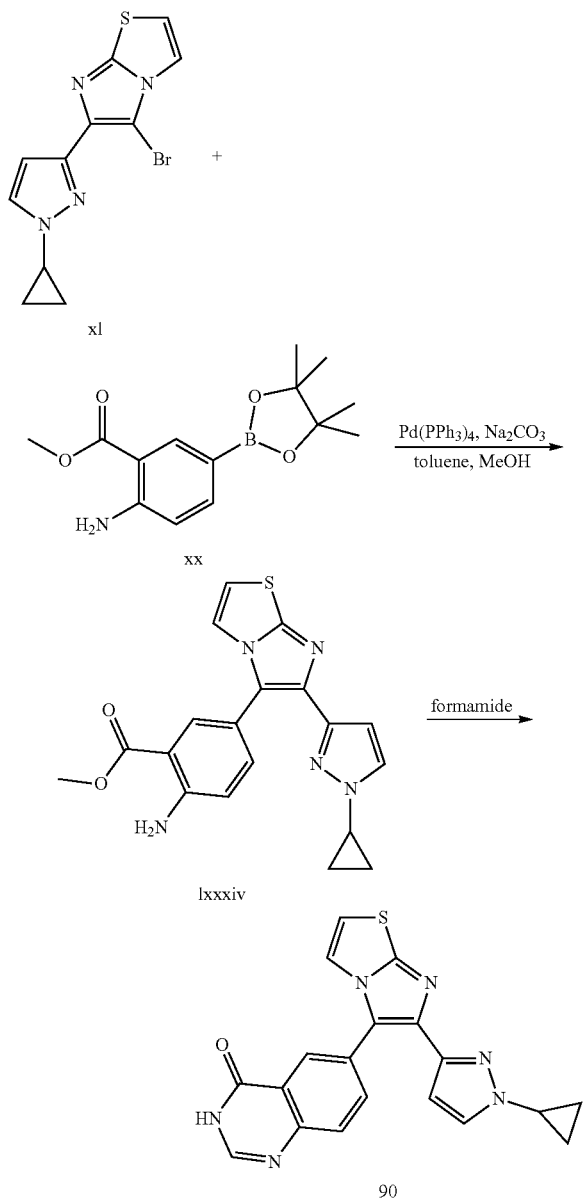

A solution of bromide xl (300 mg, 0.97 mmol) and dioxaborolane xx (298 mg, 1.05 mmol) in methanol (10 mL) and toluene (20 mL) is degassed under nitrogen atmosphere for 10 minutes, then sodium carbonate (308 mg, 2.9 mmol) and tetrakis(triphenylphosphine) palladium (112 mg, 0.1 mmol) are added. The reaction is heated to 100° C. for 12 hours, then 150° C. for 10 hours until the reaction is shown to be complete by thin layer chromatography (TLC). The mixture is cooled to room temperature, filtered through Celite®, and washed with 10% methanol in DCM. The filtrate is concentrated and the residue is purified by flash column chromatography (2%-4% methanol in DCM) to give ester lxxxiv (186 mg, 0.49 mmol) as a brown solid in 51% yield.

A solution of ester lxxxiv (150 mg, 0.40 mmol) in formamide (3 mL) is heated to 150° C. for 5 hours. The mixture is then cooled to room temperature, diluted with water, and extracted into DCM. The organic layer is washed with brine, dried over sodium sulfate, and concentrated. The residue is purified by flash column chromatography (4%-6% methanol in DCM) to give 90 (66 mg, 0.18 mmol) as an off-white solid in 44% yield. MS: m/z 375.1.

Example 30: Synthesis of 6-{7-(1-Cyclopropyl-1H-pyrazol-3-yl)-4-thia-1,6-diazabicyclo[3.3.0]octa-2,5,7-trien-8-yl}-3-methyl-3H-quinazolin-4-one (89)

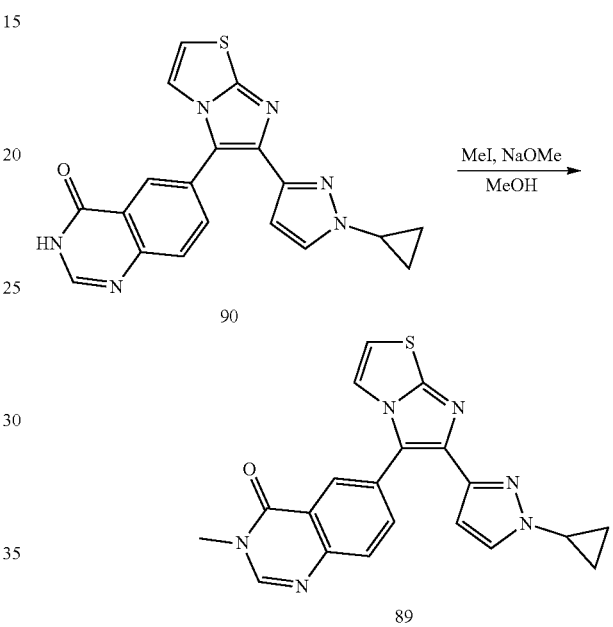

A solution of sodium methoxide (9 mg, 0.17 mmol) in methanol (2 mL) is cooled to 0° C., then 90 (20 mg, 0.05 mmol) and methyl iodide (15 mg, 0.08 mmol) are added. The mixture is stirred at room temperature for 12 hours, then concentrated. Water is added, and the mixture is extracted into DCM. The mixture is concentrated again, then water is added and the mixture is again extracted into DCM. The organic layer is dried over sodium sulfate and concentrated. The residue is purified by flash column chromatography (2%-5% methanol in DCM) to give 89 (7 mg, 0.02 mmol) as a brown solid in 36% yield. MS: m/z 389.1.

One of skill in the art will also appreciate that the synthesis of 89 may be accomplished through a Suzuki coupling, as described in Example 8, using dioxaborolane xxxiii and bromide xl.

It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

As used herein, the term "exemplary" refers to an example or sample. It does not refer to the best of its kind.

As used herein, a "subject" refers to an animal that is the object of treatment, observation or experiment. "Animal" includes cold- and warm-blooded vertebrates and invertebrates, such as fish, shellfish, reptiles, and, in particular, mammals. "Mammal" includes, without limitation, mice; rats; rabbits; guinea pigs; dogs; cats; sheep; goats; cows; horses; primates, such as monkeys, chimpanzees, apes, and prenatal, pediatric, and adult humans.

As used herein, "preventing" or "protecting" means preventing in whole or in part, or ameliorating, or controlling. In certain embodiments, "preventing" or "protecting" refers to delaying the onset of the disease or at least one or more symptoms thereof in a patient which may be exposed to or predisposed to a disease even though that patient does not yet experience or display symptoms of the disease.

"Treating" or "treatment" of any disease refers to therapeutic treatment measures, or administering an agent suspected of having therapeutic potential. In that regard, "treating" or "treatment" refers to reversing, alleviating, arresting, or ameliorating a disease or at least one clinical symptom of a disease, reducing the risk of acquiring at least one clinical symptom of a disease, inhibiting the progress of a disease or at least one clinical symptom of the disease or reducing the risk of developing at least one clinical symptom of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter that may or may not be discernible to the patient. The terms include palliative treatment(s).

The term "a pharmaceutically effective amount", as used herein, means an amount of active compound, or pharmaceutical agent, that elicits the biological, or medicinal, response in a tissue, system, animal, or human that is being sought, which includes alleviation or palliation of the symptoms of the disease being treated and/or an amount sufficient to have utility and provide a desired therapeutic endpoint. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, e.g., by assessing the time to disease progression and/or determining the response rate.

The term "pharmaceutically acceptable", as used herein, may be understood to include that the substance or composition is compatible chemically and/or toxicologically, with the other ingredients comprising a formulation, and/or the mammal being treated therewith.

The term "cancer" may be understood to include the physiological condition in mammals that is typically characterized by unregulated cell growth and/or hyperproliferative activities. A "tumor" may include one or more cancerous cells. Examples of cancer include, but are not limited to, carcinoma, lymphoma, blastoma, sarcoma, and leukemia or lymphoid malignancies. In one embodiment, the cancer is a solid tumor.

More particular examples of such cancers include breast cancer, cervical cancer, ovarian cancer, bladder cancer, endometrial or uterine carcinoma, prostate cancer, glioma and other brain or spinal cord cancers, squamous cell cancer (e.g., epithelial squamous cell cancer), lung cancer, including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, liver cancer, hepatoma, colon cancer, rectal cancer, colorectal cancer, salivary gland carcinoma, kidney or renal cancer, vulval cancer, thyroid cancer, hepatic carcinoma, anal carcinoma, penile carcinoma, as well as head and neck cancer.

What is claimed is:

1. A compound of Formula (I):

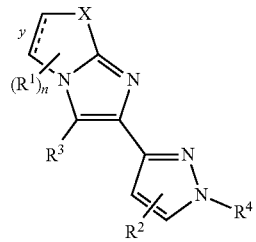

or a pharmaceutically acceptable salt, hydrate, or solvate thereof, wherein:

$R^1$ is:
  a hydrogen atom;
  a halogen atom;
  an alkyl group containing 1 to 6 carbon atoms;
  an alkyl group containing 1 to 6 carbon atoms, substituted with a cycloalkyl group containing 3 to 7 carbon atoms;
  an alkyl group containing 1 to 6 carbon atoms, substituted with 2 to 7 halogens;
  an alkenyl group containing 1 to 6 carbon atoms;
  an alkynyl group containing 1 to 6 carbon atoms;
  a cycloalkyl group containing 3 to 7 carbon atoms;
  a phenyl group;
  a phenyl group substituted with an alkyl group containing 1 to 6 carbons;
  a phenyl group with an alkyl group containing 1 to 6 carbons, optionally further substituted with a hydroxyl group, an alkoxy group containing 1 to 6 carbon atoms, an alkoxy group containing 1 to 6 carbon atoms substituted with an alkoxy group containing 1 to 6 carbon atoms, or an alkoxy group having 1 to 6 carbon atoms substituted with an alkylamino group containing 1 to 6 carbon atoms;
  a carboxylic acid group;
  a carboxylic ester group;
  a carboxamide group; or
  $C(O)R^5$;

$R^2$ is:
  a hydrogen atom;
  a halogen atom;
  an alkyl group containing 1 to 6 carbon atoms;
  an alkyl group containing 1 to 6 carbon atoms, substituted with a cycloalkyl group containing 3 to 7 carbon atoms, or a cycloalkyl group containing 1 to 3 heteroatoms selected from the group consisting of O, N, and S;
  an alkyl group containing 1 to 6 carbon atoms, substituted with 2 to 7 halogens;
  an alkyl group containing 1 to 6 carbon atoms, substituted with 1 to 2 heteroatoms selected from the group consisting of O, N, and S;
  an alkenyl group containing 1 to 6 carbon atoms;
  an alkynyl group containing 1 to 6 carbon atoms;
  a cycloalkyl group containing 3 to 7 carbon atoms;
  a phenyl group; or
  a phenyl group substituted with an alkyl group containing 1 to 6 carbons;

R³ is:
  a phenyl group;
  a phenyl group substituted with 1 to 5 members selected from a group consisting of a halogen, an alkyl group containing 1 to 6 carbon atoms, an alkenyl group containing 1 to 6 carbon atoms, an alkynyl group containing 1 to 6 carbon atoms, an alkoxy group containing 1 to 6 carbon atoms, a phenyl group, a pyridyl group, a hydroxyl group, an amido group, a carbamoyl group, or a cyano group;
  an unsubstituted heteromonocyclic group;
  an unsubstituted heterobicyclic group; or
  a heteromonocyclic or heterobicyclic group substituted with 1 to 5 members selected from the group consisting of a halogen; an alkyl group containing 1 to 6 carbon atoms, optionally substituted with a cycloalkyl group containing 3 to 7 carbon atoms and optionally 1 to 3 heteroatoms selected from the group consisting of O, N, and S; a phenyl group; a pyridyl group; an alkoxy group containing 1 to 6 carbon atoms; a hydroxyl group; a hydroxyalkyl group; an oxo group; an alkylsulfonyl group; an alkylsulfinyl group; an arylsulfonyl group; an arylsulfinyl group; a cycloalkylsulfonyl group; a cycloalkylsulfinyl group; a heterocyclosulfonyl group; a heterocyclosulfinyl group; an amino group; an amido group; a carbamoyl group; a cyano group; an aryl or heteroaryl group substituted with (i) a cycloalkyl group containing 3 to 7 carbon atoms and optionally 1 to 3 heteroatoms selected from the group consisting of O, N, and S, (ii) a primary amide group, (iii) an N-tetrahydropyranyl amide group, (iv) an N,N-dimethyl amide group, (v) a morpholine amide group, (vi) a sulfonyl group, or (vii) a hydroxyalkyl group, wherein the sulfonyl group or hydroxyalkyl group is optionally further substituted with at least one of the group consisting of R⁵ and R⁶; and an alkenyl group containing 1 to 6 carbon atoms, wherein the alkenyl group is optionally further substituted with an amido group;

R⁴ is:
  a hydrogen atom;
  an alkyl group containing 1 to 12 carbon atoms;
  an alkyl group containing 1 to 12 carbon atoms substituted with an alkoxy group containing 1 to 6 carbon atoms, a hydroxyl group, an alkoxyphenylalkoxy group having 8 to 12 carbon atoms, a morpholino group, a piperidinyl group, a pyrrolidino group, or a cyclic ether group containing 3 to 6 carbon atoms;
  an alkyl group having 1 to 6 carbon atoms substituted with 1 to 7 halogen atoms;
  an alkenyl group containing 1 to 6 carbon atoms;
  an alkynyl group containing 1 to 6 carbon atoms;
  a cycloalkyl group containing 3 to 7 carbon atoms;
  a cycloalkyl group containing 3 to 9 carbon atoms substituted with 1 to 7 halogens, or an oxo group;
  a cyclic ether containing 3 to 6 carbon atoms; or
  a 4-piperidinyl group;

R⁵ is:
  an alkyl group having 1 to 6 carbon atoms; a cycloalkyl group containing 3 to 7 carbon atoms optionally substituted with 1 to 7 halogens, an aryl group, or a heteroaryl group;

R⁶ is:
  an alkyl group having 1 to 6 carbon atoms; a cycloalkyl group containing 3 to 7 carbon atoms, an aryl group, or a heteroaryl group;

X is:
  CH₂, O, S, NH, or NC(O)CH₃;
n is:
  0-2; and
the solid and dashed lines at the position denoted y collectively represent:
  a single bond or a double bond.

2. The compound of claim 1, wherein at least one of the following is true:
  R¹ is hydrogen, methyl, hydroxymethyl, carboxyl, acetyl, amido, or fluoro;
  R² is hydrogen, methyl, or fluoro; and
  R⁴ is methyl, isopropyl, cyclopropyl, cyclobutyl, difluoromethyl, 2,2-difluoroethyl, or oxetanyl.

3. The compound of claim 1, wherein R³ is:

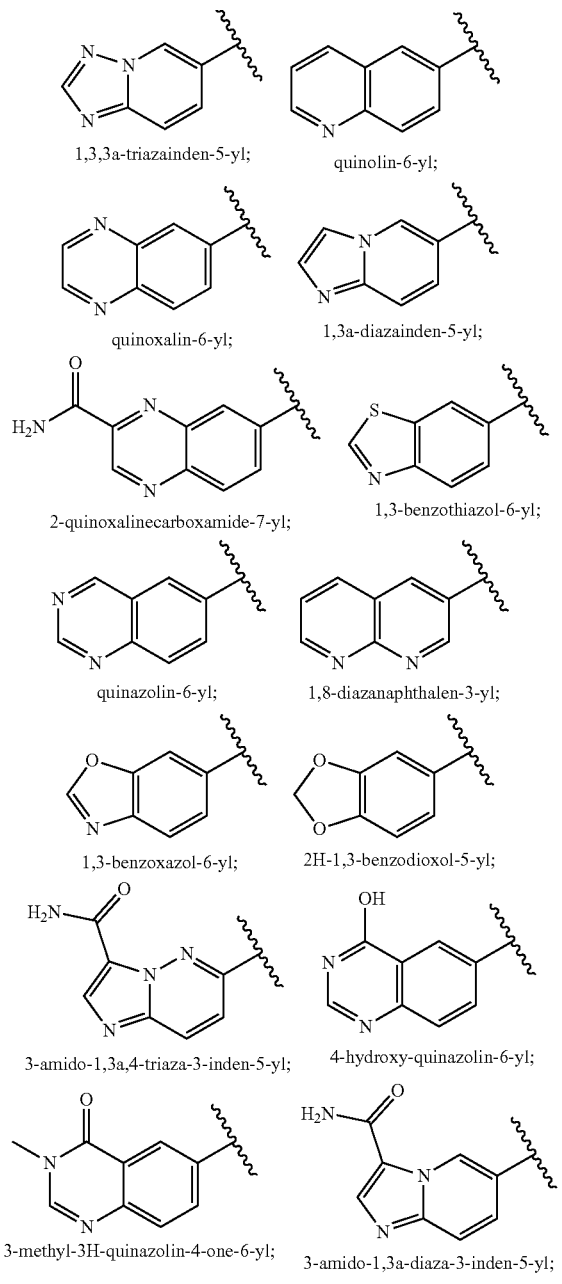

-continued

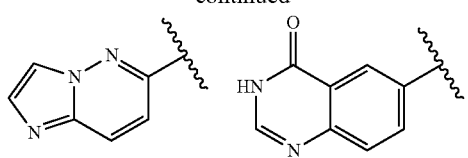

1,3a,4-triazainden-5-yl;   3H-quinazolin-4-one-6-yl;

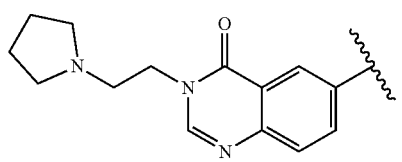

3-(2-(pyrrolidin-1-yl)ethyl)-3H-quinazolin-4-one-6-yl;

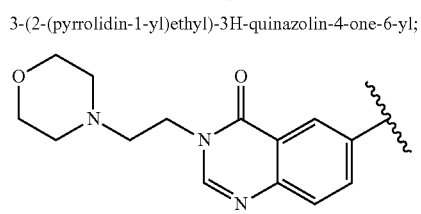

3-(2-morpholinoethyl)-3H-quinazolin-4-one-6-yl;

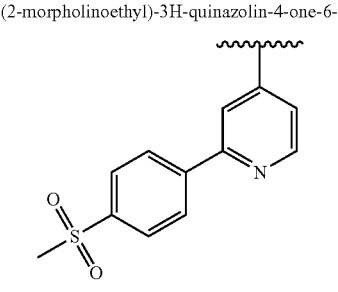

2-[p-(methylsulfonyl)phenyl]pyridin-4-yl;

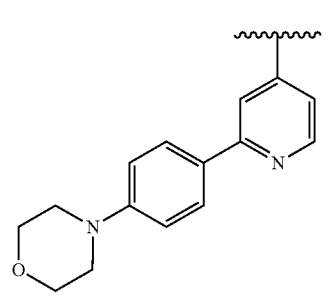

2-[p-(4-morpholinyl)phenyl]pyridin-4-yl;

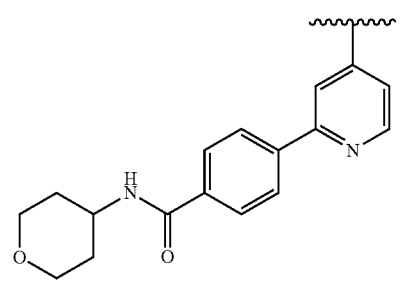

2-[p-[(tetrahydro-2H-pyran-4-ylamino)carbonyl]phenyl]pyridin-4-yl;

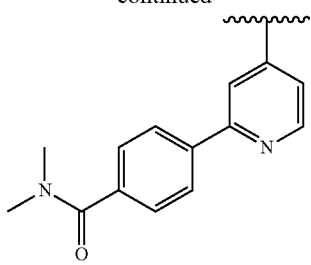

2-[p-[(dimethylamino)carbonyl]phenyl]pyridin-4-yl;

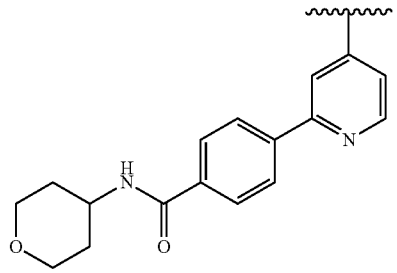

2-[p-[(tetrahydro-2H-pyran-4-ylamino)carbonyl]phenyl]pyridin-4-yl;

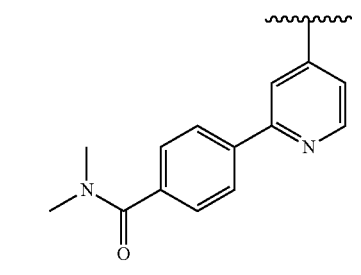

2-[p-[(dimethylamino)carbonyl]phenyl]pyridin-4-yl;

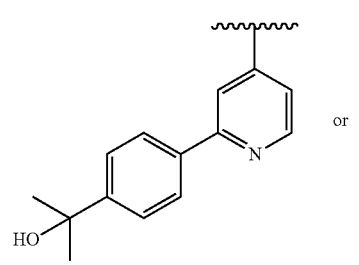

or

2-[p-[1-methyl-1-hydroxy(ethyl)]phenyl]pyridin-4-yl;

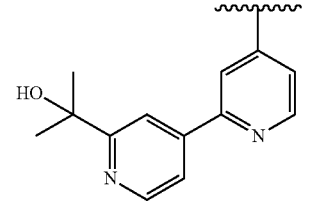

2-[2-[1-methyl-1-hydroxy(ethyl)]pyridin-4-yl]pyridin-4-yl;

-continued

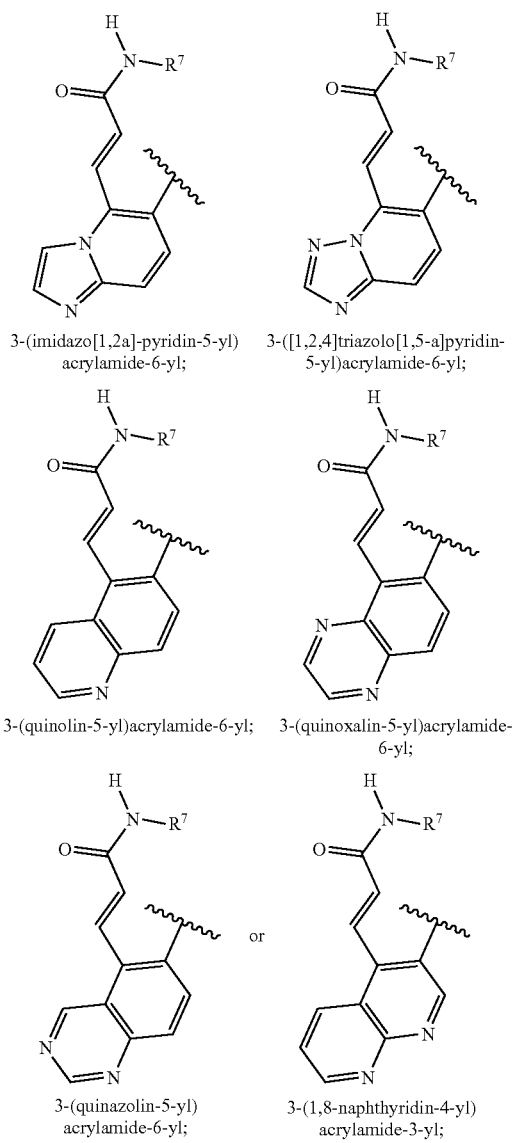

3-(imidazo[1,2a]-pyridin-5-yl) acrylamide-6-yl;

3-([1,2,4]triazolo[1,5-a]pyridin-5-yl)acrylamide-6-yl;

3-(quinolin-5-yl)acrylamide-6-yl;

3-(quinoxalin-5-yl)acrylamide-6-yl;

3-(quinazolin-5-yl) acrylamide-6-yl;

3-(1,8-naphthyridin-4-yl) acrylamide-3-yl;

and $R^7$ is hydrogen, alkyl, cycloalkyl, hydroxyalkyl, aryl or heteroaryl.

4. The compound of claim 1, wherein the compound is:

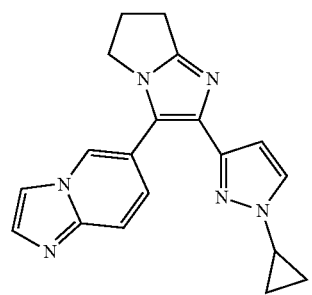

6-(2-(1-isopropyl-1H-pyrazol-3-yl)-6,7-dihydro-5H-pyrrolo[1,2-a]imidazol-3-yl)imidazo[1,2-a]pyridine -continued 3-{2-(1,3a-Diaza-5-indenyl)-1,4-diazabicyclo[3.3.0]octa-2,4-dien-2-yl}-1-cyclopropyl-1H-pyrazole;

6-(6-(1-isopropyl-1H-pyrazol-3-yl)-2,3-dihydro-1H-imidazo[1,2-a]imidazol-5-yl)imidazo[1,2-a]pyridine;

6-(6-(1-cyclopropyl-1H-pyrazol-3-yl)-2,3-dihydro-1H-imidazo[1,2-a]imidazol-5-yl)imidazo[1,2-a]pyridine;

8-(1,3a-Diaza-5-indenyl)-7-(1-isopropyl-1H-pyrazol-3-yl)-4-oxa-1,6-diazabicyclo[3.3.0]octa-2,5,7-triene;

8-(1,3a-Diaza-5-indenyl)-7-(1-cyclopropyl-1H-pyrazol-3-yl)-4-oxa-1,6-diazabicyclo[3.3.0]octa-2,5,7 triene;

-continued

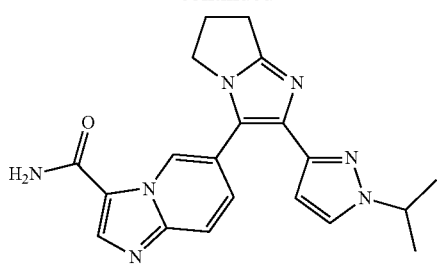

5-{3-(1-Isopropyl-1H-pyrazol-3-yl)-1,4-diazabicyclo[3.3.0]octa-2,4-dien-2-yl}-1,3a-diaza-3-indenecarboxamide;

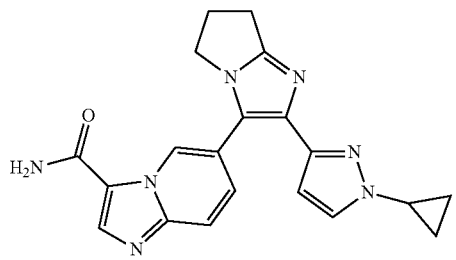

5-{3-(1-Cyclopropyl-1H-pyrazol-3-yl)-1,4-diazabicyclo[3.3.0]octa-2,4-dien-2-yl}-1,3a-diaza-3-indencarboxamide;

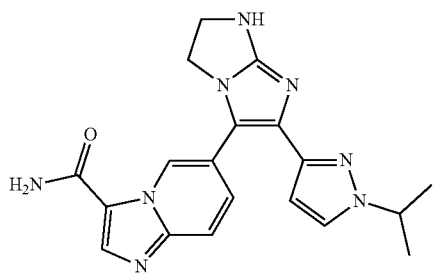

5-{3-(1-Isopropyl-1H-pyrazol-3-yl)-1,4,6-triazabicyclo[3.3.0]octa-2,4-dien-2-yl}-1,3a-diaza-3-indenecarboxamide;

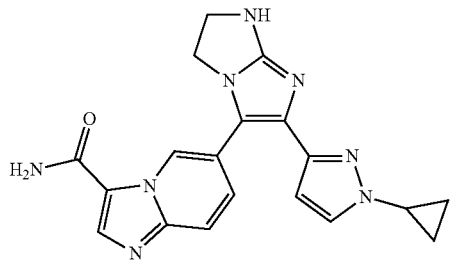 [SMILES: NC(=O)c1cnc2ccc(-c3c(-c4ccn(C5CC5)n4)nc4n3CCN4)cn12]

5-{3-(1-Cyclopropyl-1H-pyrazol-3-yl)-1,4,6-triazabicyclo[3.3.0]octa-2,4-dien-2-yl}-1,3a-diaza-3-indencarboxamide;

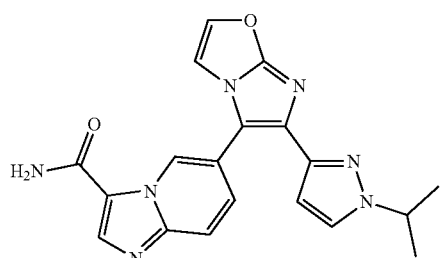

5-{7-(1-Isopropyl-1H-pyrazol-3-yl)-4-oxa-1,6-diazabicyclo[3.3.0]octa-2,5,7-trien-8-yl}-1,3a-diaza-3-indencarboxamide;

-continued

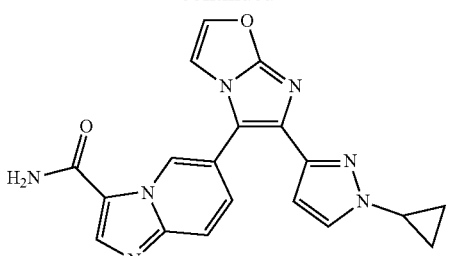

5-{7-(1-Cyclopropyl-1H-pyrazol-3-yl)-4-oxa-1,6-diazabicyclo[3.3.0]octa-2,5,7-trien-8-yl}-1,3a-diaza-3-indencarboxamide;

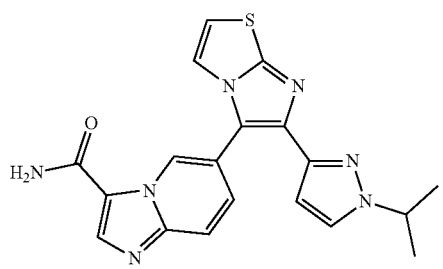

5-{7-(1-Isopropyl-1H-pyrazol-3-yl)-4-thia-1,6-diazabicyclo[3.3.0]octa-2,5,7-trien-8-yl}-1,3a-diaza-3-indenecarboxamide;

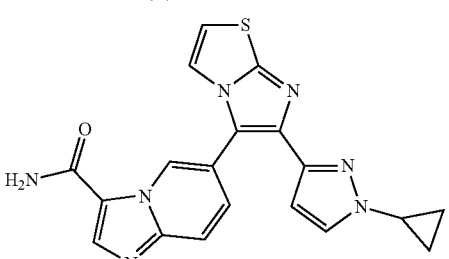

5-{7-(1-Cyclopropyl-1H-pyrazol-3-yl)-4-thia-1,6-diazabicyco[3.3.0]octa-2,5,7-trien-8-yl}-1,3a-diaza-3-indenecarboxamide;

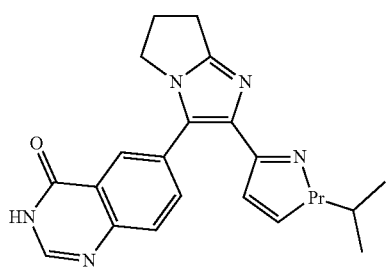

6-{3-(1-Isopropyl-1H-pyrazol-3-yl)-1,4-diazabicyclo[3.3.0]octa-2,4-dien-2-yl}-3H-quinazolin-4-one;

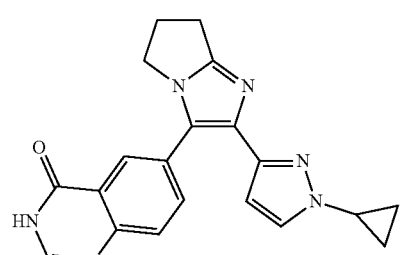

6-{3-(1-Cyclopropyl-1H-pyrazol-3-yl)-1,4-diazabicyclo[3.3.0]octa-2,4-dien-2-yl}-3H-quinazolin-4-one;

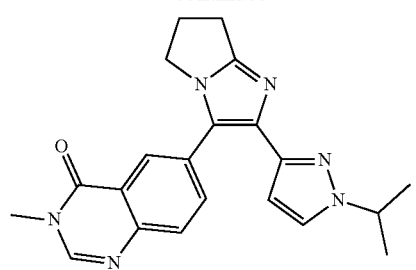

6-{3-(1-Isopropyl-1H-pyrazol-3-yl)-1,4-diazabicyclo[3.3.0]
octa-2,4-dien-2-yl}-3-methyl-3H-quinazolin-4-one;

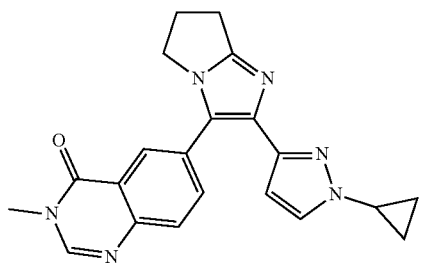

6-{3-(1-Cyclopropyl-1H-pyrazol-3-yl)-1,4-diazabicyclo[3.3.0]
octa-2,4-dien-2-yl}-3-methyl-3H-quinazolin-4-one;

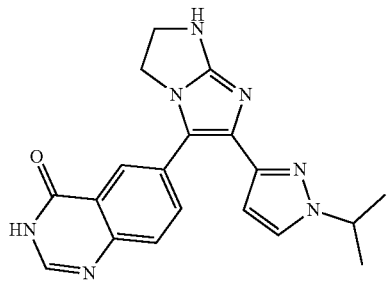 [SMILES: CC(C)n1ccc(-c2nc3n(c2-c2ccc4nc[nH]c(=O)c4c2)CCN3)n1]

6-{3-(1-Isopropyl-1H-pyrazol-3-yl)-1,4,6-triazabicyclo[3.3.0]
octa-2,4-dien-2-yl}-3H-quinazolin-4-one;

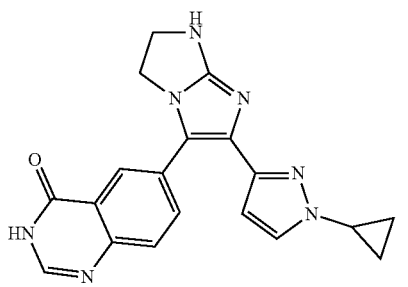 [SMILES: O=c1[nH]cnc2ccc(-c3c(-c4ccn(C5CC5)n4)nc4n3CCN4)cc12]

6-{3-(1-Cyclopropyl-1H-pyrazol-3-yl)-1,4,6-triazabicyclo[3.3.0]
octa-2,4-dien-2-yl}-3H-quinazolin-4-one;

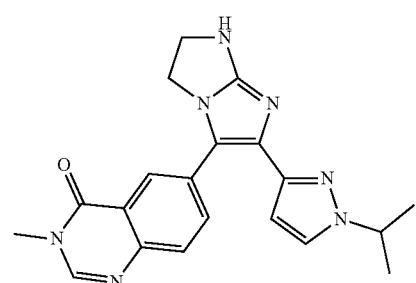

6-{3-(1-Isopropyl-1H-pyrazol-3-yl)-1,4,6-triazabicyclo[3.3.0]
octa-2,4-dien-2-yl}-3-methyl-3H-quinazolin-4-one;

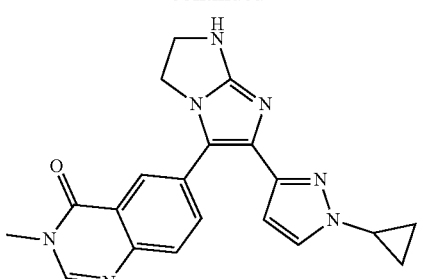

6-{3-(1-Cyclopropyl-1H-pyrazol-3-yl)-1,4,6-triazabicyclo[3.3.0]
octa-2,4-dien-2-yl}-3-methyl-3H-quinazolin-4-one;

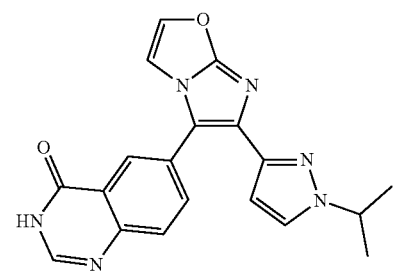

6-{7-(1-Isopropyl-1H-pyrazol-3-yl)-4-oxa-1,6-diazabicyclo[3.3.0]
octa-2,5,7-trien-8-yl}-3H-quinazolin-4-one;

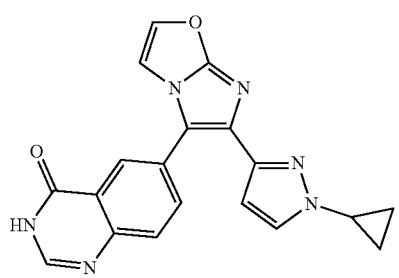

6-{7-(1-Cyclopropyl-1H-pyrazol-3-yl)-4-oxa-1,6-diazabicylo[3.3.0]
octa-2,5,7-trien-8-yl}-3H-quinazolin-4-one;

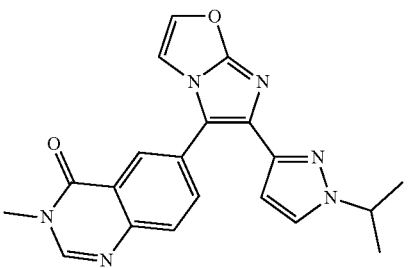

6-{7-Isopropyl-1H-pyrazol-3-yl)-4-oxa-1,6-diazabicyclo[3.3.0]
octa-2,5,7-trien-8-yl}-3-methyl-3H-quinazolin-4-one;

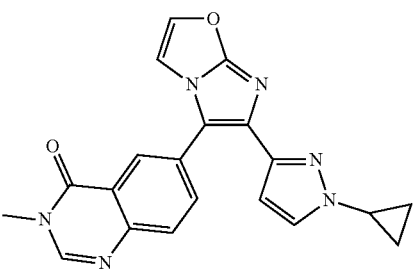

6-{7-(1-Cyclopropyl-1H-pyrazol-3-yl)-4-oxa-1,6-diazabicyclo[3.3.0]
octa-2,5,7-trien-8-yl}-3-methyl-3H-quinazolin-4-one;

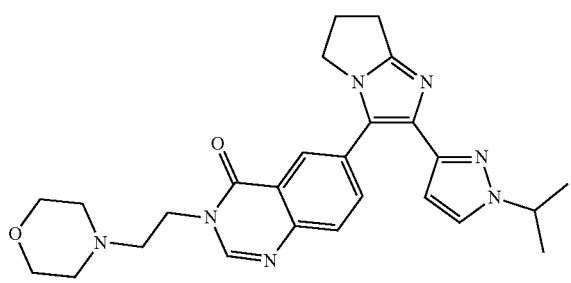

6-(3-(1-Isopropyl-1H-pyrazol-3-yl)-1,4-diazabicyclo[3.3.0]octa-2,4-dien-2-yl}-3-(2-morpholinoethyl)-3H-quinazolin-4-one;

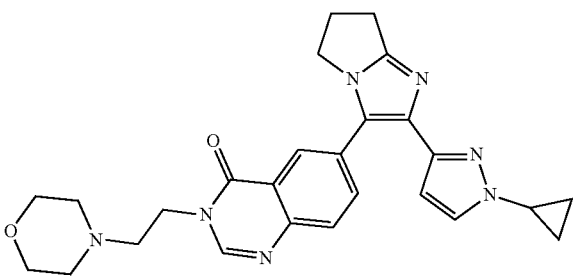

6-{3-(1-Cyclopropyl-1H-pyrazol-3-yl)-1,4-diazabicyclo[3.3.0]octa-2,4-dien-2-yl}-3-(2-morpholinoethyl)-3H-quinazolin-4-one;

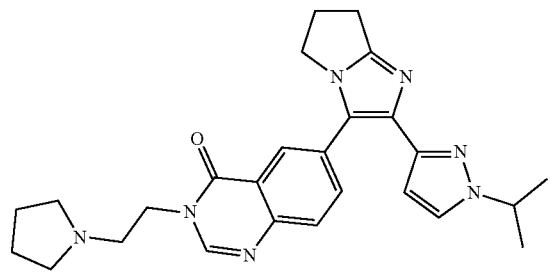

6-{3-(1-Isopropyl-1H-pyrazol-3-yl)-1,4-diazabicyclo[3.3.0]octa-2,4-dien-2-yl}-3-[2-(1-pyrrolidinyl)ethyl]-3H-quinazolin-4-one;

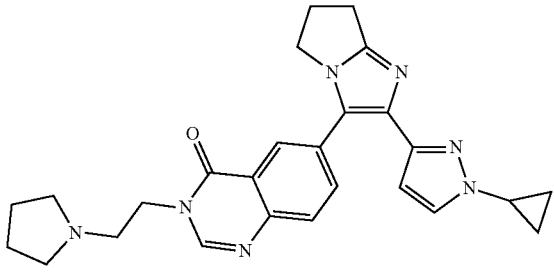

6-{3-(1-Cyclopropyl-1H-pyrazol-3-yl)-1,4-diazabicyclo[3.3.0]octa-2,4-dien-2-yl}-3-[2-(1-pyrrolidinyl)ethyl]-3H-quinazolin-4-one;

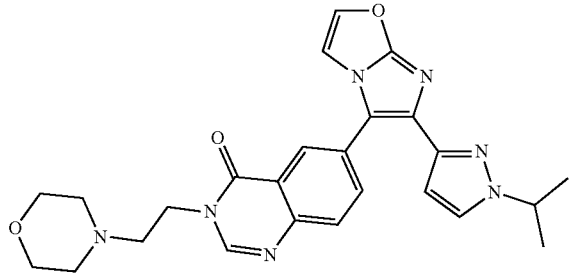

6-{7-(1-Isopropyl-1H-pyrazol-3-yl)-4-oxa-1,6-diazabicyclo[3.3.0]octa-2,5,7-trien-8-yl}-3-(2-morpholinoethyl)-3H-quinazolin-4-one;

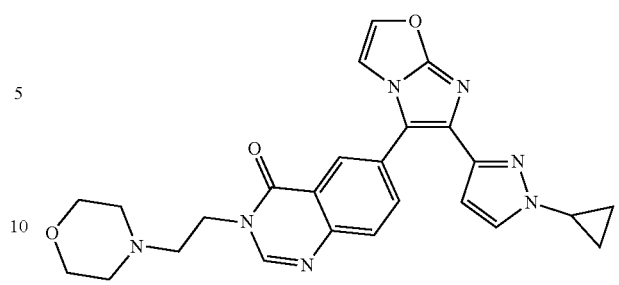

6-{7-(1-Cyclopropyl-1H-pyrazol-3-yl)-4-oxa-1,6-diazabicyclo[3.3.0]octa-2,5,7-trien-8-yl}-3-(2-morpholinoethyl)-3H-quinazolin-4-one;

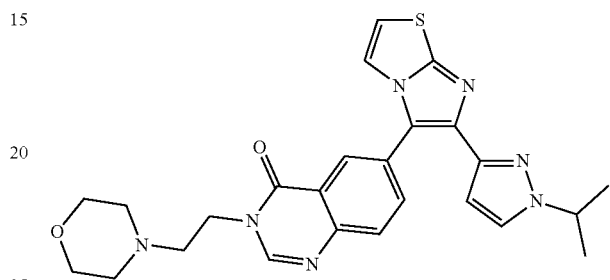

6-{7-(1-Isopropyl-1H-pyrazol-3-yl)-4-thia-1,6-diazabicyclo[3.3.0]octa-2,5,7-trien-8-yl}-3-(2-morpholinoethyl)-3H-quinazolin-4-one;

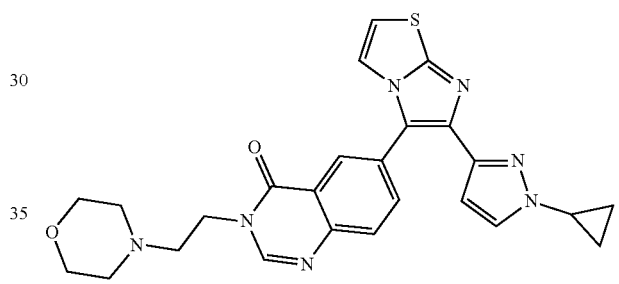

6-{7-(1-Cyclopropyl-1H-pyrazol-3-yl)-4-thia-1,6-diazabicyclo[3.3.0]octa-2,5,7-trien-8-yl}-3-(2-morpholinoethyl)-3H-quinazolin-4-one;

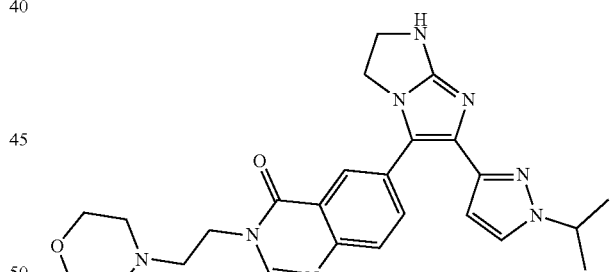

6-(3-(1-Isopropyl-1H-pyrazol-3-yl)-1,4,6-triazabicyclo[3.3.0]octa-2,4-dien-2-yl)-3-(2-morpholinoethyl)-3H-quinazolin-4-one;

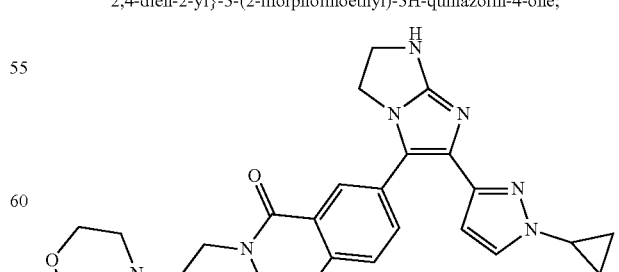

6-{3-(1-Cyclopropyl-1H-pyrazol-3-yl)-1,4,6-triazabicyclo[3.3.0]octa-2,4-dien-2-yl}-3-(2-morpholinoethyl)-3H-quinazolin-4-one;

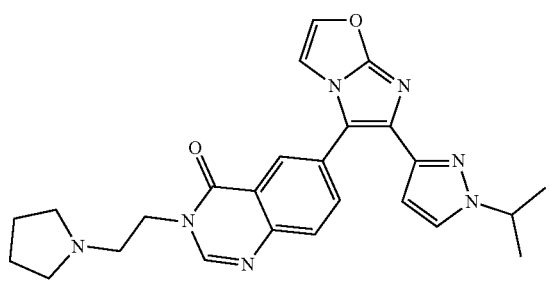

6-{7-(1-Isopropyl-1H-pyrazol-3-yl)-4-oxa-1,6-diazabicyclo[3.3.0]octa-2,5,7-trien-8-yl}-3-[2-(1-pyrrolidinyl)ethyl]-3H-quinazolin-4-one;

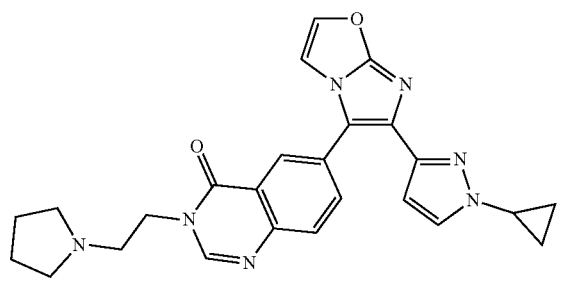

6-{7-(1-Cyclopropyl-1H-pyrazol-3-yl)-4-oxa-1,6-diazabicyclo[3.3.0]octa-2,5,7-trien-8-yl}-3-[2-(1-pyrrolidinyl)ethyl]-3H-quinazolin-4-one;

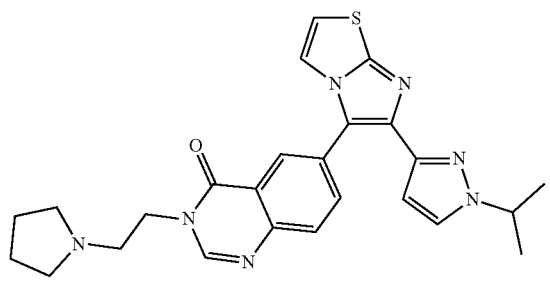

6-{7-(1-Isopropyl-1H-pyrazol-3-yl)-4-thia-1,6-diazabicyclo[3.3.0]octa-2,5,7-trien-8-yl}-3-[2-(1-pyrrolidinyl)ethyl]-3H-quinazolin-4-one;

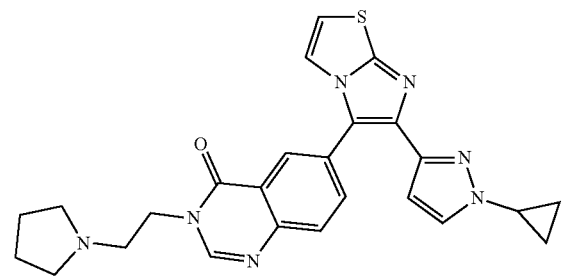

6-{7-(1-Cyclopropyl-1H-pyrazol-3-yl)-4-thia-1,6-diazabicyclo[3.3.0]octa-2,5,7-trien-8-yl}-3-[2-(1-pyrrolidinyl)ethyl]-3H-quinazolin-4-one;

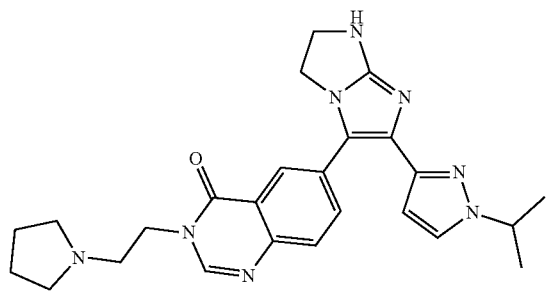 [SMILES: CC(C)n1ccc(-c2nc3n(c2-c2ccc4ncn(CCN5CCCC5)c(=O)c4c2)CCN3)n1]

6-{3-(1-Isopropyl-1H-pyrazol-3-yl)-1,4,6-triazabicyclo[3.3.0]octa-2,4-dien-2-yl}-3-[2-(1-pyrrolidinyl)ethyl]-3H-quinazolin-4-one;

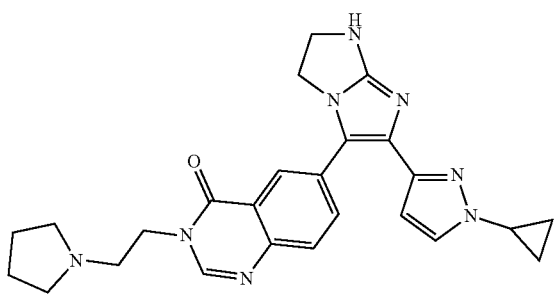 [SMILES: O=c1c2cc(-c3c(-c4ccn(C5CC5)n4)nc4n3CCN4)ccc2ncn1CCN1CCCC1]

6-{3-(1-Cyclopropyl-1H-pyrazol-3-yl)-1,4,6-triazabicyclo[3.3.0]octa-2,4-dien-2-yl}-3-[2-(1-pyrrolidinyl)ethyl]-3H-quinazolin-4-one;

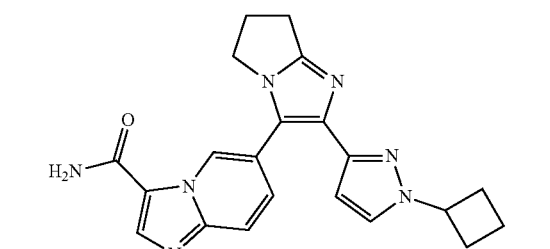

5-{3-(1-Cyclobutyl-1H-pyrazol-3-yl)-1,4-diazabicyclo[3.3.0]octa-2,4-dien-2-yl}-1,3a-diaza-3-indenecarboxamide;

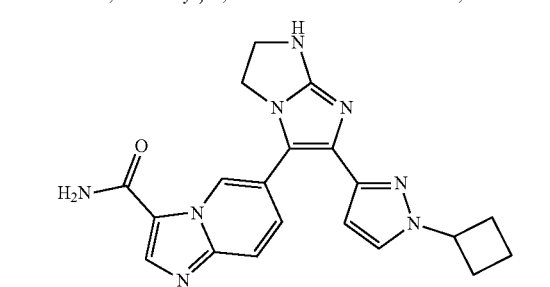

5-{3-(1-Cyclobutyl-1H-pyrazol-3-yl)-1,4,6-triazabicyclo[3.3.0]octa-2,4-dien-2-yl}-1,3a-diaza-3-indenecarboxamide;

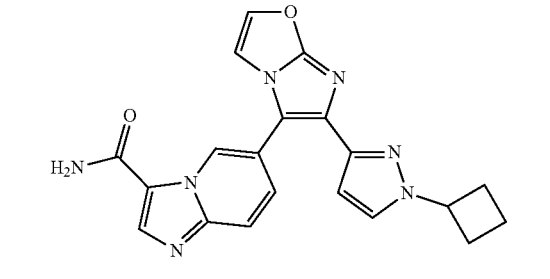

5-{7-(1-Cyclobutyl-1H-pyrazol-3-yl)-4-oxa-1,6-diazabicyclo[3.3.0]octa-2,5,7-trien-8-yl}-1,3a-diaza-3-indenecarboxamide;

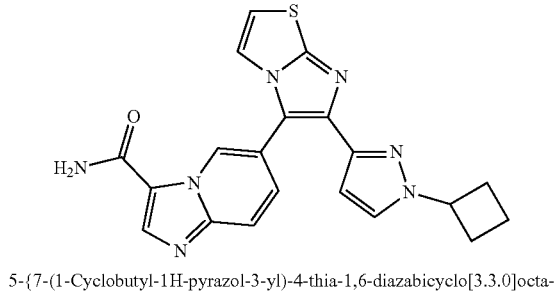

5-{7-(1-Cyclobutyl-1H-pyrazol-3-yl)-4-thia-1,6-diazabicyclo[3.3.0]octa-2,5,7-trien-8-yl}-1,3a-diaza-3-indenecarboxamide;

-continued

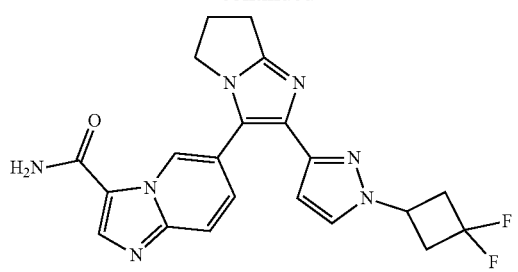

5-{3-[1-(3,3-Difluorocyclobutyl)-1H-pyrazol-3-yl]-1,4-diazabicyclo
[3.3.0]octa-2,4-dien-2-yl}-1,3a-diaza-3-indenecarboxamide;

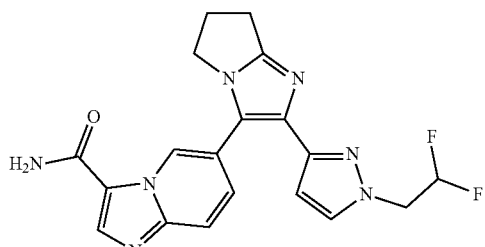

5-{3-[1-(2,2-Difluoroethyl)-1H-pyrazol-3-yl]-1,4-diazabicyclo[3.3.0]
octa-2,4-dien-2-yl}1,3a-diaza-3-indenecarboxamide;

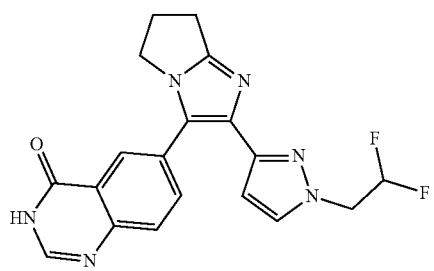

6-{3-[1-(2,2-Difluoroethyl)-1H-pyrazol-3-yl]-1,4-diazabicyclo[3.3.0]
octa-2,4-dien-2-yl}-3H-quinazolin-4-one;

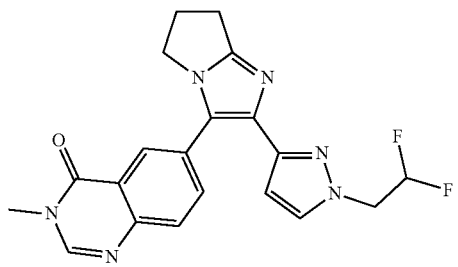

6-{3-[1-(2,2-Difluoroethyl)-1H-pyrazol-3-yl]-1,4-diazabicyclo[3.3.0]
octa-2,4-dien-2-yl}-3-methyl-3H-quinazolin-4-one;

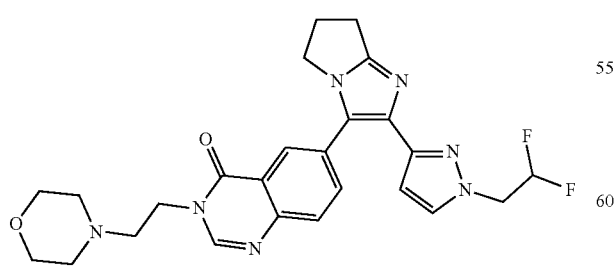

6-{3-[1-(2,2-Difluoroethyl)-1H-pyrazol-3-yl]-1,4-diazabicyclo[3.3.0]
octa-2,4-dien-2-yl}-3-(2-morpholinoethyl)-3H-quinazolin-4-one;

-continued

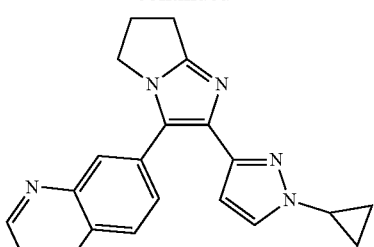

1-Cyclopropyl-3-{2-(6-quinoxalinyl)-1,4-diazabicyclo[3.3.0]
octa-2,4-dien-3-yl}-1H-pyrazole;

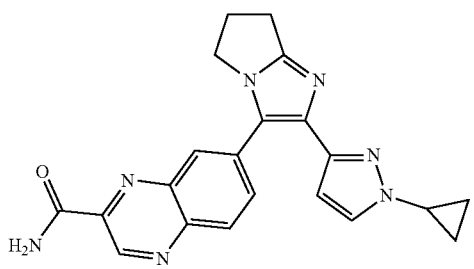

7-{3-(1-Cyclopropyl-1H-pyrazol-3-yl)-1,4-diazabicyclo[3.3.0]
octa-2,4-dien-2-yl}-2-quinoxalinecarboxamide;

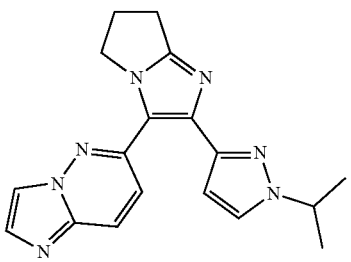

5-{3-(1-Isopropyl-1H-pyrazol-3-yl)-1,4-diazabicyclo[3.3.0]
octa-2,4-dien-2-yl}-1,3a,4-triazaindene;

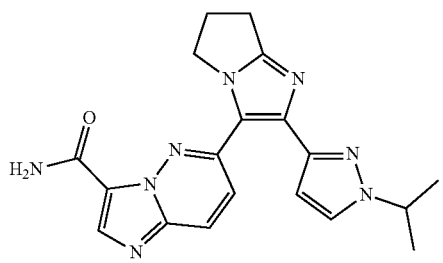

5-{3-(1-Isopropyl-1H-pyrazol-3-yl)-1,4-diazabicyclo[3.3.0]
octa-2,4-dien-2-yl}-1,3a,4-triaza-3-indenecarboxamide;

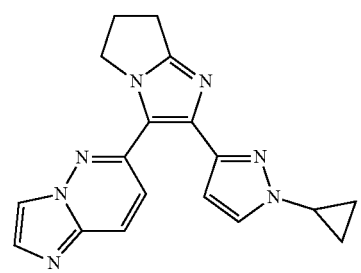

5-{3-(1-Cyclopropyl-1H-pyrazol-3-yl)-1,4-diazabicyclo[3.3.0]
octa-2,4-dien-2-yl}-1,3a,4-triazaindene;

-continued

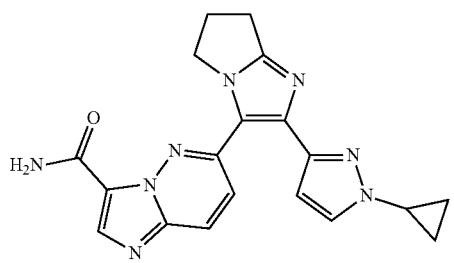

5-{3-(1-Cyclopropyl-1H-3-yl)-1,4-diazabicyclo[3.3.0]octa-2,4-dien-2-yl}-1,3a,4-triaza-3-indenecarboxamide;

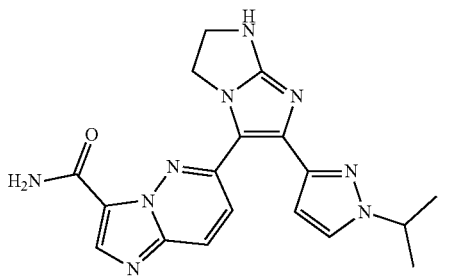

5-{3-(1-Isopropyl-1H-pyrazol-3-yl)-1,4,6-triazabicyclo[3.3.0]octa-2,4-dien-2-yl}-1,3a,4-triaza-3-indenecarboxamide;

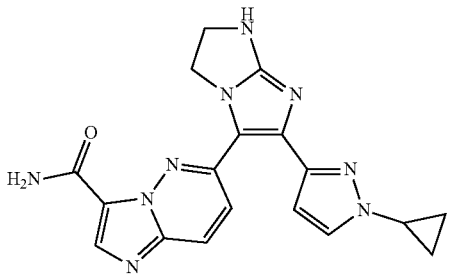

5-{3-(1-Cyclopropyl-1H-pyrazol-3-yl)-1,4,6-triazabicyclo[3.3.0]octa-2,4-dien-2-yl}-1,3a,4-triaza-3-indenecarboxamide;

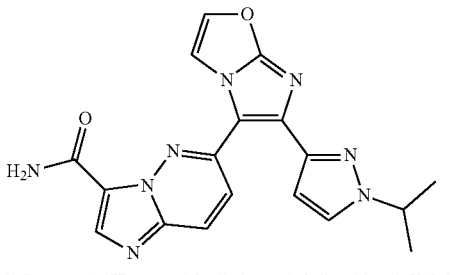

5-{7-(1-Isopropyl-1H-pyrazol-3-yl)-4-oxa-1,6-diazabicyclo[3.3.0]octa-2,5,7-trien-8-yl}-1,3a,4-triaza-3-indenecarboxamide;

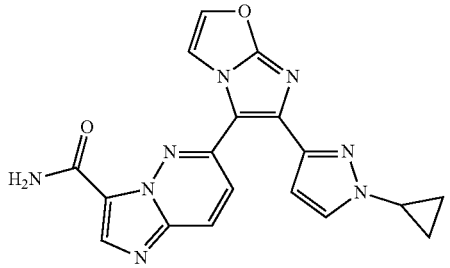

5-{7-(1-Cyclopropyl-1H-pyrazol-3-yl)-4-oxa-1,6-diazabicyclo[3.3.0]octa-2,5,7-trien-8-yl}-1,3a,4-triaza-3-indenecarboxamide;

-continued

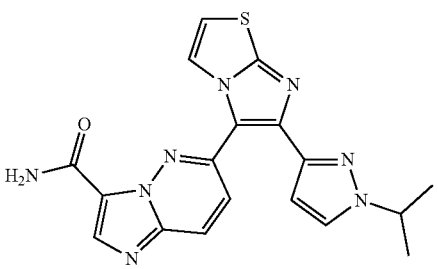

5-{7-(1-Isopropyl-1H-pyrazol-3-yl)-4-thia-1,6-diazabicyclo[3.3.0]octa-2,5,7-trien-8-yl}-1,3a,4-triaza-3-indenecarboxamide;

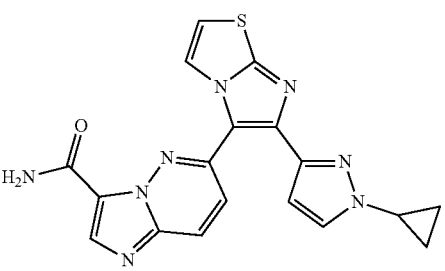

5-{7-(1-Cyclopropyl-1H-pyrazol-3-yl)-4-thia-1,6-diazabicyclo[3.3.0]octa-2,5,7-trien-8-yl}-1,3a,4-triaza-3-indenecarboxamide;

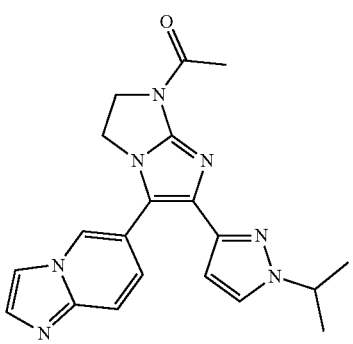 [SMILES: CC(=O)N1CCn2c1nc(-c1ccn(C(C)C)n1)c2-c1ccc2nccn2c1]

1-(5-(Imidazo[1,2-a]pyridin-6-yl)-6-(1-isopropyl-1H-pyrazol-3-yl)-2,3-dihydro-1H-imidazo[1,2-a]imidazol-1-yl)ethan-1-one;

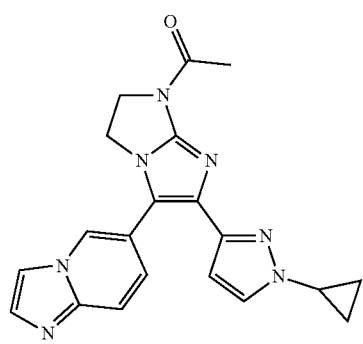 [SMILES: CC(=O)N1CCn2c1nc(-c1ccn(C3CC3)n1)c2-c1ccc2nccn2c1]

1-(6-(1-Cyclopropyl-1H-pyrazol-3-yl)-5-(imidazo[1,2-a]pyridin-yl)-2,3-dihydro-1H-imidazo[1,2-a]imidazol-1-yl)ethan-1-one;

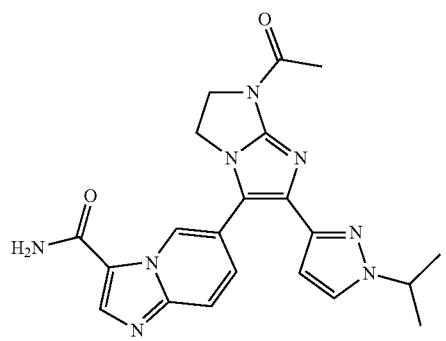

6-(1-Acetyl-6-(1-isopropyl-1H-pyrazol-3-yl)-2,3-dihydro-1H-imidazo[1,2-a]imidazol-5-yl)imidazo[1,2-a]pyridine-3-carboxamide;

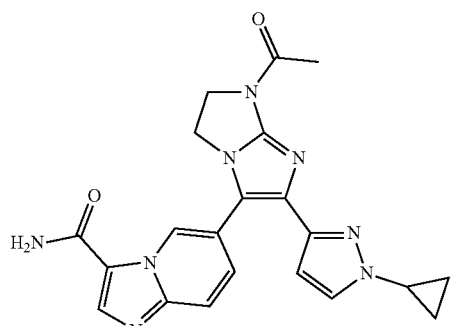

5-{6-Acetyl-3-(1-cyclopropyl-1H-pyrazol-3-yl)-1,4,6-triazabicyclo[3.3.0]octa-2,4-dien-2-yl}-1,3a-diaza-3-indenecarboxamide;

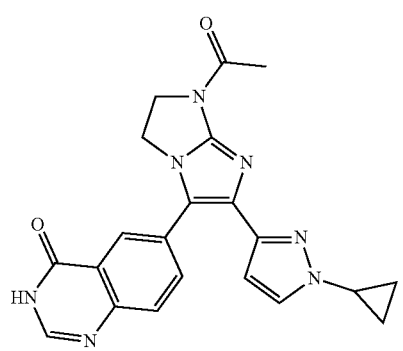 [SMILES: CC(=O)N1CCn2c1nc(-c1ccn(C3CC3)n1)c2-c1ccc2nc[nH]c(=O)c2c1]

7-(1-acetyl-6-(1-cyclopropyl-1H-pyrazol-3-yl)-2,3-dihydro-1H-imidazo[1,2-a]imidazol-5-yl)isoquinolin-1(2H)-one;

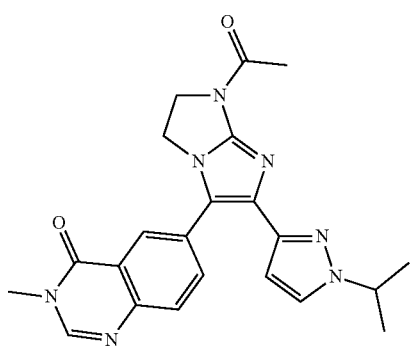 [SMILES: CC(=O)N1CCn2c1nc(-c1ccn(C(C)C)n1)c2-c1ccc2ncn(C)c(=O)c2c1]

6-(1-acetyl-6-(1-isopropyl-1H-pyrazol-3-yl)-2,3-dihydro-1H-imidazo[1,2-a]imidazol-5-yl)-3-methylquinazolin-4-(3H)-one;

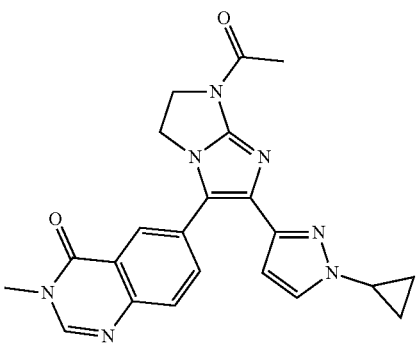 [SMILES: CC(=O)N1CCn2c1nc(-c1ccn(C3CC3)n1)c2-c1ccc2ncn(C)c(=O)c2c1]

6-(1-acetyl-6-(1-cyclopropyl-1H-pyrazol-3-yl)-2,3-dihydro-1H-imidazo[1,2-a]imidazol-5-yl)-3-methylquinazolin-4(3H)-one;

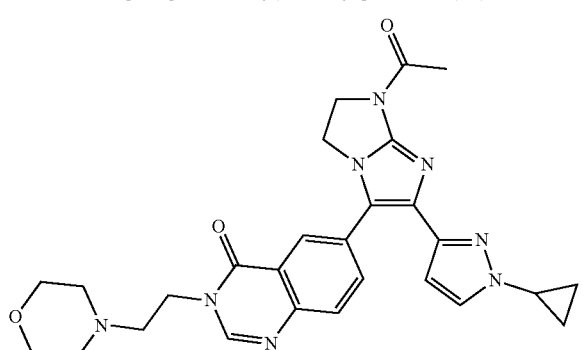

6-(1-acetyl-6-(1-cyclopropyl-1H-pyrazol-3-yl)-2,3-dihydro-1H-imidazo[1,2-a]imidazol-5-yl)-3-(2-morpholinoethyl)quinazolin-4(3H)-one;

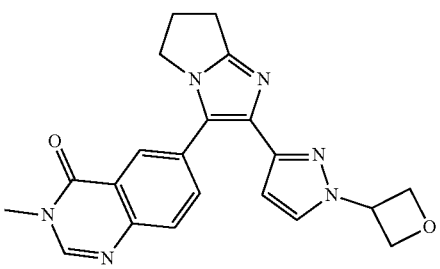

3-methyl-6-(2-(1-(oxetan-3-yl)-1H-pyrazol-3-yl)-6,7-dihydro-5H-pyrrolo[1,2-a]imidazol-3-yl)quinazolin-4(3H)-one

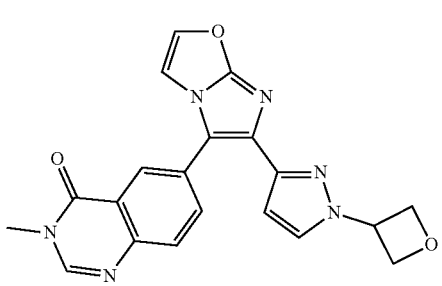

3-methyl-6-(6-(1-(oxetan-3-yl)-1H-pyrazol-3-yl)imidazo[2,1-b]oxazol-5-yl)quinazolin-4(3H)-one;

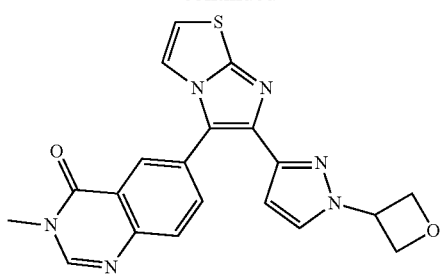

3-methyl-6-(6-(1-(oxetan-3-yl)-1H-pyrazol-3-yl)imidazo[2,1-b]
thiazol-5-yl)quinazolin-4(3H)-one;

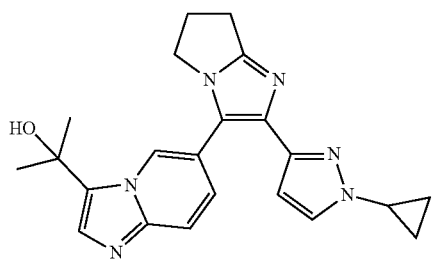

2-(6-(2-(1-cyclopropyl-1H-pyrazol-3-yl)-6,7-dihydro-5H-pyrrolo
[1,2-a]imidazol-3-yl)imidazo[1,2-a]pyridin-3-yl)propan-2-ol;

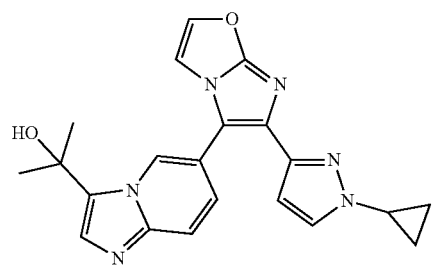

2-(6-(6-(1-cyclopropyl-1H-pyrazol-3-yl)imidazo[3m1-b]oxazol-5-yl)
imidazo[1,2-a]pyridin-3-yl)propan-2-ol;

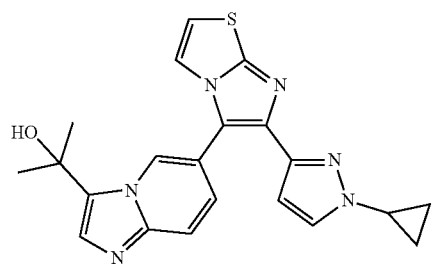

2-(6-(6-(1-cyclopropyl-1H-pyrazol-3-yl)imidazo[2,1-b]thiazol-5-yl)
imidazo[1,2-a]pyridin-3-yl)propan-2-ol;

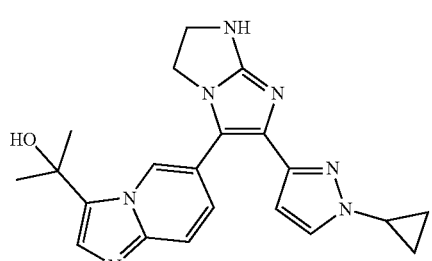

2-(6-(6-(1-cyclopropyl-1H-pyrazol-3-yl)-2,3-dihydro-1H-imidazo
[1,2-a]imidazol-5-yl)imidazo[1,2-a]pyridin-3-yl)propan-2-ol;

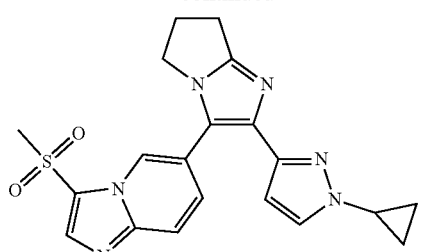

6-(2-(1-cyclopropyl-1H-pyrazol-3-yl)-6,7-dihydro-5H-pyrrolo[1,2-a]
imidazol-3-yl)-3-(methylsulfonyl)imidazo[1,2-a]pyridine;

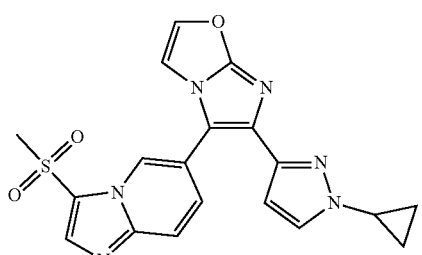

6-(1-cyclopropyl-1H-pyrazol-3-yl)-5-(3-(methylsulfonyl)imidazo[1,2-a]
pyridin-6-yl)imidazo[2,1b]oxazole;

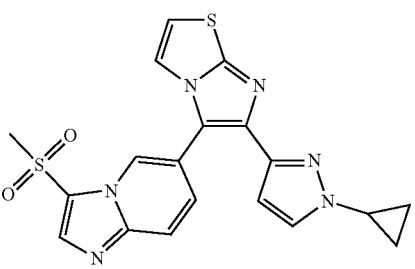

6-(1-cyclopropyl-1H-pyrazol-3-yl)-5-(3-(methylsulfonyl)
imidazo[1,2-a]pyridin-6-yl)imidazo[2,1b]thiazole;

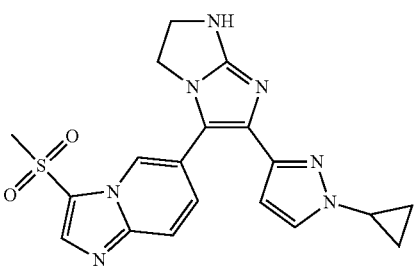 [SMILES: CS(=O)(=O)c1cnc2ccc(-c3c(-c4ccn(C5CC5)n4)nc4n3CCN4)cn12]

6-(6-(1-cyclopropyl-1H-pyrazol-3-yl)-2,3-dihydro-1H-imidazo
[1,2-a]imidazol-5-yl)-3-(methylsulfonyl)imidazo[1,2-a]pyridine;

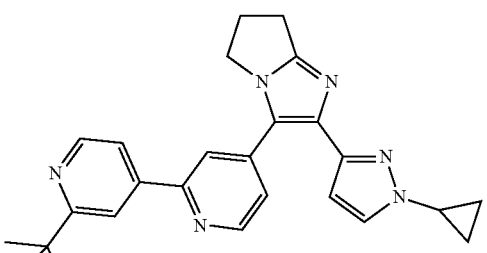

2-(4-(2-(1-cyclopropyl-1H-pyrazol-3-yl)-6,7-dihydro-5H-pyrrolo[1,2-a]
imidazol-3-yl)-[2,4'-bipyridin]-2'-yl)propan-2-ol;

-continued

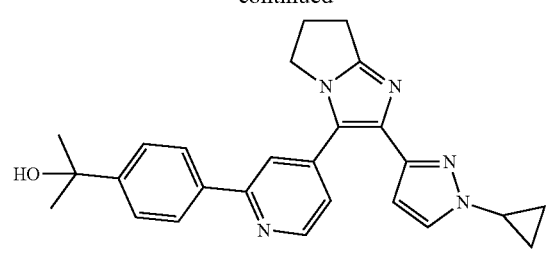

2-(4-(4-(2-(1-cyclopropyl-1H-pyrazol-3-yl)-6,7-dihydro-5H-pyrrolo
[1,2-a]imidazol-3-yl)pyridin-2-yl)phenyl)propan-2-ol;

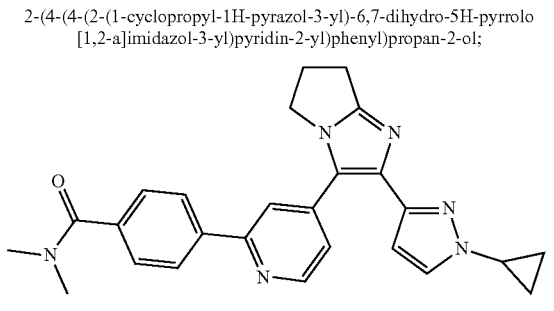

4-(4-(2-(1-cyclopropyl-1H-pyrazol-3-yl)-6,7-dihydro-5H-pyrrolo[1,2-a]
imidazol-3-yl)pyridin-2-yl)-N,N-dimethylbenzamide;

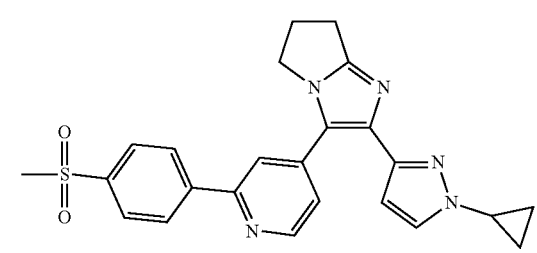

2-(1-cyclopropyl-1H-pyrazol-3-yl)-3-(2-(4-(methylsulfonyl)phenyl)
pyridin-4-yl)-6,7-dihydro-5H-pyrrolo[1,2-a]imidazole;

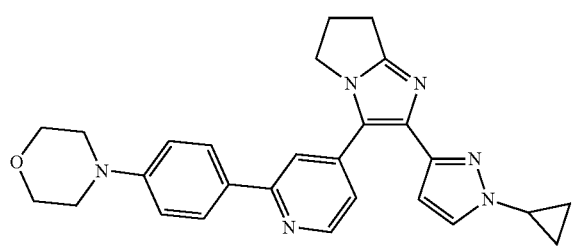

4-(4-(4-(2-(1-cyclopropyl-1H-pyrazol-3-yl)-6,7-dihydro-5H-pyrrolo
[1,2-a]imidazol-3-yl)pyridin-2-yl)phenyl)morpholine;

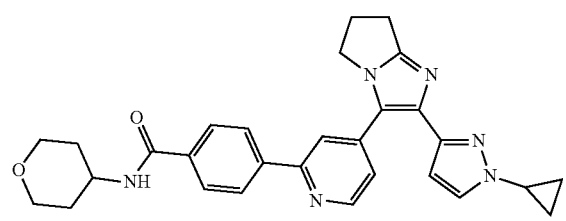

4-(4-(2-(1-cyclopropyl-1H-pyrazol-3-yl)-6,7-dihydro-5H-pyrrolo[1,2-a]
imidazol-3-yl)pyridin-2-yl)-N-(tetrahydro-2H-pyran-4-yl)benzamide;

-continued

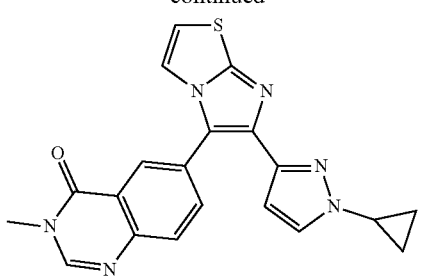

6-{7-(1-Cyclopropyl-1H-pyrazol-3-yl)-4-thia-1,6-diazabicyclo[3.3.0]
octa-2,5,7-trien-8-yl}-3-methyl-3H-quinazolin-4-one;

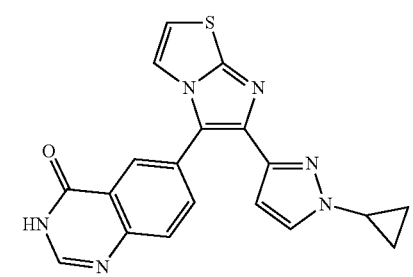

6-{7-(1-Cyclopropyl-1H-pyrazol-3-yl)-4-thia-1,6-diazabicyclo[3.3.0]
octa-2,5,7-trien-8-yl}-3H-quinazolin-4-one;

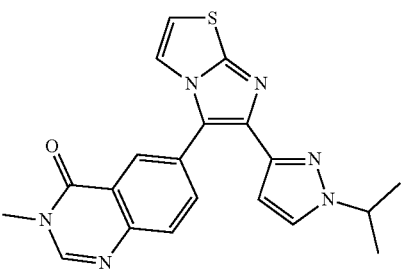

6-(6-(1-isopropyl-1H-pyrazol-3-yl)imidazo[2,1-b]thiazol-5-yl)-3-
methylquinazolin-4(3H)-one;

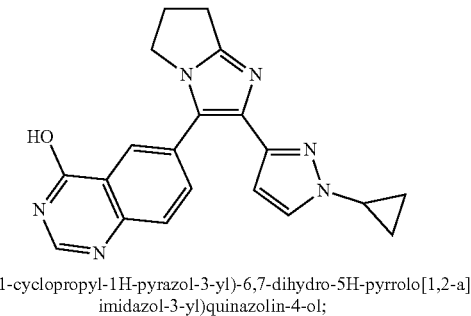

6-(2-(1-cyclopropyl-1H-pyrazol-3-yl)-6,7-dihydro-5H-pyrrolo[1,2-a]
imidazol-3-yl)quinazolin-4-ol;

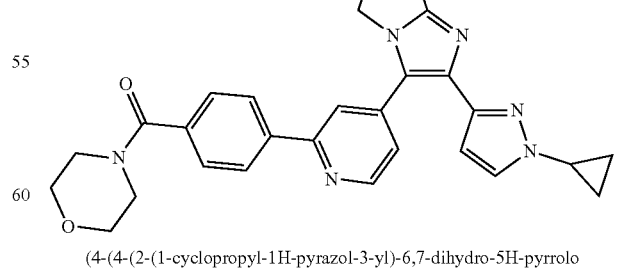

(4-(4-(2-(1-cyclopropyl-1H-pyrazol-3-yl)-6,7-dihydro-5H-pyrrolo
[1,2-a]imidazol-3-yl)pyridin-2-yl)phenyl)(morpholino)methanone;

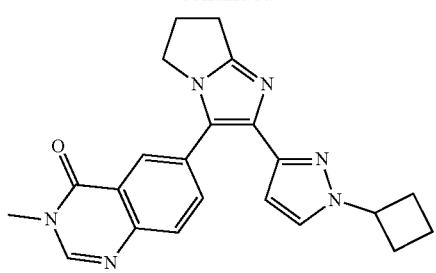

6-(2-(1-cyclobutyl-1H-pyrazol-3-yl)-6,7-dihydro-5H-pyrrolo[1,2-a]
imidazol-3-yl)-3-methylquinazolin-4(3H)-one;

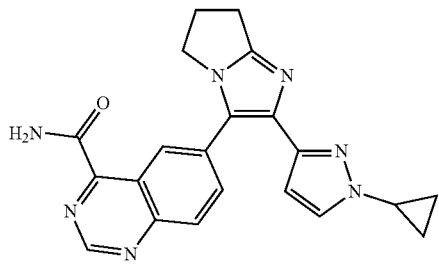

6-(2-(1-cyclopropyl-1H-pyrazol-3-yl)-6,7-dihydro-5H-pyrrolo[1,2-a]
imidazol-3-yl)quinazoline-4-carboxamide;

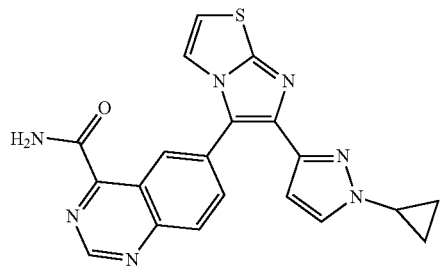

6-(6-(1-cyclopropyl-1H-pyrazol-3-yl)imidazo[2,1-b]thiazol-5-yl)
quinazoline-4-carboxamide;

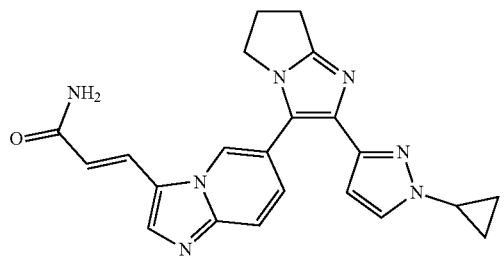

(E)-3-(5-{3-(1-Cyclopropyl-1H-pyrazol-3-yl)-1,4-diazabicyclo[3.3.0]
octa-2,4-dien-2-yl}-1,3a-diaza-4-indenyl)acrylamide;

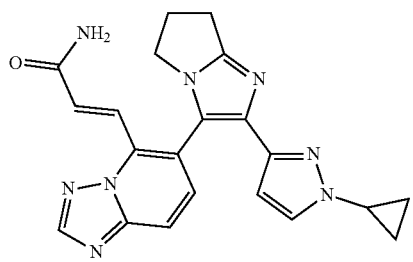

(E)-3-(5-{3-(1-Cyclopropyl-1H-pyrazol-3-yl)-1,4-diazabicyclo[3.3.0]
octa-2,4-dien-2-yl}-1,3,3a-triaza-4-indenyl)acrylamide;

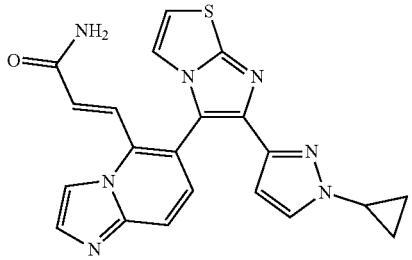

(E)-3-(5-{7-(1-Cyclopropyl-1H-pyrazol-3-yl)-4-thia-1,6-diazabicyclo
[3.3.0]octa-2,5,7-trien-8-yl}-1,3a-diaza-4-indenyl)acrylamide;

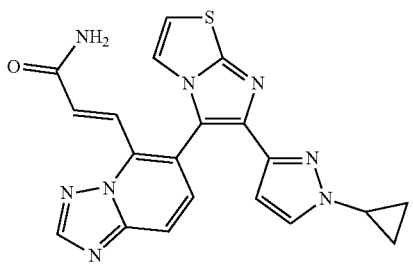

(E)-3-(5-{7-(1-Cyclopropyl-1H-pyrazol-3-yl)-4-thia-1,6-diazabicyclo
[3.3.0]octa-2,5,7-trien-8-yl}-1,3,3a-triaza-4-indenyl)acrylamide;

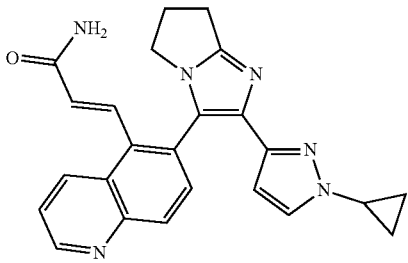

E)-3-(6-{3-(1-Cyclopropyl-1H-pyrazol-3-yl)-1,4-diazabicyclo[3.3.0]
octa-2,4-dien-2-yl}-5-quinolyl)acrylamide;

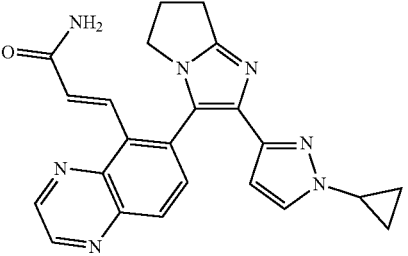

(E)-3-(6-{3-(1-Cyclopropyl-1H-pyrazol-3-yl)-1,4-diazabicyclo[3.3.0]
octa-2,4-dien-2-yl}-5-quinoxalinyl)acrylamide;

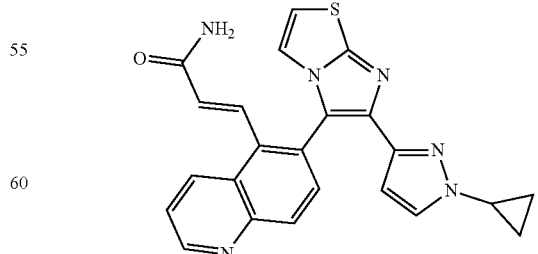

(E)-3-(6-{7-(1-Cyclopropyl-1H-pyrazol-3-yl)-4-thia-1,6-diazabicyclo
[3.3.0]octa-2,5,7-trien-8-yl}-5-quinolyl)acrylamide;

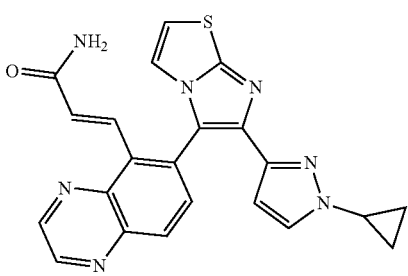

(E)-3-(6-{7-(1-Cyclopropyl-1H-pyrazol-3-yl)-4-thia-1,6-diazabicyclo
[3.3.0]octa-2,5,7-trien-8-yl}-5-quinoxalinyl)acrylamide;

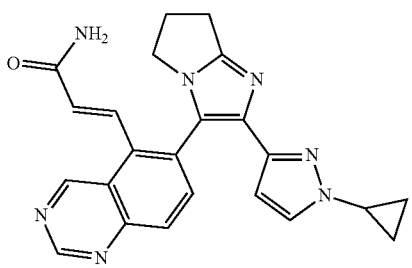

(E)-3-(6-{3-(1-Cyclopropyl-1H-pyrazol-3-yl)-1,4-diazabicyclo[3.3.0]
octa-2,4-dien-2-yl}-5-quinazolinyl)acrylamide;

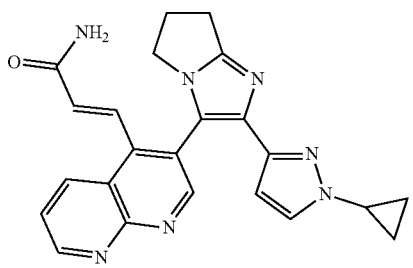

(E)-3-(3-{3-(1-Cyclopropyl-1H-pyrazol-3-yl)-1,4-diazabicyclo[3.3.0]
octa-2,4-dien-2-yl}-1,8-diaza-4-naphthyl)acrylamide;

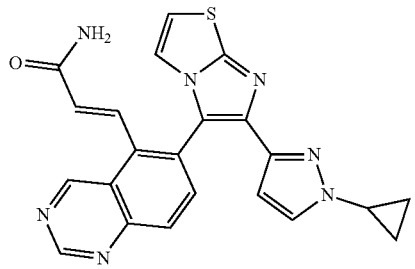

(E)-3-(6-{7-(1-Cyclopropyl-1H-pyrazol-3-yl)-4-thia-1,6-diazabicyclo
[3.3.0]octa-2,5,7-trien-8-yl}-5-quinazolinyl)acrylamide;

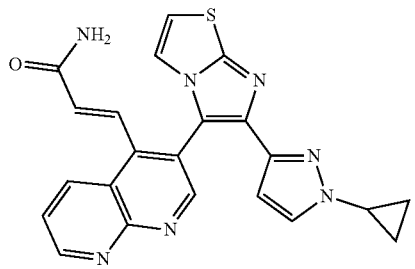

(E)-3-(3-{7-(1-Cyclopropyl-1H-pyrazol-3-yl)-4-thia-1,6-diazabicyclo
[3.3.0]octa-2,5,7-trien-8-yl}-1,8-diaza-4-naphthyl)acrylamide;

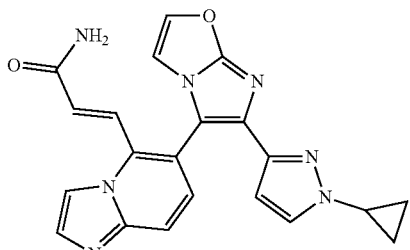

(E)-3-(5-{7-(1-Cyclopropyl-1H-pyrazol-3-yl)-4-oxa-1,6-diazabicyclo
[3.3.0]octa-2,5,7-trien-8-yl}-1,3a-diaza-4-indenyl)acrylamide;

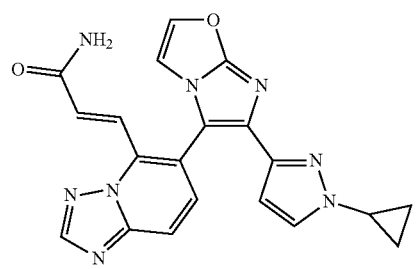

(E)-3-(5-{7-(1-Cyclopropyl-1H-pyrazol-3-yl)-4-oxa-1,6-diazabicyclo
[3.3.0]octa-2,5,7-trien-8-yl}-1,3,3a-triaza-4-indenyl)acrylamide;

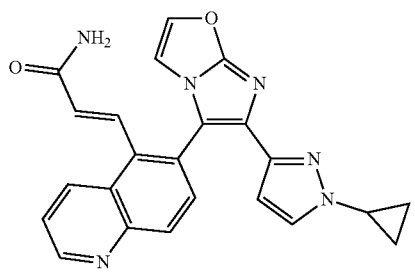

(E)-3-(6-{7-(1-Cyclopropyl-1H-pyrazol-3-yl)-4-oxa-1,6-diazabicyclo
[3.3.0]octa-2,5,7-trien-8-yl}-5-quinolyl)acrylamide;

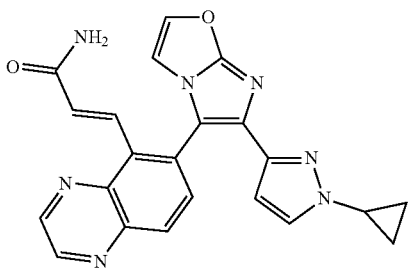

(E)-3-(6-{7-(1-Cyclopropyl-1H-pyrazol-3-yl)-4-oxa-1,6-diazabicyclo
[3.3.0]octa-2,5,7-trien-8-yl}-5-quinoxalinyl)acrylamide;

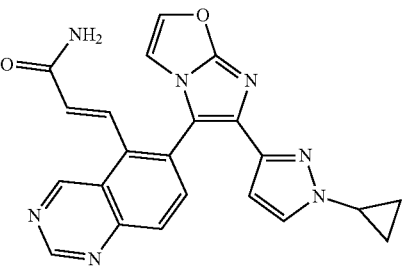

(E)-3-(6-{7-(1-Cyclopropyl-1H-pyrazol-3-yl)-4-oxa,6-diazabicyclo
[3.3.0]octa-2,5,7-trien-8-yl}-5-quinazolinyl)acrylamide;

or

-continued

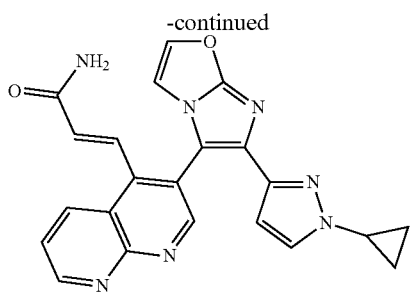

(E)-3-(3-{7-(1-Cyclopropyl-1H-pyrazol-3-yl)-4-oxa-1,6-diazabicyclo[3.3.0]octa-2,5,7-trien-8-yl}-1,8-diaza-4-naphthyl)acrylamide.

5. The compound of claim 1, wherein the compound is:

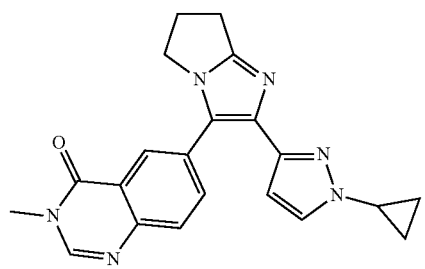 [SMILES: Cn1cnc2ccc(-c3c(-c4ccn(C5CC5)n4)nc4n3CCC4)cc2c1=O]

6-{3-(1-cyclopropyl-1H-pyrazol-3-yl)-1,4-diazabicyclo[3.3.0]octa-2,4-dien-2-yl}-3-methyl-3H-quinazolin-4-one.

6. The compound of claim 1, wherein the compound is:

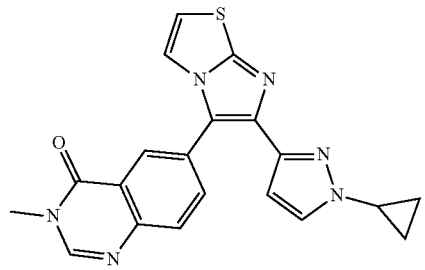 [SMILES: Cn1cnc2ccc(-c3c(-c4ccn(C5CC5)n4)nc4sccn34)cc2c1=O]

6-{7-(1-cyclopropyl-1H-pyrazol-3-yl)-4-thia-1,6-diazabicyclo[3.3.0]octa-2,5,7-trien-8-yl}-3-methyl-3H-quinazolin-4-one.

7. The compound of claim 1, wherein the compound is:

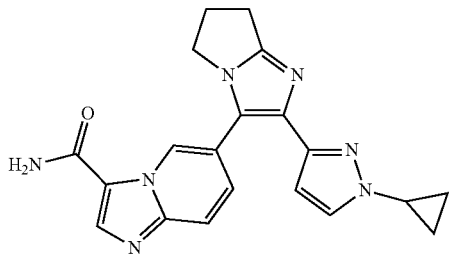 [SMILES: NC(=O)c1cnc2ccc(-c3c(-c4ccn(C5CC5)n4)nc4n3CCC4)cn12]

5-{3-(1-cyclopropyl-1H-pyrazol-3-yl)-1,4-diazabicyclo[3.3.0]octa-2,4-dien-2-yl}-1,3a-diaza-3-indenecarboxamide.

8. The compound of claim 1, wherein the compound is:

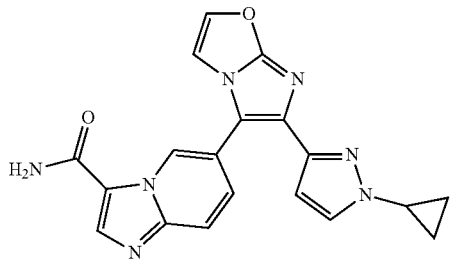

5-{7-(1-cyclopropyl-1H-pyrazol-3-yl)-4-oxa-1,6-diazabicyclo[3.3.0]octa-2,5,7-trien-8-yl}-1,3a-diaza-3-indenecarboxamide.

9. The compound of claim 1, wherein the compound is:

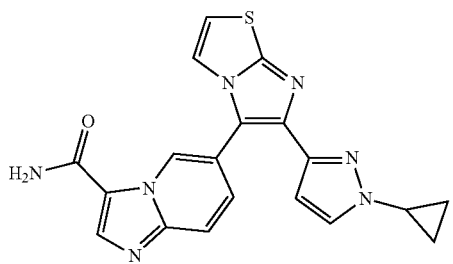 [SMILES: NC(=O)c1cnc2ccc(-c3c(-c4ccn(C5CC5)n4)nc4occn34)cn12]

5-{7-(1-cyclopropyl-1H-pyrazol-3-yl)-4-thia-1,6-diazabicyclo[3.3.0]octa-2,5,7-trien-8-yl}-1,3a-diaza-3-indenecarboxamide.

10. The compound of claim 1, wherein the compound is:

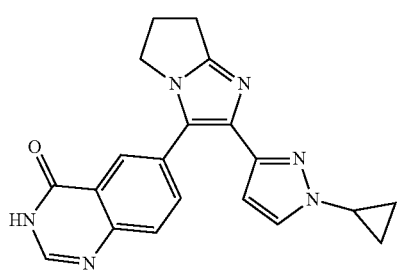 [SMILES: O=c1[nH]cnc2ccc(-c3c(-c4ccn(C5CC5)n4)nc4n3CCC4)cc12]

6-{3-(1-cyclopropyl-1H-pyrazol-3-yl)-1,4-diazabicyclo[3.3.0]octa-2,4-dien-2-yl}-3H-quinazolin-4-one.

11. The compound of claim 1, wherein the compound is:

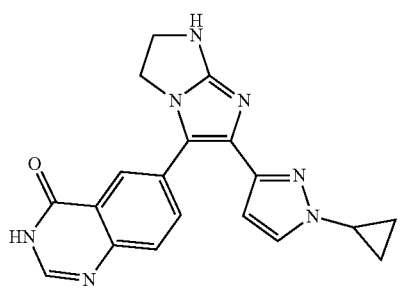 [SMILES: O=c1[nH]cnc2ccc(-c3c(-c4ccn(C5CC5)n4)nc4n3CCN4)cc12]

6-{3-(1-cyclopropyl-1H-pyrazol-3-yl)-1,4,6-triazabicyclo[3.3.0]octa-2,4-dien-2-yl}-3H-quinazolin-4-one.

12. The compound of claim 1, wherein the compound is:

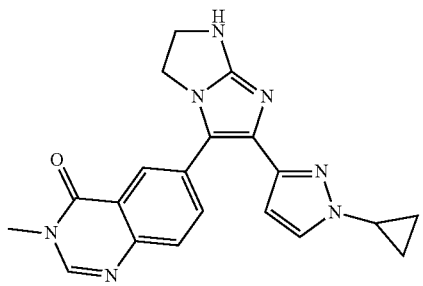 [SMILES: Cn1cnc2ccc(-c3c(-c4ccn(C5CC5)n4)nc4n3CCN4)cc2c1=O]

6-{3-(1-cyclopropyl-1H-pyrazol-3-yl)-1,4,6-triazabicyclo[3.3.0]octa-2,4-dien-2-yl}-3-methyl-3H-quinazolin-4-one.

13. The compound of claim 1, wherein the compound is:

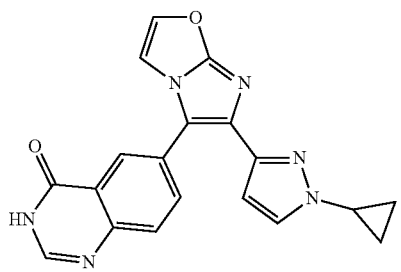 [SMILES: O=c1[nH]cnc2ccc(-c3c(-c4ccn(C5CC5)n4)nc4occn34)cc12]

6-{7-(1-cyclopropyl-1H-pyrazol-3-yl)-4-oxa-1,6-diazabicyclo[3.3.0]octa-2,5,7-trien-8-yl}-3H-quinazolin-4-one, or

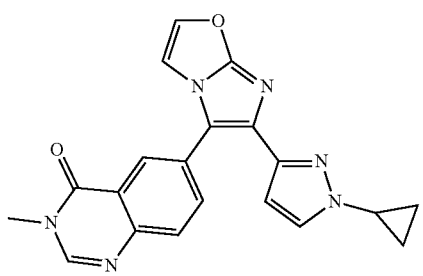 [SMILES: Cn1cnc2ccc(-c3c(-c4ccn(C5CC5)n4)nc4occn34)cc2c1=O]

6-{7-(1-cyclopropyl-1H-pyrazol-3-yl)-4-oxa-1,6-diazabicyclo[3.3.0]octa-2,5,7-trien-8-yl}-3-methyl-3H-quinazolin-4-one.

14. The compound of claim 1, wherein the compound is:

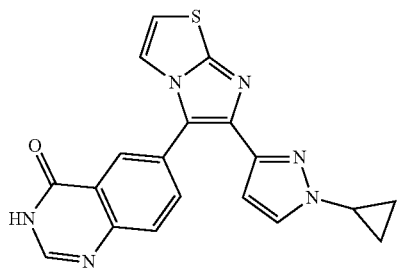 [SMILES: O=c1[nH]cnc2ccc(-c3c(-c4ccn(C5CC5)n4)nc4sccn34)cc12]

6-{7-(1-cyclopropyl-1H-pyrazol-3-yl)-4-thia-1,6-diazabicyclo[3.3.0]octa-2,5,7-trien-8-yl}-3H-quinazolin-4-one.

15. The compound of claim 1, wherein the compound is:

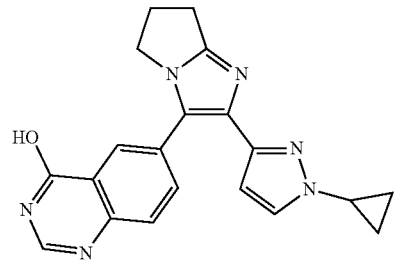 [SMILES: Oc1ncnc2ccc(-c3c(-c4ccn(C5CC5)n4)nc4n3CCC4)cc12]

6-(2-(1-cyclopropyl-1H-pyrazol-3-yl)-6,7-dihydro-5H-pyrrolo[1,2-a]imidazol-3-yl)quinazolin-4-ol.

16. The compound of claim 1, wherein the compound is:

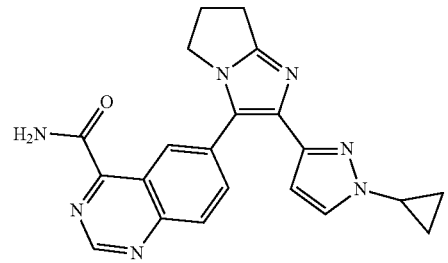 [SMILES: NC(=O)c1ncnc2ccc(-c3c(-c4ccn(C5CC5)n4)nc4n3CCC4)cc12]

6-(2-(1-cyclopropyl-1H-pyrazol-3-yl)-6,7-dihydro-5H-pyrrolo[1,2-a]imidazol-3-yl)quinazoline-4-carboxamide.

17. The compound of claim 1, wherein the compound is:

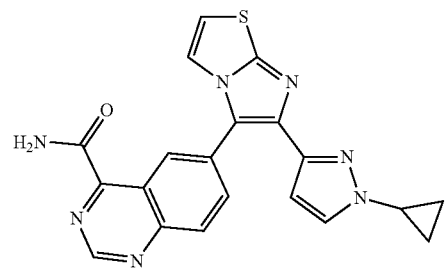 [SMILES: NC(=O)c1ncnc2ccc(-c3c(-c4ccn(C5CC5)n4)nc4sccn34)cc12]

6-(6-(1-cyclopropyl-1H-pyrazol-3-yl)imidazo[2,1-b]thiazol-5-yl)quinazoline-4-carboxamide.

18. The compound of claim 1, wherein the compound is:

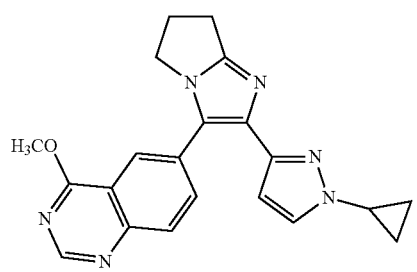 [SMILES: COc1ncnc2ccc(-c3c(-c4ccn(C5CC5)n4)nc4n3CCC4)cc12]

6-(2-(1-cyclopropyl-1H-pyrazol-3-yl)-6,7-dihydro-5H-pyrrolo[1,2-a]imidazol-3-yl)-4-methoxyquinazoline.

19. A method of ameliorating or alleviating a disease comprising administering a therapeutically effective amount of a compound of claim 1, or a pharmaceutically acceptable salt, hydrate, or solvate thereof, to a mammal in need of treatment, wherein the disease is atherosclerosis, Marfan syndrome, Loeys-Dietz syndrome, obesity, diabetes, multiple sclerosis, keratoconus, idiopathic pulmonary fibrosis, Alzheimer's Disease, chronic kidney disease, scleroderma, lung cancer, gastric cancer, myelodysplastic syndrome (MDS), melanoma, colon cancer, renal cancer, glioblastoma, pancreatic cancer, or hepatocellular carcinoma.

* * * * *